(12) United States Patent
Tegg et al.

(10) Patent No.: US 12,263,014 B2
(45) Date of Patent: Apr. 1, 2025

(54) HIGH-DENSITY ELECTRODE CATHETERS WITH MAGNETIC POSITION TRACKING

(71) Applicant: St. Jude Medical, Cardiology Division, Inc., St. Paul, MN (US)

(72) Inventors: Troy T. Tegg, Elk River, MN (US); Gregory K. Olson, Elk River, MN (US); Timothy S. Marass, Minneapolis, MN (US); Derek C. Sutermeister, Ham Lake, MN (US); Bruce Ebner, Shorewood, MN (US); Hong Cao, Savage, MN (US); Vladislav Dmidrievich Popov, Plymouth, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 497 days.

(21) Appl. No.: 17/405,442

(22) Filed: Aug. 18, 2021

(65) Prior Publication Data

US 2022/0054198 A1 Feb. 24, 2022

Related U.S. Application Data

(60) Provisional application No. 63/067,284, filed on Aug. 18, 2020.

(51) Int. Cl.
*A61B 18/14* (2006.01)
*A61B 5/00* (2006.01)
(Continued)

(52) U.S. Cl.
CPC ........ *A61B 5/6859* (2013.01); *A61B 18/1492* (2013.01); *A61B 34/20* (2016.02);
(Continued)

(58) Field of Classification Search
CPC .. A61B 2562/0223; A61B 2018/00636; A61B 18/00085; A61B 5/6858;
(Continued)

(56) References Cited

U.S. PATENT DOCUMENTS 4,522,212 A 6/1985 Gelinas et al.
5,224,939 A 7/1993 Holman et al.
(Continued)

FOREIGN PATENT DOCUMENTS

AU 2015202258 A1 5/2015
AU 2016204351 A1 1/2017
(Continued)

*Primary Examiner* — Eun Hwa Kim
*Assistant Examiner* — Matthew David Becton
(74) *Attorney, Agent, or Firm* — Kilpatrick Townsend & Stockton LLP

(57) ABSTRACT

Various embodiments of the present disclosure can include a high-density electrode catheter. In some embodiments, the high-density electrode catheter can include a catheter shaft including a proximal end and a distal end, the catheter shaft defining a catheter shaft longitudinal axis. In some embodiments, the high-density electrode catheter can include a shaft magnetic position sensor disposed along a distal portion of the catheter shaft. In some embodiments, the high-density electrode catheter can include a flexible tip portion located adjacent to the distal end of the catheter shaft, wherein the flexible tip portion includes a flexible framework. In some embodiments, the high-density electrode catheter can include a plurality of electrodes disposed on the flexible framework. In some embodiments, the high-density electrode catheter can include a tip magnetic position sensor disposed on a portion of the flexible framework.

14 Claims, 38 Drawing Sheets

(51) Int. Cl.
  *A61B 5/287* (2021.01)
  *A61B 18/00* (2006.01)
  *A61B 34/20* (2016.01)
  *A61B 34/00* (2016.01)

(52) U.S. Cl.
  CPC ............ *A61B 5/287* (2021.01); *A61B 5/6858* (2013.01); *A61B 2018/0016* (2013.01); *A61B 2018/00267* (2013.01); *A61B 2018/00351* (2013.01); *A61B 2018/00357* (2013.01); *A61B 2018/00577* (2013.01); *A61B 2018/00839* (2013.01); *A61B 2018/1465* (2013.01); *A61B 2018/1467* (2013.01); *A61B 2034/2051* (2016.02); *A61B 34/25* (2016.02); *A61B 2560/0462* (2013.01); *A61B 2562/0223* (2013.01)

(58) Field of Classification Search
  CPC .................. A61B 5/6859; A61B 5/287; A61B 2018/0016; A61B 2018/00267; A61B 2018/1467; A61B 1/00085
  See application file for complete search history.

(56) References Cited

U.S. PATENT DOCUMENTS

| | | |
|---|---|---|
| 5,380,301 A | 1/1995 | Prichard et al. |
| 5,400,783 A | 3/1995 | Pomeranz et al. |
| 5,456,254 A | 10/1995 | Pietroski et al. |
| 5,626,136 A | 5/1997 | Webster, Jr. |
| 5,702,438 A | 12/1997 | Avitall |
| 5,715,817 A | 2/1998 | Stevens-Wright et al. |
| 5,715,832 A | 2/1998 | Koblish et al. |
| 5,722,401 A * | 3/1998 | Pietroski ............ A61B 5/6858 600/374 |
| 5,827,278 A | 10/1998 | Webster, Jr. |
| 5,876,373 A | 3/1999 | Giba et al. |
| 5,964,757 A | 10/1999 | Ponzi |
| 6,029,091 A | 2/2000 | de la Rama et al. |
| 6,071,282 A | 6/2000 | Fleischman |
| 6,074,379 A | 6/2000 | Prichard |
| 6,123,699 A | 9/2000 | Webster, Jr. |
| 6,171,277 B1 | 1/2001 | Ponzi |
| 6,183,463 B1 | 2/2001 | Webster, Jr. |
| 6,198,974 B1 | 3/2001 | Webster, Jr. |
| 6,210,407 B1 | 4/2001 | Webster |
| 6,233,476 B1 | 5/2001 | Strommer et al. |
| 6,267,746 B1 | 7/2001 | Bumbalough |
| 6,273,404 B1 | 8/2001 | Holman et al. |
| 6,415,187 B1 | 7/2002 | Kuzma et al. |
| 6,491,681 B1 | 12/2002 | Kunis et al. |
| 6,498,944 B1 | 12/2002 | Ben-Haim et al. |
| 6,522,932 B1 | 2/2003 | Kuzma et al. |
| 6,554,794 B1 | 4/2003 | Mueller et al. |
| 6,652,515 B1 | 11/2003 | Maguire et al. |
| 6,658,302 B1 | 12/2003 | Kuzma et al. |
| 6,690,963 B2 | 2/2004 | Ben-Haim et al. |
| 6,788,967 B2 | 9/2004 | Ben-Haim et al. |
| 6,961,602 B2 | 11/2005 | Fuimaono et al. |
| 7,004,937 B2 | 2/2006 | Lentz et al. |
| 7,027,851 B2 | 4/2006 | Mejia |
| 7,089,045 B2 | 8/2006 | Fuimaono et al. |
| 7,099,712 B2 | 8/2006 | Fuimaono et al. |
| 7,197,354 B2 | 3/2007 | Sobe |
| 7,214,220 B2 | 5/2007 | McGlinch et al. |
| 7,217,256 B2 | 5/2007 | Di Palma |
| 7,228,164 B2 | 6/2007 | Fuimaono et al. |
| 7,257,435 B2 | 8/2007 | Plaza |
| 7,263,397 B2 | 8/2007 | Hauck et al. |
| 7,386,339 B2 | 6/2008 | Strommer et al. |
| 7,412,274 B2 | 8/2008 | Mejia |
| 7,429,261 B2 | 9/2008 | Kunis et al. |
| 7,561,907 B2 | 7/2009 | Fuimaono et al. |
| 7,608,063 B2 | 10/2009 | Le et al. |
| 7,625,365 B2 | 12/2009 | McGlinch et al. |
| 7,666,204 B2 | 2/2010 | Thornton et al. |
| 7,959,601 B2 | 6/2011 | McDaniel et al. |
| 7,985,215 B2 | 7/2011 | Guo et al. |
| 8,103,327 B2 | 1/2012 | Harlev et al. |
| 8,137,321 B2 | 3/2012 | Argentine |
| 8,157,848 B2 | 4/2012 | Zhang et al. |
| 8,221,390 B2 | 7/2012 | Pal et al. |
| 8,271,099 B1 | 9/2012 | Swanson |
| 8,273,016 B2 | 9/2012 | O'Sullivan |
| 8,376,990 B2 | 2/2013 | Ponzi et al. |
| 8,391,947 B2 | 3/2013 | Urman et al. |
| 8,447,377 B2 | 5/2013 | Harlev et al. |
| 8,486,063 B2 | 7/2013 | Werneth et al. |
| 8,565,894 B2 | 10/2013 | Vetter et al. |
| 8,603,069 B2 | 12/2013 | Selkee |
| 8,608,703 B2 | 12/2013 | Riles et al. |
| 8,636,718 B2 | 1/2014 | Sela et al. |
| 8,649,880 B1 | 2/2014 | Parker, Jr. |
| 8,700,120 B2 | 4/2014 | Koblish |
| 8,706,193 B2 | 4/2014 | Govari et al. |
| 8,744,599 B2 | 6/2014 | Tegg |
| 8,755,861 B2 | 6/2014 | Harlev et al. |
| 8,771,267 B2 | 7/2014 | Kunis et al. |
| 8,777,929 B2 | 7/2014 | Schneider et al. |
| 8,792,962 B2 | 7/2014 | Esguerra et al. |
| 8,814,824 B2 | 8/2014 | Kauphusman et al. |
| 8,814,825 B2 | 8/2014 | Tegg et al. |
| 8,882,705 B2 | 11/2014 | McDaniel et al. |
| 8,894,610 B2 | 11/2014 | Macnamara et al. |
| 8,979,841 B2 | 3/2015 | Kunis et al. |
| 8,996,091 B2 | 3/2015 | de la Rama et al. |
| 9,017,308 B2 | 4/2015 | Klisch et al. |
| 9,033,917 B2 | 5/2015 | Magana et al. |
| 9,044,245 B2 | 6/2015 | Condie et al. |
| 9,050,010 B2 | 6/2015 | Bui et al. |
| 9,101,733 B2 | 8/2015 | McDaniel |
| 9,204,929 B2 | 12/2015 | Solis |
| 9,216,056 B2 | 12/2015 | Datta et al. |
| 9,247,990 B2 | 2/2016 | Kauphusman et al. |
| 9,326,815 B2 | 5/2016 | Watson |
| 9,339,631 B2 | 5/2016 | Graham et al. |
| 9,433,751 B2 | 9/2016 | Ponzi et al. |
| 9,433,752 B2 | 9/2016 | Jimenez et al. |
| 9,468,495 B2 | 10/2016 | Kunis et al. |
| 9,486,280 B2 | 11/2016 | Koblish et al. |
| 9,486,282 B2 | 11/2016 | Solis |
| 9,522,035 B2 | 12/2016 | Highsmith |
| 9,532,703 B2 | 1/2017 | Huszar et al. |
| 9,539,413 B2 | 1/2017 | Ogle |
| 9,629,675 B2 | 4/2017 | Kleshinski et al. |
| 9,649,158 B2 | 5/2017 | Datta et al. |
| 9,687,166 B2 | 6/2017 | Subramaniam et al. |
| 9,693,733 B2 | 7/2017 | Altmann et al. |
| 9,694,159 B2 | 7/2017 | Schneider et al. |
| 9,694,161 B2 | 7/2017 | Selkee |
| 9,713,418 B2 | 7/2017 | Huszar et al. |
| 9,788,895 B2 | 10/2017 | Solis |
| 9,820,664 B2 | 11/2017 | Hoitink et al. |
| 9,833,608 B2 | 12/2017 | Masson |
| 9,844,645 B2 | 12/2017 | Pai et al. |
| 9,848,795 B2 | 12/2017 | Marecki et al. |
| 9,907,480 B2 | 3/2018 | Basu et al. |
| 9,919,132 B2 | 3/2018 | Tegg et al. |
| 9,949,656 B2 | 4/2018 | Wu et al. |
| 9,986,949 B2 | 6/2018 | Govari et al. |
| 10,004,877 B2 | 6/2018 | Tegg |
| 10,034,637 B2 | 7/2018 | Harlev et al. |
| 10,052,457 B2 | 8/2018 | Nguyen et al. |
| 10,065,019 B2 | 9/2018 | Hamuro et al. |
| 10,099,036 B2 | 10/2018 | Heideman et al. |
| 10,118,022 B2 | 11/2018 | Helgeson et al. |
| 10,136,829 B2 | 11/2018 | Deno et al. |
| 10,143,394 B2 | 12/2018 | Solis |
| 10,285,610 B2 | 5/2019 | Wu |
| 10,322,261 B2 | 6/2019 | Pai et al. |
| 10,362,952 B2 | 7/2019 | Basu et al. |
| 10,362,954 B2 | 7/2019 | de la Rama et al. |
| 10,376,170 B2 | 8/2019 | Quinn et al. |

(56) References Cited

U.S. PATENT DOCUMENTS

| | | | |
|---|---|---|---|
| 10,384,036 B2 | 8/2019 | Romoscanu | |
| 10,398,500 B2 | 9/2019 | Huszar et al. | |
| 10,470,682 B2 | 11/2019 | Deno et al. | |
| 10,478,247 B2 | 11/2019 | Litscher et al. | |
| 10,478,325 B2 | 11/2019 | Syed | |
| 10,506,938 B2 | 12/2019 | Wu et al. | |
| 10,537,259 B2 | 1/2020 | Wu et al. | |
| 10,542,899 B2 | 1/2020 | Wu et al. | |
| 10,556,091 B2 | 2/2020 | Truhler et al. | |
| 10,575,742 B2 | 3/2020 | Wu et al. | |
| 10,575,745 B2 | 3/2020 | Solis | |
| 10,578,737 B2 | 3/2020 | Gliner et al. | |
| 10,595,738 B2 | 3/2020 | Sterrett et al. | |
| 10,595,740 B2 | 3/2020 | Hoitink et al. | |
| 10,602,948 B2 | 3/2020 | Wu et al. | |
| 10,646,692 B2 | 5/2020 | Tegg et al. | |
| 10,653,423 B2 | 5/2020 | Starnes | |
| 10,702,177 B2 | 7/2020 | Aujla | |
| 10,702,677 B2 | 7/2020 | Okamura et al. | |
| 10,737,060 B2 | 8/2020 | Gupta et al. | |
| 10,813,590 B2 | 10/2020 | Ruppersberg | |
| 10,835,712 B2 | 11/2020 | Wada | |
| 10,842,990 B2 | 11/2020 | de la Rama et al. | |
| 10,857,349 B2 | 12/2020 | de la Rama et al. | |
| 10,869,992 B2 | 12/2020 | Pai et al. | |
| 10,898,685 B2 | 1/2021 | Tegg | |
| 10,905,347 B2 | 2/2021 | Fuentes-ortega et al. | |
| 10,912,925 B2 | 2/2021 | Houck | |
| 10,945,626 B2 | 3/2021 | Fuentes-Ortega et al. | |
| 10,946,167 B2 | 3/2021 | Mintz et al. | |
| 10,953,196 B2 | 3/2021 | Raab et al. | |
| 10,959,636 B2 | 3/2021 | Dahlen et al. | |
| 10,966,623 B2 | 4/2021 | Wu et al. | |
| 10,966,753 B2 | 4/2021 | Coyle et al. | |
| 10,967,150 B2 | 4/2021 | Helgeson et al. | |
| 10,987,045 B2 | 4/2021 | Basu et al. | |
| 11,033,715 B2 | 6/2021 | Beeckler et al. | |
| 11,039,772 B2 | 6/2021 | Wu et al. | |
| 11,039,773 B2 | 6/2021 | Sterrett et al. | |
| 11,077,298 B2 | 8/2021 | Waldhauser et al. | |
| 11,083,400 B2 | 8/2021 | Hoitink et al. | |
| 11,116,436 B2 | 9/2021 | Wu et al. | |
| 11,116,476 B2 | 9/2021 | Buesseler et al. | |
| 11,116,942 B2 | 9/2021 | Beeckler et al. | |
| 11,123,051 B2 | 9/2021 | Van Der Linde et al. | |
| 11,141,568 B2 | 10/2021 | Hsueh et al. | |
| 11,160,482 B2 | 11/2021 | Solis | |
| 11,172,858 B2 | 11/2021 | Olson et al. | |
| 11,272,886 B2 | 3/2022 | Harlev et al. | |
| 11,382,690 B2 | 7/2022 | Smith et al. | |
| 11,382,743 B2 | 7/2022 | Marchand et al. | |
| 11,383,078 B2 | 7/2022 | de la Rama et al. | |
| 11,419,673 B2 | 8/2022 | Kauphusman et al. | |
| 11,426,111 B2 | 8/2022 | Olson | |
| 11,433,220 B2 | 9/2022 | Oliverius et al. | |
| 11,439,460 B2 | 9/2022 | Sliwa et al. | |
| 11,446,470 B2 | 9/2022 | Castelli et al. | |
| 11,446,471 B2 | 9/2022 | Grunewald | |
| 11,478,299 B2 | 10/2022 | Webster et al. | |
| 11,484,690 B2 | 11/2022 | Tegg et al. | |
| 11,491,311 B2 | 11/2022 | Selkee | |
| 11,504,205 B2 | 11/2022 | Brucker et al. | |
| 11,511,078 B2 | 11/2022 | Gonzalez | |
| 11,517,715 B2 | 12/2022 | Govari | |
| 11,517,716 B2 | 12/2022 | Nguyen et al. | |
| 11,523,748 B2 | 12/2022 | Esguerra Wilczynski et al. | |
| 11,540,878 B2 | 1/2023 | Fuentes-Ortega et al. | |
| 11,547,437 B2 | 1/2023 | Zarembinski | |
| 11,559,663 B2 | 1/2023 | Hannon et al. | |
| 11,583,334 B2 | 2/2023 | Caples et al. | |
| 11,583,658 B2 | 2/2023 | Yang et al. | |
| 11,602,630 B2 | 3/2023 | Vetter et al. | |
| 11,617,616 B2 | 4/2023 | Clark et al. | |
| 11,617,859 B2 | 4/2023 | Hsueh et al. | |
| 11,617,861 B2 | 4/2023 | Pai et al. | |
| 11,622,806 B2 | 4/2023 | Romoscanu | |
| 11,628,009 B2 | 4/2023 | Aujla | |
| 11,660,119 B2 | 5/2023 | Hassett | |
| 11,672,947 B2 | 6/2023 | Tegg et al. | |
| 11,684,473 B2 | 6/2023 | Righini et al. | |
| 11,779,770 B2 | 10/2023 | Botzer | |
| 11,786,301 B2 | 10/2023 | Olson | |
| 11,806,152 B2 | 11/2023 | Zeidan et al. | |
| 11,813,410 B2 | 11/2023 | Olson et al. | |
| 11,832,965 B2 | 12/2023 | Wang | |
| 11,850,051 B2 | 12/2023 | Selkee et al. | |
| 11,857,250 B2 | 1/2024 | Corvi et al. | |
| 11,896,819 B2 | 2/2024 | Rosa et al. | |
| 11,938,316 B2 | 3/2024 | Feler et al. | |
| 2002/0165484 A1 | 11/2002 | Bowe et al. | |
| 2005/0159741 A1 | 7/2005 | Paul et al. | |
| 2007/0060833 A1 | 3/2007 | Hauck | |
| 2009/0198300 A1 | 8/2009 | Zhang et al. | |
| 2011/0118726 A1 | 5/2011 | de la Rama et al. | |
| 2012/0265054 A1 | 10/2012 | Olson | |
| 2012/0271302 A1 | 10/2012 | Behl et al. | |
| 2012/0296232 A1 | 11/2012 | Ng | |
| 2013/0066193 A1 | 3/2013 | Olson et al. | |
| 2013/0253504 A1 | 9/2013 | Fang | |
| 2013/0274582 A1 | 10/2013 | Afonso et al. | |
| 2014/0100639 A1 | 4/2014 | Lee et al. | |
| 2014/0200639 A1 | 7/2014 | de la Rama | |
| 2014/0269602 A1 | 9/2014 | Kawagishi | |
| 2014/0296846 A1 | 10/2014 | Huszar et al. | |
| 2014/0296902 A1 | 10/2014 | Huszar et al. | |
| 2014/0316496 A1 | 10/2014 | Masson et al. | |
| 2014/0336636 A1 | 11/2014 | Huszar et al. | |
| 2014/0350564 A1 | 11/2014 | Huszar et al. | |
| 2015/0001191 A1 | 1/2015 | Lee et al. | |
| 2015/0105645 A1 | 4/2015 | Subramaniam et al. | |
| 2015/0141785 A1 | 5/2015 | Hayam et al. | |
| 2015/0159741 A1 | 6/2015 | Versteyhe et al. | |
| 2015/0342700 A1 | 12/2015 | Govari et al. | |
| 2015/0351652 A1 | 12/2015 | Marecki et al. | |
| 2016/0143588 A1 | 5/2016 | Hoitink et al. | |
| 2016/0213423 A1 | 7/2016 | Kauphusman et al. | |
| 2016/0213916 A1 | 7/2016 | de la Rama | |
| 2016/0278851 A1 | 9/2016 | Mannion et al. | |
| 2016/0317094 A1 | 11/2016 | Byrd et al. | |
| 2016/0331471 A1 | 11/2016 | Deno et al. | |
| 2016/0331933 A1 | 11/2016 | Knutsen | |
| 2016/0374582 A1 | 12/2016 | Wu et al. | |
| 2016/0374753 A1 | 12/2016 | Wu et al. | |
| 2017/0000365 A1* | 1/2017 | Wu | A61B 5/6858 |
| 2017/0042449 A1 | 2/2017 | Deno et al. | |
| 2017/0042473 A1* | 2/2017 | Quinn | A61B 5/6858 |
| 2017/0049348 A1 | 2/2017 | Deno et al. | |
| 2017/0112404 A1 | 4/2017 | de la Rama et al. | |
| 2017/0112405 A1 | 4/2017 | Sterrett et al. | |
| 2017/0273738 A1 | 9/2017 | Wu | |
| 2017/0319269 A1 | 11/2017 | Oliverius et al. | |
| 2017/0367756 A1 | 12/2017 | Sliwa et al. | |
| 2018/0042667 A1 | 2/2018 | Pappone et al. | |
| 2018/0056038 A1 | 3/2018 | Aujla | |
| 2018/0070845 A1 | 3/2018 | Hoitink et al. | |
| 2018/0085064 A1 | 3/2018 | Auerbach et al. | |
| 2018/0116539 A1* | 5/2018 | Olson | A61B 5/287 |
| 2018/0161093 A1 | 6/2018 | Basu et al. | |
| 2018/0193089 A1 | 7/2018 | Wu | |
| 2018/0199981 A1* | 7/2018 | Sheets | A61B 18/02 |
| 2018/0229030 A1 | 8/2018 | Dubuclet et al. | |
| 2018/0235496 A1 | 8/2018 | Wu et al. | |
| 2018/0296111 A1 | 10/2018 | Deno et al. | |
| 2018/0303361 A1 | 10/2018 | Wu et al. | |
| 2018/0335519 A1 | 11/2018 | Gliner et al. | |
| 2018/0361118 A1* | 12/2018 | Cully | A61M 25/0084 |
| 2018/0369574 A1 | 12/2018 | Dubuclet et al. | |
| 2019/0009052 A1 | 1/2019 | Oliverius et al. | |
| 2019/0125378 A1 | 5/2019 | Shelton, IV et al. | |
| 2019/0175043 A1 | 6/2019 | Wu et al. | |
| 2019/0192826 A1 | 6/2019 | Wada | |
| 2019/0239812 A1 | 8/2019 | Botzer et al. | |
| 2019/0328459 A1* | 10/2019 | Katz | A61B 5/6843 |
| 2020/0054391 A1 | 2/2020 | Litscher et al. | |

(56) References Cited

U.S. PATENT DOCUMENTS

| | | |
|---|---|---|
| 2020/0077908 A1 | 3/2020 | Hagfors et al. |
| 2020/0077912 A1 | 3/2020 | Wu et al. |
| 2020/0113469 A1 | 4/2020 | Sahadevan et al. |
| 2020/0121894 A1 | 4/2020 | Prabhu et al. |
| 2020/0138378 A1 | 5/2020 | de la Rama et al. |
| 2020/0155021 A1 | 5/2020 | Wu et al. |
| 2020/0205737 A1 | 7/2020 | Beeckler |
| 2020/0214635 A1 | 7/2020 | Dahlen et al. |
| 2020/0221966 A1 | 7/2020 | Wu et al. |
| 2020/0229726 A1 | 7/2020 | Sterrett et al. |
| 2020/0229727 A1 | 7/2020 | Hoitink et al. |
| 2020/0253496 A1 | 8/2020 | Deno et al. |
| 2020/0305744 A1 | 10/2020 | Weerakoon et al. |
| 2020/0329989 A1 | 10/2020 | Aujla |
| 2020/0345262 A1 | 11/2020 | Selkee et al. |
| 2020/0360657 A1 | 11/2020 | Ganske |
| 2020/0398026 A1 | 12/2020 | Castelli et al. |
| 2020/0405166 A1 | 12/2020 | Wu et al. |
| 2021/0015551 A1 | 1/2021 | Fuentes-ortega et al. |
| 2021/0038860 A1 | 2/2021 | Mintz et al. |
| 2021/0059745 A1 | 3/2021 | Highsmith |
| 2021/0068693 A1 | 3/2021 | Fuentes-ortega et al. |
| 2021/0077183 A1 | 3/2021 | Shubhayu et al. |
| 2021/0085920 A1 | 3/2021 | Roberts et al. |
| 2021/0085921 A1 | 3/2021 | Roberts et al. |
| 2021/0145342 A1 | 5/2021 | Wang |
| 2021/0153932 A1 | 5/2021 | Voth et al. |
| 2021/0187246 A1 | 6/2021 | Houck |
| 2021/0204871 A1 | 7/2021 | Goedeke et al. |
| 2021/0228136 A1 | 7/2021 | Fuentes-ortega et al. |
| 2021/0228137 A1 | 7/2021 | Aujla |
| 2021/0267693 A1 | 9/2021 | Deno et al. |
| 2021/0268234 A1 | 9/2021 | Helgeson et al. |
| 2021/0298656 A1 | 9/2021 | Wu et al. |
| 2021/0361216 A1 | 11/2021 | Hoitink et al. |
| 2021/0361428 A1 | 11/2021 | Dixon |
| 2021/0369132 A1 | 12/2021 | Van Niekerk et al. |
| 2021/0369338 A1 | 12/2021 | Govari et al. |
| 2021/0369339 A1 | 12/2021 | Salazar et al. |
| 2021/0370022 A1 | 12/2021 | Bean et al. |
| 2021/0401345 A1 | 12/2021 | Wu et al. |
| 2021/0402148 A1 | 12/2021 | Beeckler et al. |
| 2022/0023594 A1 | 1/2022 | Pai |
| 2022/0054066 A1 | 2/2022 | Solis |
| 2022/0061727 A1 | 3/2022 | Olson et al. |
| 2022/0079496 A1 | 3/2022 | Squires et al. |
| 2022/0225941 A1 | 7/2022 | Smaill et al. |
| 2022/0273913 A1 | 9/2022 | Worley et al. |
| 2022/0331553 A1 | 10/2022 | Strom et al. |
| 2022/0354568 A1 | 11/2022 | Pappone et al. |
| 2022/0370792 A1 | 11/2022 | de la Rama et al. |
| 2022/0387012 A1 | 12/2022 | Nunan |
| 2022/0401032 A1 | 12/2022 | Govari et al. |
| 2022/0401693 A1 | 12/2022 | Oliverius et al. |
| 2022/0409860 A1 | 12/2022 | Castelli et al. |
| 2023/0000415 A1 | 1/2023 | Olson |
| 2023/0024690 A1 | 1/2023 | Cohen et al. |
| 2023/0033444 A1 | 2/2023 | Knighton et al. |
| 2023/0043978 A1 | 2/2023 | Govari |
| 2023/0055089 A1 | 2/2023 | Govari et al. |
| 2023/0078216 A1 | 3/2023 | Govari |
| 2023/0083615 A1 | 3/2023 | Nguyen et al. |
| 2023/0084626 A1 | 3/2023 | Grunewald |
| 2023/0114222 A1 | 4/2023 | Esguerra Wilczynski et al. |
| 2023/0121397 A1 | 4/2023 | Oliverius et al. |
| 2023/0123266 A1 | 4/2023 | Castelli et al. |
| 2023/0149675 A1 | 5/2023 | Leung et al. |
| 2023/0190198 A1 | 6/2023 | Pederson et al. |
| 2023/0190369 A1 | 6/2023 | Caples et al. |
| 2023/0284956 A1 | 9/2023 | Wu et al. |
| 2023/0329618 A1 | 10/2023 | Wu et al. |
| 2023/0329784 A1 | 10/2023 | Stewart et al. |
| 2023/0404657 A1 | 12/2023 | Olson |
| 2023/0405338 A1 | 12/2023 | Botzer |
| 2024/0033470 A1 | 2/2024 | Olson et al. |
| 2024/0057939 A1 | 2/2024 | Wang |
| 2024/0081712 A1 | 3/2024 | Selkee et al. |
| 2024/0081905 A1 | 3/2024 | Corvi et al. |

FOREIGN PATENT DOCUMENTS

| | | |
|---|---|---|
| AU | 2016204353 A1 | 1/2017 |
| AU | 2016204355 A1 | 1/2017 |
| CA | 2934209 A1 | 12/2016 |
| CA | 2934211 A1 | 12/2016 |
| CA | 2934214 A1 | 12/2016 |
| CN | 101797181 A | 8/2010 |
| CN | 101927053 B | 1/2015 |
| CN | 103157168 B | 4/2015 |
| CN | 105960201 A | 9/2016 |
| CN | 106859765 A | 6/2017 |
| CN | 106901831 A | 6/2017 |
| CN | 206880930 U | 1/2018 |
| CN | 104958824 B | 12/2018 |
| CN | 104434083 B | 4/2019 |
| CN | 104968261 B | 5/2019 |
| CN | 105592778 B | 7/2019 |
| CN | 105960200 B | 8/2019 |
| CN | 105451680 B | 10/2019 |
| CN | 110536646 A | 12/2019 |
| CN | 110604860 A | 12/2019 |
| CN | 105960201 B | 3/2020 |
| CN | 111225627 A | 6/2020 |
| CN | 111227929 A | 6/2020 |
| CN | 111374755 A | 7/2020 |
| CN | 111432739 A | 7/2020 |
| CN | 111657866 A | 9/2020 |
| CN | 111839499 A | 10/2020 |
| CN | 106264715 B | 11/2020 |
| CN | 106264716 B | 11/2020 |
| CN | 112040861 A | 12/2020 |
| CN | 106308790 B | 6/2021 |
| CN | 107529958 B | 7/2021 |
| CN | 109310469 B | 7/2021 |
| CN | 213665310 U | 7/2021 |
| CN | 109641121 B | 9/2021 |
| CN | 109952123 B | 9/2021 |
| CN | 110545874 B | 9/2021 |
| CN | 110559544 B | 9/2021 |
| CN | 113425304 A | 9/2021 |
| CN | 105615994 B | 10/2021 |
| CN | 109963610 B | 11/2021 |
| CN | 113939327 A | 1/2022 |
| CN | 108289709 B | 3/2022 |
| CN | 114126522 A | 3/2022 |
| CN | 114375211 A | 4/2022 |
| CN | 111246907 B | 7/2022 |
| CN | 114727815 A | 7/2022 |
| CN | 114828745 A | 7/2022 |
| CN | 107773300 B | 8/2022 |
| CN | 108567424 B | 8/2022 |
| CN | 106859638 B | 10/2022 |
| CN | 108283520 B | 10/2022 |
| CN | 110547865 B | 10/2022 |
| CN | 107343816 B | 11/2022 |
| CN | 115281680 A | 11/2022 |
| CN | 115379873 A | 11/2022 |
| CN | 115426941 A | 12/2022 |
| CN | 115444549 A | 12/2022 |
| CN | 115461007 A | 12/2022 |
| CN | 115666700 A | 1/2023 |
| CN | 107343784 B | 2/2023 |
| CN | 115697221 A | 2/2023 |
| CN | 115768346 A | 3/2023 |
| CN | 110520067 B | 5/2023 |
| CN | 111225627 B | 5/2023 |
| CN | 116137804 A | 5/2023 |
| CN | 116157084 A | 5/2023 |
| CN | 116157174 A | 5/2023 |
| CN | 116158839 A | 5/2023 |
| CN | 106419897 B | 6/2023 |
| CN | 111065350 B | 6/2023 |
| CN | 116234511 A | 6/2023 |
| CN | 109259854 B | 10/2023 |

(56) References Cited

FOREIGN PATENT DOCUMENTS

| | | |
|---|---|---|
| CN | 111836579 B | 3/2024 |
| CN | 112704546 B | 3/2024 |
| EP | 0889744 B1 | 1/2004 |
| EP | 1254641 B1 | 11/2008 |
| EP | 1690564 B1 | 4/2009 |
| EP | 1723981 B1 | 8/2010 |
| EP | 2135634 B1 | 10/2011 |
| EP | 2018203 B1 | 6/2012 |
| EP | 1814450 B1 | 1/2013 |
| EP | 2269532 B1 | 3/2013 |
| EP | 2664295 A1 | 11/2013 |
| EP | 2604306 B1 | 1/2014 |
| EP | 2732843 A1 | 5/2014 |
| EP | 2747680 A2 | 7/2014 |
| EP | 2752153 A1 | 7/2014 |
| EP | 2907462 A1 | 8/2015 |
| EP | 2915555 A1 | 9/2015 |
| EP | 1968679 B1 | 9/2016 |
| EP | 2241279 B1 | 9/2016 |
| EP | 2796103 B1 | 2/2017 |
| EP | 3222209 A1 | 9/2017 |
| EP | 2792322 B1 | 10/2017 |
| EP | 2792323 B1 | 10/2017 |
| EP | 3115076 A4 | 10/2017 |
| EP | 3117863 A4 | 10/2017 |
| EP | 3030182 B1 | 1/2018 |
| EP | 3287092 A1 | 2/2018 |
| EP | 3111871 B1 | 3/2018 |
| EP | 3111872 B1 | 4/2018 |
| EP | 3057488 B1 | 5/2018 |
| EP | 2848226 B1 | 7/2018 |
| EP | 3345540 A1 | 7/2018 |
| EP | 3363397 A1 | 8/2018 |
| EP | 3391928 A1 | 10/2018 |
| EP | 3122276 B1 | 11/2018 |
| EP | 3398549 A1 | 11/2018 |
| EP | 3403571 A1 | 11/2018 |
| EP | 1759668 B1 | 12/2018 |
| EP | 3037122 B1 | 12/2018 |
| EP | 2234537 B1 | 1/2019 |
| EP | 2569040 B1 | 2/2019 |
| EP | 3023052 B1 | 3/2019 |
| EP | 3073908 B1 | 4/2019 |
| EP | 3466363 A1 | 4/2019 |
| EP | 2550989 B1 | 6/2019 |
| EP | 3512589 A1 | 7/2019 |
| EP | 3512590 A1 | 7/2019 |
| EP | 3527125 A1 | 8/2019 |
| EP | 3531903 A1 | 9/2019 |
| EP | 3581229 A1 | 12/2019 |
| EP | 3434218 B1 | 2/2020 |
| EP | 2908723 B1 | 3/2020 |
| EP | 3335658 B1 | 4/2020 |
| EP | 3073907 B1 | 6/2020 |
| EP | 3673851 A1 | 7/2020 |
| EP | 3114987 B1 | 8/2020 |
| EP | 3178516 B1 | 9/2020 |
| EP | 3708104 A1 | 9/2020 |
| EP | 3711662 A1 | 9/2020 |
| EP | 3721796 A1 | 10/2020 |
| EP | 3733103 A1 | 11/2020 |
| EP | 3738508 A1 | 11/2020 |
| EP | 3738509 A1 | 11/2020 |
| EP | 3340916 B1 | 12/2020 |
| EP | 3579908 B1 | 12/2020 |
| EP | 3749174 A1 | 12/2020 |
| EP | 3749192 A1 | 12/2020 |
| EP | 3749195 A1 | 12/2020 |
| EP | 3750475 A1 | 12/2020 |
| EP | 3768185 A1 | 1/2021 |
| EP | 2155301 B1 | 4/2021 |
| EP | 3432820 B1 | 4/2021 |
| EP | 3476331 B1 | 5/2021 |
| EP | 3579758 B1 | 5/2021 |
| EP | 2809254 B1 | 6/2021 |
| EP | 3508245 B1 | 7/2021 |
| EP | 3858277 A1 | 8/2021 |
| EP | 3892221 A1 | 10/2021 |
| EP | 3902461 A1 | 11/2021 |
| EP | 3915477 A1 | 12/2021 |
| EP | 3915501 A1 | 12/2021 |
| EP | 3919014 A1 | 12/2021 |
| EP | 3932343 A4 | 1/2022 |
| EP | 3791820 B9 | 4/2022 |
| EP | 3986520 A1 | 4/2022 |
| EP | 4000506 A1 | 5/2022 |
| EP | 3153124 B1 | 7/2022 |
| EP | 3860447 A4 | 7/2022 |
| EP | 4025112 A1 | 7/2022 |
| EP | 4031007 A1 | 7/2022 |
| EP | 4031044 A2 | 7/2022 |
| EP | 4039215 A1 | 8/2022 |
| EP | 3363397 B1 | 9/2022 |
| EP | 3673944 B1 | 9/2022 |
| EP | 3915501 B1 | 9/2022 |
| EP | 3949848 A4 | 9/2022 |
| EP | 4076193 A1 | 10/2022 |
| EP | 4078255 A1 | 10/2022 |
| EP | 3609414 B1 | 11/2022 |
| EP | 4093274 A1 | 11/2022 |
| EP | 4096545 A1 | 12/2022 |
| EP | 4101372 A1 | 12/2022 |
| EP | 4106625 A1 | 12/2022 |
| EP | 4106853 A2 | 12/2022 |
| EP | 2844193 B1 | 1/2023 |
| EP | 3100696 B1 | 1/2023 |
| EP | 3166524 B1 | 1/2023 |
| EP | 3946123 A4 | 1/2023 |
| EP | 4115936 A1 | 1/2023 |
| EP | 4120963 A1 | 1/2023 |
| EP | 4122414 A1 | 1/2023 |
| EP | 4134032 A1 | 2/2023 |
| EP | 3115076 B1 | 3/2023 |
| EP | 3658054 B1 | 3/2023 |
| EP | 4157420 A1 | 4/2023 |
| EP | 4159124 A1 | 4/2023 |
| EP | 4164519 A1 | 4/2023 |
| EP | 4179991 A1 | 5/2023 |
| EP | 4181810 A1 | 5/2023 |
| EP | 4185224 A1 | 5/2023 |
| EP | 4185225 A1 | 5/2023 |
| EP | 2803329 B1 | 6/2023 |
| EP | 3015064 B1 | 6/2023 |
| EP | 3141183 B1 | 6/2023 |
| EP | 3398549 B1 | 6/2023 |
| EP | 3768185 B1 | 6/2023 |
| EP | 4190232 A1 | 6/2023 |
| EP | 4218579 A1 | 8/2023 |
| EP | 2816966 B1 | 10/2023 |
| EP | 3113671 B1 | 10/2023 |
| EP | 3681427 B1 | 10/2023 |
| EP | 3738509 B1 | 10/2023 |
| EP | 3749195 B1 | 10/2023 |
| EP | 3209234 B1 | 11/2023 |
| EP | 3527125 B1 | 11/2023 |
| EP | 3721796 B1 | 11/2023 |
| EP | 3731747 B1 | 11/2023 |
| EP | 3998935 B1 | 11/2023 |
| EP | 4233699 A3 | 11/2023 |
| EP | 4272631 A2 | 11/2023 |
| EP | 3192442 B1 | 1/2024 |
| EP | 3892221 B1 | 1/2024 |
| EP | 4298995 A2 | 1/2024 |
| EP | 3738508 B1 | 2/2024 |
| EP | 4159124 B1 | 4/2024 |
| IL | 246415 B | 12/2019 |
| IN | 201614021431 A | 12/2016 |
| IN | 201614021432 A | 12/2016 |
| IN | 201614021450 A | 12/2016 |
| JP | 4545384 B2 | 7/2010 |
| JP | 4887810 B2 | 2/2012 |
| JP | 4940332 B2 | 3/2012 |
| JP | 2012055602 A | 3/2012 |
| JP | 2012200509 A | 10/2012 |

(56) References Cited

FOREIGN PATENT DOCUMENTS

| | | |
|---|---|---|
| JP | 5154031 B2 | 2/2013 |
| JP | 5193190 B2 | 5/2013 |
| JP | 5372314 B2 | 12/2013 |
| JP | 2014014713 A | 1/2014 |
| JP | 5550150 B2 | 5/2014 |
| JP | 5762697 B2 | 6/2015 |
| JP | 5856712 B2 | 2/2016 |
| JP | 5908270 B2 | 4/2016 |
| JP | 5944331 B2 | 7/2016 |
| JP | 2016144642 A | 8/2016 |
| JP | 6050522 B2 | 12/2016 |
| JP | 6059737 B2 | 12/2016 |
| JP | 2017012750 A | 1/2017 |
| JP | 2017012755 A | 1/2017 |
| JP | 2017038919 A | 2/2017 |
| JP | 2017051211 A | 3/2017 |
| JP | 2017104552 A | 6/2017 |
| JP | 6246742 B2 | 12/2017 |
| JP | 6342524 B2 | 6/2018 |
| JP | 6434495 B2 | 12/2018 |
| JP | 6445509 B2 | 12/2018 |
| JP | 6445742 B1 | 12/2018 |
| JP | 6466114 B2 | 2/2019 |
| JP | 6515084 B2 | 5/2019 |
| JP | 6528010 B1 | 6/2019 |
| JP | 2019516455 A | 6/2019 |
| JP | 6655655 B2 | 2/2020 |
| JP | 2020108766 A | 7/2020 |
| JP | 6776021 B2 | 10/2020 |
| JP | 6776025 B2 | 10/2020 |
| JP | 6786275 B2 | 11/2020 |
| JP | 6821812 B2 | 1/2021 |
| JP | 2021007772 A | 1/2021 |
| JP | 2021501011 A | 1/2021 |
| JP | 6843502 B2 | 3/2021 |
| JP | 2021069921 A | 5/2021 |
| JP | 6894004 B2 | 6/2021 |
| JP | 6920312 B2 | 8/2021 |
| JP | 6926306 B2 | 8/2021 |
| JP | 6932484 B2 | 8/2021 |
| JP | 6936872 B2 | 9/2021 |
| JP | 2021523755 A | 9/2021 |
| JP | 6980386 B2 | 12/2021 |
| JP | 2022020838 A | 2/2022 |
| JP | 7101228 B2 | 7/2022 |
| JP | 7106301 B2 | 7/2022 |
| JP | 7135202 B2 | 9/2022 |
| JP | 2022540496 A | 9/2022 |
| JP | 2022546719 A | 11/2022 |
| JP | 2022548944 A | 11/2022 |
| JP | 2023002720 A | 1/2023 |
| JP | 2023501756 A | 1/2023 |
| JP | 7220242 B2 | 2/2023 |
| JP | 7230168 B2 | 2/2023 |
| JP | 2023506505 A | 2/2023 |
| JP | 2023507412 A | 2/2023 |
| JP | 7242665 B2 | 3/2023 |
| JP | 7242816 B2 | 3/2023 |
| JP | 7246319 B2 | 3/2023 |
| JP | 2023027202 A | 3/2023 |
| JP | 2023033335 A | 3/2023 |
| JP | 7256621 B2 | 4/2023 |
| JP | 7262919 B2 | 4/2023 |
| JP | 2023515798 A | 4/2023 |
| JP | 2023517284 A | 4/2023 |
| JP | 7275333 B2 | 5/2023 |
| JP | 7282759 B2 | 5/2023 |
| JP | 2023519039 A | 5/2023 |
| JP | 7292822 B2 | 6/2023 |
| JP | 2023526907 A | 6/2023 |
| JP | 2023139173 A | 10/2023 |
| JP | 7391562 B2 | 11/2023 |
| JP | 7394766 B2 | 11/2023 |
| JP | 7400050 B2 | 12/2023 |
| JP | 7423550 B2 | 1/2024 |
| JP | 2024012693 A | 1/2024 |
| RU | 2016124794 A | 12/2017 |
| RU | 2016124801 A | 12/2017 |
| RU | 2016125763 A | 1/2018 |
| WO | 9843530 A1 | 10/1998 |
| WO | 0168178 A1 | 9/2001 |
| WO | 2008091197 A1 | 7/2008 |
| WO | 2014/113612 A1 | 7/2014 |
| WO | 2015057521 A1 | 4/2015 |
| WO | 2015095577 A1 | 6/2015 |
| WO | 2015130824 A1 | 9/2015 |
| WO | 2016001015 A1 | 1/2016 |
| WO | 2017098198 A1 | 6/2017 |
| WO | 2014/141113 A2 | 9/2017 |
| WO | 2018053148 A1 | 3/2018 |
| WO | 2018053164 A1 | 3/2018 |
| WO | 2018136741 A1 | 7/2018 |
| WO | 2019108664 A2 | 6/2019 |
| WO | 2019195439 A1 | 10/2019 |
| WO | 2019226640 A1 | 11/2019 |
| WO | 2021053482 A1 | 3/2021 |
| WO | 2021053648 A1 | 3/2021 |
| WO | 2021061198 A1 | 4/2021 |
| WO | 2021242852 A1 | 12/2021 |

\* cited by examiner

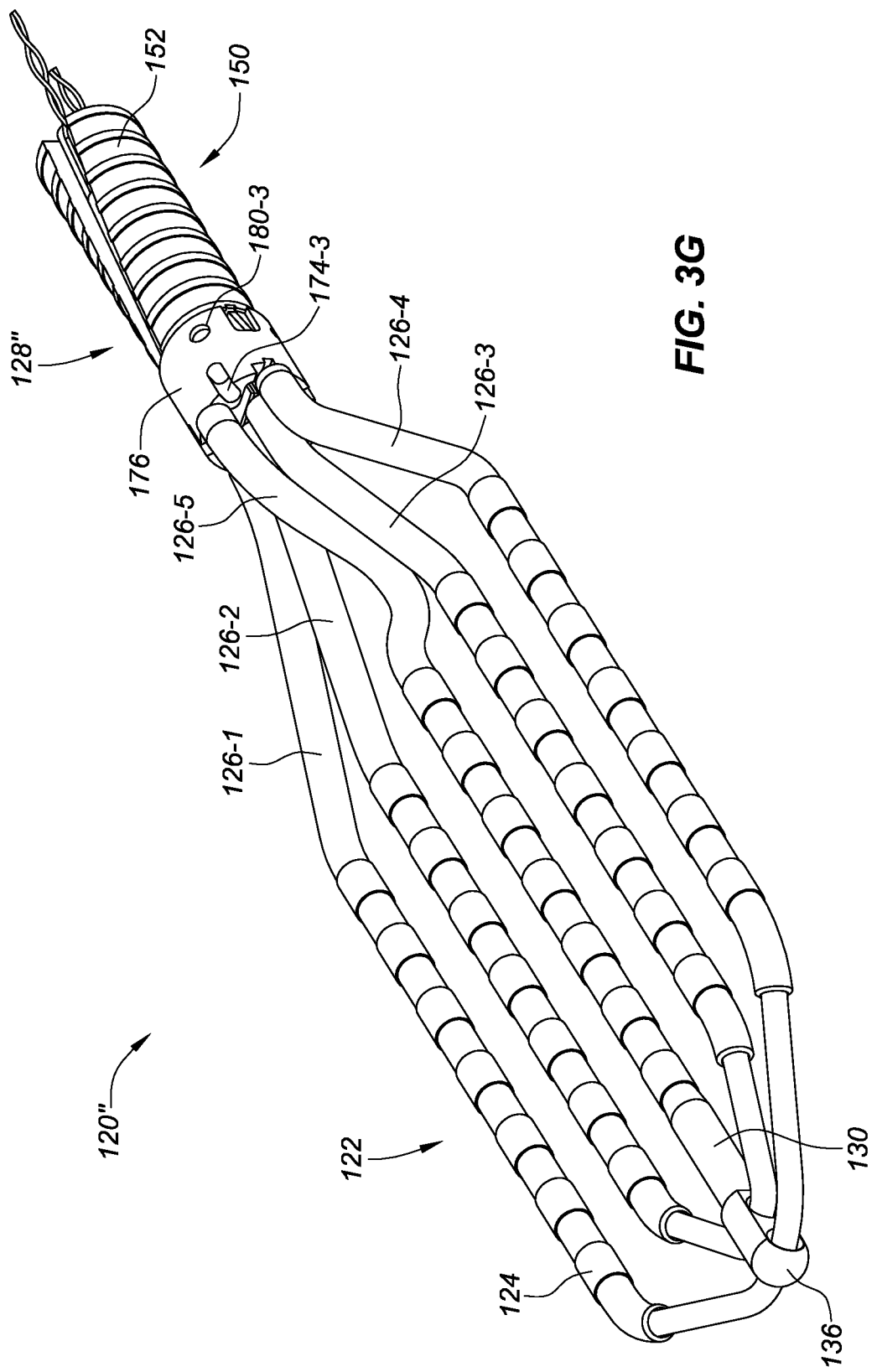

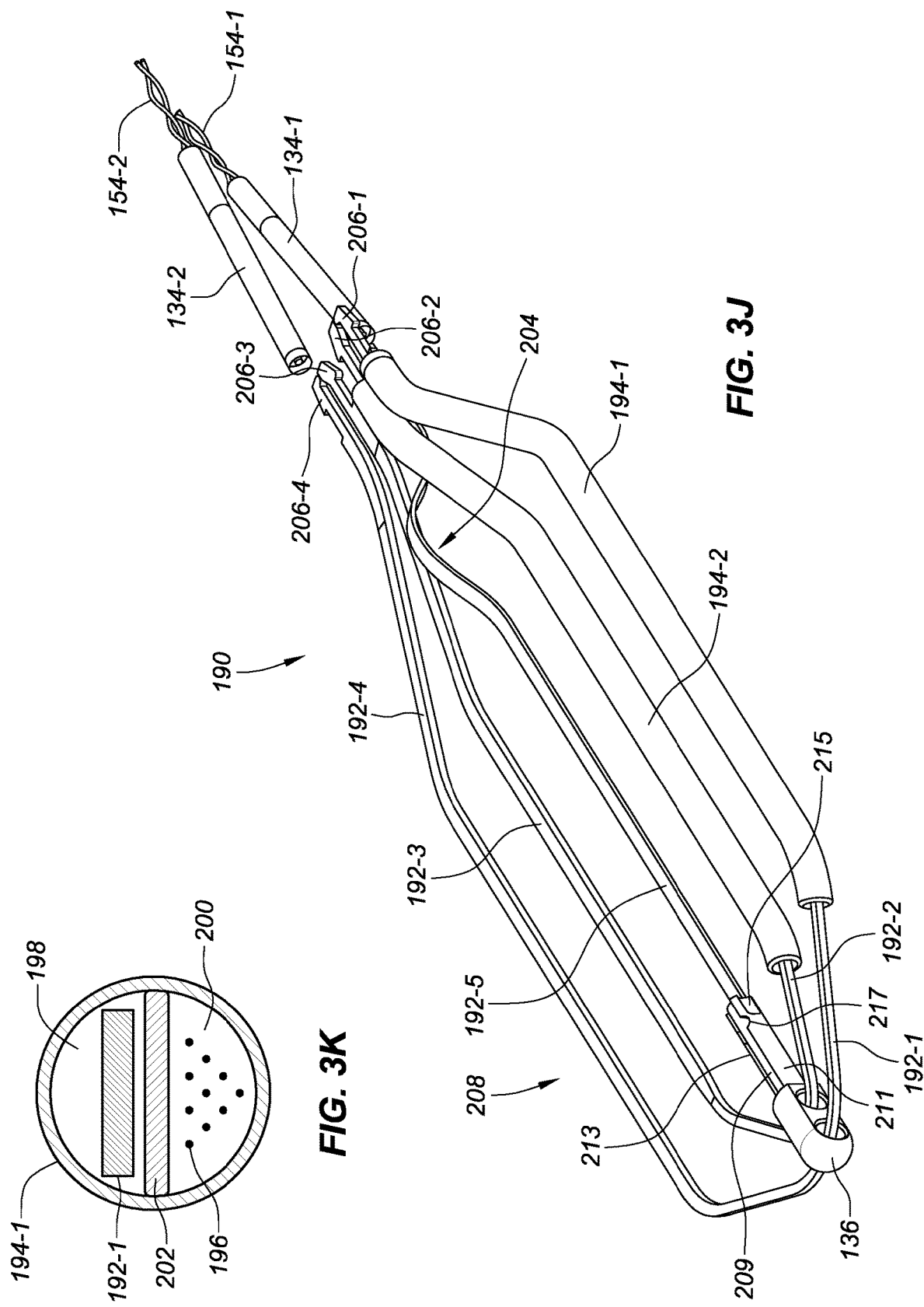

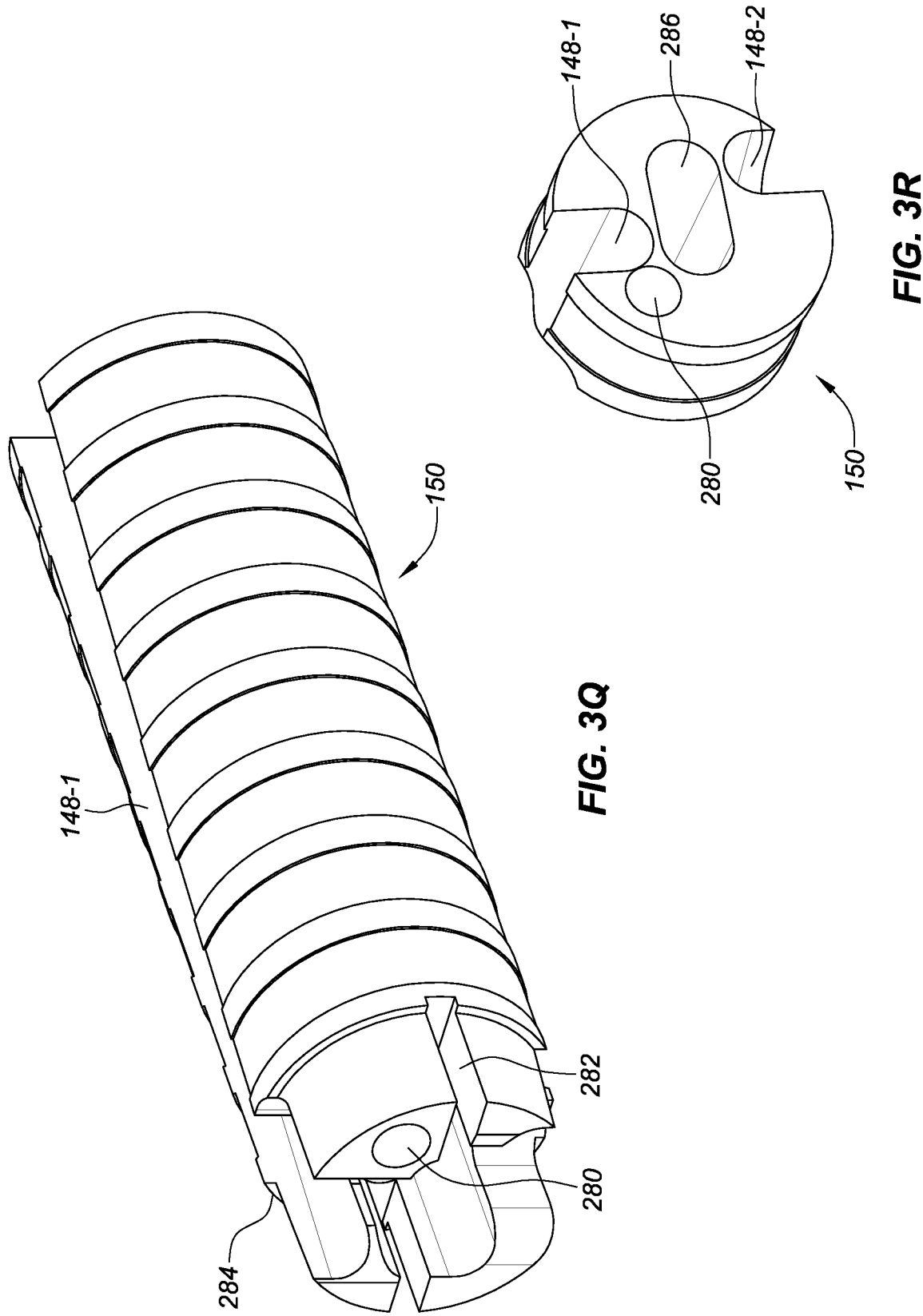

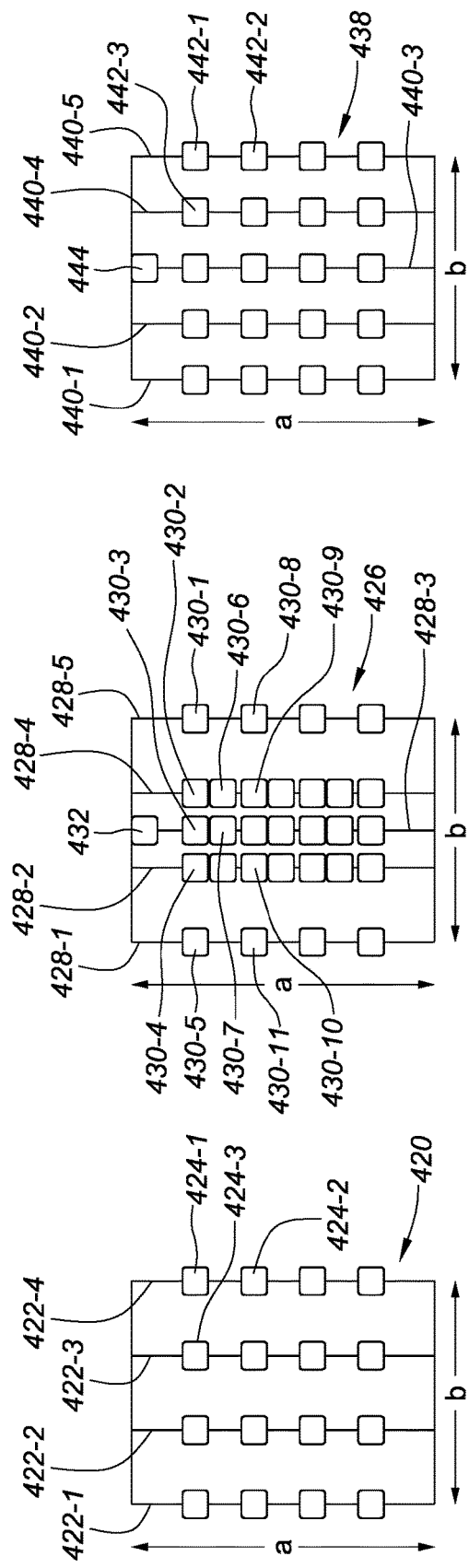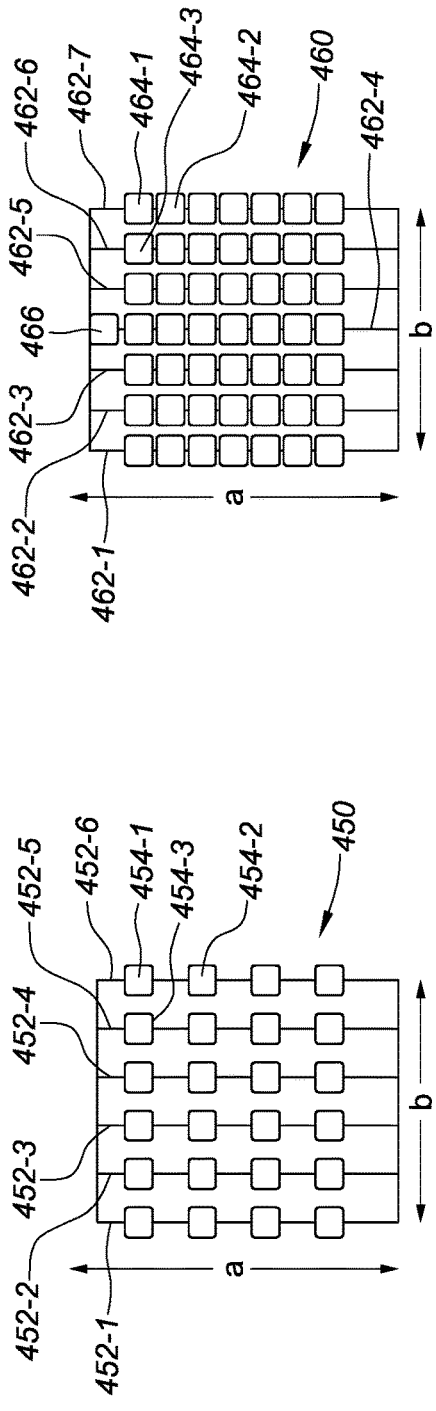
FIG. 8A
FIG. 8B
FIG. 8C
FIG. 8D
FIG. 8E

HIGH-DENSITY ELECTRODE CATHETERS WITH MAGNETIC POSITION TRACKING

PRIORITY CLAIM

This application claims priority to U.S. provisional patent application No. 63/067,284, filed 18 Aug. 2020, which is hereby incorporated by reference as though fully set forth herein.

A. FIELD OF THE DISCLOSURE

This disclosure relates to high-density electrode catheters with magnetic position tracking.

B. BACKGROUND ART

Catheters have been used for cardiac medical procedures for many years. Catheters can be used, for example, to diagnose and treat cardiac arrhythmias, while positioned at a specific location within a body that is otherwise inaccessible without a more invasive procedure.

Conventional mapping catheters may include, for example, a plurality of adjacent ring electrodes encircling the longitudinal axis of the catheter, which can be constructed from platinum or some other metal. These ring electrodes are relatively rigid. Similarly, conventional ablation catheters may comprise a relatively rigid tip electrode for delivering therapy (e.g., delivering RF ablation energy) and may also include a plurality of adjacent ring electrodes. It can be difficult to maintain good electrical contact with cardiac tissue when using these conventional catheters and their relatively rigid (or nonconforming), metallic electrodes, especially when sharp gradients and undulations are present.

Whether mapping or forming lesions in a heart, the beating of the heart, especially if erratic or irregular, complicates matters, making it difficult to keep adequate contact between electrodes and tissue for a sufficient length of time. These problems are exacerbated on contoured or trabeculated surfaces. If the contact between the electrodes and the tissue cannot be sufficiently maintained, quality lesions or accurate mapping are unlikely to result.

The foregoing discussion is intended only to illustrate the present field and should not be taken as a disavowal of claim scope.

BRIEF SUMMARY

Various embodiments of the present disclosure can include a high-density electrode catheter. In some embodiments, the high-density electrode catheter can include a catheter shaft including a proximal end and a distal end, the catheter shaft defining a catheter shaft longitudinal axis. In some embodiments, the high-density electrode catheter can include a shaft magnetic position sensor disposed along a distal portion of the catheter shaft. In some embodiments, the high-density electrode catheter can include a flexible tip portion located adjacent to the distal end of the catheter shaft, wherein the flexible tip portion includes a flexible framework. In some embodiments, the high-density electrode catheter can include a plurality of electrodes disposed on the flexible framework. In some embodiments, the high-density electrode catheter can include a tip magnetic position sensor disposed on a portion of the flexible framework.

Various embodiments of the present disclosure can include a high-density electrode catheter. In some embodiments, the high-density electrode catheter can include a catheter shaft including a proximal end and a distal end, the catheter shaft defining a catheter shaft longitudinal axis. In some embodiments, the high-density electrode catheter can include a flexible tip portion located adjacent to the distal end of the catheter shaft, wherein the flexible tip portion includes a flexible framework that includes a longitudinally extending first outboard arm, second outboard arm, and central arm. In some embodiments, the high-density electrode catheter can include a plurality of electrodes disposed on each of the first outboard arm, second outboard arm, and central arm. In some embodiments, the high-density electrode catheter can include a tip magnetic position sensor disposed on a distal portion of the central arm.

Various embodiments of the present disclosure can include a high-density electrode catheter. In some embodiments, the high-density electrode catheter can include a catheter shaft including a proximal end and a distal end, the catheter shaft defining a catheter shaft longitudinal axis. In some embodiments, the high-density electrode catheter can include a flexible tip portion located adjacent to the distal end of the catheter shaft, wherein the flexible tip portion includes a flexible framework. In some embodiments, the high-density electrode catheter can include a flexible circuit disposed on the flexible framework, wherein the flexible circuit includes a plurality of electrodes disposed thereon. In some embodiments, the high-density electrode catheter can include a tip magnetic position sensor disposed on a portion of the flexible framework.

BRIEF DESCRIPTION OF THE DRAWINGS

FIG. 3G is an isometric top and side view of the high-density electrode catheter depicted in FIGS. 3A to 3F, further depicting a mounting portion, in accordance with embodiments of the present disclosure.

FIG. 3J is an isometric bottom and side view of a flexible understructure of the high-density electrode catheter depicted in FIGS. 3A to 3I, in accordance with embodiments of the present disclosure.

FIG. 3K is a cross-sectional view of a bi-lumen tube, in accordance with embodiments of the present disclosure.

FIG. 3O is a bottom view of the proximal end of the flexible understructure, in accordance with embodiments of the present disclosure.

FIG. 3Q is an isometric distal end view of the connective stem portion, in accordance with embodiments of the present disclosure.

FIG. 3R is an isometric proximal end view of the connective stem portion depicted in FIG. 3G, in accordance with embodiments of the present disclosure.

FIGS. 8A to 8E depict various electrode spacing configurations for electrodes disposed on a distal flexible tip portion of a high-density electrode catheter, in accordance with embodiments of the present disclosure.

DETAILED DESCRIPTION

Figure 1A:
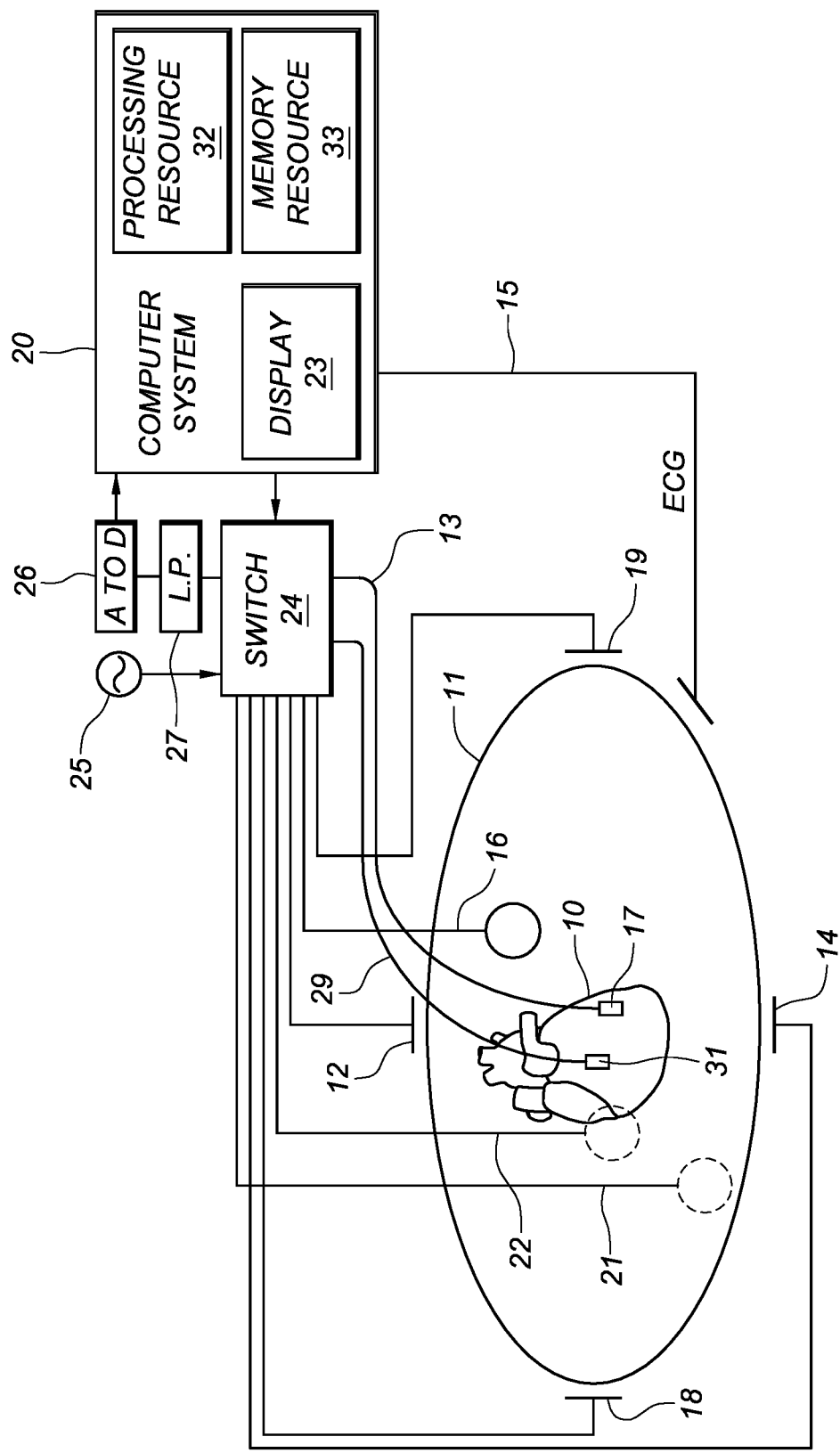
FIG. 1A is a diagrammatic overview of a catheter system, in accordance with embodiments of the present disclosure.

Referring now to the drawings wherein like reference numerals are used to identify identical components in the various views, FIG. 1A is a diagrammatic overview of a catheter system in which the invention may be practiced. The system may comprise various visualization, mapping and navigation components as known in the art, including among others, for example, an EnSite™ Precision™ Cardiac Mapping and Visualization System commercially available from Abbott Laboratories, as further discussed herein.

The system may be used in connection with or for various medical procedures, for example, mapping of the heart and/or cardiac ablation procedures. In one embodiment, the medical positioning system 14 may comprise a magnetic field-based system such as, for example, the CARTO® System available from Biosense Webster, and as generally shown with reference to one or more of U.S. Pat. Nos. 6,498,944; 6,788,967; and 6,690,963, the entire disclosures of which are incorporated in their entireties as though fully set forth herein. In another embodiment, the magnetic field based system can partly comprise a magnetic field based system such as the MediGuide™ Technology system from Abbott Laboratories, and as generally shown with reference to one or more of U.S. Pat. Nos. 6,233,476; 7,197,354; and 7,386,339; U.S. patent application Ser. No. 14/208,120 entitled "Medical Device Navigation System" filed on 13 Mar. 2014, U.S. Provisional Patent Application No. 61/834,223 entitled "Medical Device Navigation System" filed on 12 Jun. 2013, and International Application No. PCT/M2014/059709 entitled "Medical Device Navigation System" filed on 13 Mar. 2014, the disclosures of which are hereby incorporated by reference in their entireties as though fully set forth herein.

In yet another embodiment, the medical positioning system 14 may comprise a combination magnetic field-based system and electric field-based system such as, for example and without limitation, the systems described in pending U.S. patent application Ser. No. 13/231,284 entitled "Catheter Navigation Using Impedance and Magnetic Field Measurements" filed on 13 Sep. 2011 and U.S. patent application Ser. No. 13/087,203 entitled "System and Method for Registration of Multiple Navigation Systems to a Common Coordinate Frame" filed on 14 Apr. 2011, each of which is hereby incorporated by reference in its entirety as though set fully forth herein, or the CARTO® 3 system commercially available from Biosense Webster. In some embodiments, the medical positioning system 14 can comprise or be used in conjunction with other commonly available systems, such as, for example and without limitation, fluoroscopic, computed tomography (CT), and magnetic resonance imaging (MRI)-based systems. For purposes of clarity and illustration only, the medical positioning system 14 will be described hereinafter as comprising a hybrid magnetic and impedance tracking system. Although reference is made to cardiac mapping of the heart, one or more aspects of the present disclosure may apply to other anatomic structures.

With reference to FIG. 1A, the catheter system includes a diagrammatic depiction of a heart 10 of a patient 11. The system includes the ability to receive a plurality of catheter locations as the catheter distal end is swept around and within a chamber of the heart. For this purpose, FIG. 1A shows an exemplary catheter localization system of the type based on externally-applied orthogonal electric fields which are used to determine the location of one or more catheter position sensors. Such a system can include an impedance localization system and/or hybrid magnetic and impedance tracking system such an EnSite™ NavX™ Electro Anatomical Mapping System, an EnSite™ Velocity™ Electro Anatomical Mapping System, and an EnSite Precision™ Electro Anatomical Mapping System, all commercially available from Abbott Laboratories, or as seen generally by reference to U.S. Pat. No. 7,263,397 (the '397 patent), or U.S. Patent Publication No. 2007/0060833 A1, U.S. application Ser. No. 11/227,580 filed 15 Sep. 2005 (the '580 application), or US Publication No. 2018/0296111 A1, U.S. application Ser. No. 15/953,155 filed 13 Apr. 2018 (the '155 application). The '397 patent, the '580 application, and the '155 application are all hereby incorporated by reference as though fully set forth herein.

The various EnSite™ systems are based on the principal that when electrical currents are passed through the thorax, a voltage drop occurs across internal organs such as the heart and this voltage drop can be measured and used to determine the position of a medical device within the body. It should be understood, however, that this embodiment is exemplary only and not limiting in nature. Other technologies for determining the location in 3D space of a catheter, such as the MediGuide™ system, may be used in practicing the present invention, including for example, the CARTO® navigation and location system of Biosense Webster, Inc., or the AURORA® system of Northern Digital Inc., both of which utilize magnetic fields rather than electrical fields. Accordingly, as used herein, a sensor is provided for producing signals indicative of catheter location information, and may include one or more position sensors. The position sensors can include one or more electrodes configured to detect one or more characteristics of an electrical field, for example in the case of an impedance-based localization system, or alternatively, one or more coils (e.g., wire windings) configured to detect one or more characteristics of a magnetic field, for example, in the case of a magnetic-field based localization system.

It should be further understood that in some localization systems, one or more position sensors may collectively define the sensor. The one or more position sensors may be provided on a distal end of a catheter and the localization system may be configured to obtain location information from the one or more position sensors. The localization system may compute a distal location of the catheter using not only the received location information, but also a geometrical relationship between the one or more position sensors providing the location information and the distal location on the catheter (e.g., one piece of geometrical information may be the ring electrode to tip distance). Finally, the localization system may use the computed location, as if it were collected directly. Likewise, in a magnetic field based localization embodiment, the catheter tip and the magnetic coil may have a geometrical relationship therebetween where the localization system is configured to use the computed tip location (i.e., computed based on the magnetic coil signals and predefined knowledge of the geometrical relationship between coil and tip) as if such location were collected directly. Of course, other variations are possible.

With continued reference to FIG. 1A, in the illustrated impedance-based localization system embodiment, three sets of surface electrodes (e.g., applied via a patch) are shown: X-axis electrodes 12, 14; Y-axis electrodes 18, 19; and Z-axis electrodes 16, 22. In some embodiments, an additional surface electrode 21 (e.g., applied via a "belly" patch) may be used. The surface electrodes are all connected to a switch 24. A representative catheter 13 is shown, which has a single distal electrode 17, which may be referred to herein as a "roving" or "measurement" electrode. In some embodiments, the catheter 13 can be a coronary sinus catheter or a right ventricle apex catheter. The electrode 17 may define the position sensor in this embodiment, but as alluded to above, many variations are possible and the catheter 13 can include multiple position sensors, as discussed further herein. FIG. 1A also shows a second, independent catheter 29 with a fixed reference electrode 31, which may be stationary on the heart 10 for calibration purposes.

FIG. 1A further shows a computer system 20, a signal generator 25, an analog-to-digital converter 26 and a low-pass filter 27. The computer system 20 can utilize software, hardware, firmware, and/or logic to perform a number of functions described herein. The computing system 20 can be a combination of hardware and instructions to share information. The hardware, for example can include processing resource 32 and/or a memory resource 33 (e.g., non-transitory computer-readable medium (CRM) database, etc.). A processing resource 32, as used herein, can include a number of processors capable of executing instructions stored by the memory resource 33. The processing resource 32 can be integrated in a single device or distributed across multiple devices. The instructions (e.g., computer-readable instructions (CRI)) can include instructions stored on the memory resource 33 and executable by the processing resource 32 for aligning a cardiac model.

The computer system 20 is configured to control the signal generator 25 in accordance with predetermined strategies to selectively energize various pairs of surface electrodes. In operation, the computer system 20 is configured to obtain raw patch data (i.e., voltage readings) via the filter 27 and A-D converter 26 and use this raw patch data to determine the raw electrode location coordinates in three-dimensional space (X, Y, Z) of a catheter electrode positioned inside the heart 10 or chamber thereof (e.g., such as the roving electrode 17 mentioned above). In some embodiments, a phase of the patient's 11 cardiac cycle can be measured or otherwise determined when such electrode location coordinates are being received. For this purpose, in an embodiment, most or all of the conventional twelve (12) ECG leads, coupled to body surface electrodes and designated collectively by reference numeral 15, are provided to support the acquisition of an electrocardiogram (ECG) of the patient 11.

Alternatively, a reference electrode positioned in a fixed location in the heart 10, such as fixed reference electrode 31, may be used to provide a relatively stable signal that can be analyzed to determine the cardiac phase of the heart 10 in the cardiac cycle (e.g., placed at the coronary sinus). More generally, another catheter having an electrode, other than the moving or roving catheter, may be placed and maintained in a constant position relative to the heart 10 to obtain a relatively stable signal indicative of cardiac phase. As shown, the ECG leads 15 are coupled directly to the computer system 20 for acquisition and subsequent processing to obtain the phase of the heart 10 in the cardiac cycle. The ECG leads 15 may also be provided to other systems (not shown).

As previously mentioned, embodiments of the present disclosure can be used with a magnetic field-based system. Some embodiments can include a main electronic control unit (e.g., one or more processors) having various input/output mechanisms, a display 23, an optional image database, a localization system such as a medical positioning system (VIPS) (electromagnetic sensor tracking system), an electrocardiogram (ECG) monitor, one or more MPS location sensors (e.g., patient reference sensor), and an MPS-enabled medical device (such as an elongated catheter or introducer) which itself includes one or more of the above-described MPS location sensors.

As discussed, in some embodiments, the medical positioning system may comprise a magnetic field-based system such as, for example, the MediGuide™ Technology system from Abbott Laboratories, and as generally shown with reference to one or more of U.S. Pat. Nos. 6,233,476; 7,197,354; and 7,386,339; U.S. patent application Ser. No. 14/208,120 entitled "Medical Device Navigation System" filed on 13 Mar. 2014, U.S. Provisional Patent Application No. 61/834,223 entitled "Medical Device Navigation System" filed on 12 Jun. 2013, and International Application No. PCT/M2014/059709 entitled "Medical Device Navigation System" filed on 13 Mar. 2014, the disclosures of which are hereby incorporated by reference in their entireties as though fully set forth herein.

Embodiments can include input/output mechanisms, which can comprise conventional apparatus for interfacing with a computer-based control unit, for example, a keyboard, a mouse, a tablet, a foot pedal, a switch or the like. Embodiments can also include a display 23, which can also comprise conventional apparatus.

Embodiments may find use in navigation applications that use imaging of a region of interest. Therefore, the magnetic field-based system may optionally include an image database. The image database may be configured to store image information relating to the patient's body, for example, a region of interest surrounding a destination site for the medical device and/or multiple regions of interest along a navigation path contemplated to be traversed by the device to reach the destination site. The image data in the image database may comprise known image types including (1) one or more two-dimensional still images acquired at respective, individual times in the past; (2) a plurality of related two-dimensional images obtained in real-time from an image acquisition device (e.g., fluoroscopic images from an x-ray imaging apparatus) wherein the image database acts as a buffer (live fluoroscopy); and/or (3) a sequence of related two-dimensional images defining a cine-loop (CL), wherein each image in the sequence has at least an ECG timing parameter associated therewith adequate to allow playback of the sequence in accordance with acquired real-time ECG signals obtained from the ECG monitor. It should be understood that the foregoing are examples only and not limiting in nature. For example, the image database may also include three-dimensional image data. It should be further understood that the images may be acquired through any imaging modality, now known or hereafter developed, for example X-ray, ultra-sound, computerized tomography, nuclear magnetic resonance or the like.

The MPS can be configured to serve as the localization system and therefore to determine positioning (localization) data with respect to one or more of MPS location sensors, one or more medical devices, and/or on one or more patient reference sensors (PRS), and output a respective location reading. The location readings may each include at least one or both of a position and an orientation (P&O) relative to a reference coordinate system, which may be the coordinate system of the MPS. For example, the P&O may be expressed as a position (i.e., a coordinate in three axes X, Y, and Z) and orientation (i.e., an azimuth and elevation) of a magnetic field sensor in a magnetic field relative to a magnetic field generator(s) or transmitter(s).

The MPS determines respective locations (i.e., P&O) in the reference coordinate system based on capturing and processing signals received from the magnetic field sensors, while such sensors are disposed in a controlled low-strength AC magnetic field. From an electromagnetic perspective, these sensors develop a voltage that is induced on the coil residing in a changing magnetic field, as contemplated here. The sensors are thus configured to detect one or more characteristics of the magnetic field(s) in which they are disposed and to generate an indicative signal, which is further processed by the MPS to obtain a respective P&O of the sensors. Exemplary design features and manufacturing processes and methods for the sensors and medical devices incorporating such sensors may be found in U.S. Pat. No. 8,636,718, the entirety of which is incorporated by reference herein.

The MPS sensor, and optionally additional MPS sensors in further embodiments, may be associated with the MPS-enabled medical device. Another MPS sensor, namely, a patient reference sensor (PRS) is configured to provide a positional reference of the patient's body so as to allow motion compensation for gross patient body movements and/or respiration-induced movements. The PRS may be attached to the patient's manubrium sternum, a stable place on the chest, or another location that is relatively positionally stable. Like MPS location sensor, the PRS is configured to detect one or more characteristics of the magnetic field in which it is disposed, wherein the MPS provides a location reading (e.g., a P&O reading) indicative of the PRS's position and orientation in the reference coordinate system.

The electro-cardiogram (ECG) monitor is configured to continuously detect an electrical timing signal of the heart organ through the use of a plurality of ECG electrodes (not shown), which may be externally-affixed to the outside of a patient's body. The timing signal generally corresponds to the particular phase of the cardiac cycle, among other things. Generally, the ECG signal(s) may be used by the control unit for ECG synchronized playback of a previously captured sequence of images (cine loop) stored in the database. The ECG monitor and the ECG-electrodes may both comprise conventional components.

The magnetic field-based system can be incorporated into or associated with a fluoroscopic imaging system, which may include commercially available fluoroscopic imaging components, for example, an x-ray source, a C-Arm, and/or an x-ray image intensifier or detector (i.e., "Catheter Lab"). The MPS (electromagnetic sensor tracking system) includes a magnetic transmitter assembly (MTA) (electromagnetic field generator) and a magnetic processing core for determining location (P&O) readings. The MTA is configured to generate the magnetic field(s) in and around the patient's chest cavity, in a predefined three-dimensional space identified as a motion box.

The MPS sensors are, as described above, configured to sense one or more characteristics of the magnetic field(s) when the sensors are in a motion box, and each generate a respective signal that is provided to the magnetic processing core. The processing core is responsive to these detected signals and is configured to calculate respective P&O readings for each MPS sensor in the motion box. The processing core can detect when an MPS sensor exits the motion box. Thus, the MPS enables real-time tracking of each sensor in three-dimensional space.

The actual volume of the motion box may be stored in, for example, the processing core, and processing core is able to determine the positions and orientations of each sensor in relation to the boundaries of motion box. Alternatively, the actual volume of motion box may be stored in, for example, the main control, and the main control may be able to determine the positions and orientations of each sensor in relation to the boundaries of the motion box. Accordingly, the system can evaluate (e.g., in the processing core or in the main control) whether a sensor is within, at the boundary of, or outside of the motion box. Based on this information, the motion box and sensor(s) can be displayed in relation to one another on the display as described in greater detail elsewhere herein.

In some alternative embodiments, the MTA can be located underneath a patient examination table, between an x-ray source and the patient examination table. For example, the MTA can be connected with the patient examination table. In some embodiments, as discussed herein, the MTA can be a mobile device, which can be placed on a chest of the patient and used to generate the magnetic field for tracking of the object.

The positional relationship between the image coordinate system and the MPS reference coordinate system (electromagnetic tracking coordinate system) may be calculated based on a known optical-magnetic calibration of the system (e.g., established during setup), since the positioning system and imaging system may be considered fixed relative to each other in such an embodiment. However, for other embodiments using other imaging modalities, including embodiments where the image data is acquired at an earlier time and then imported from an external source (e.g., imaging data stored in the database), a registration step registering the MPS coordinate system and the image coordinate system may need to be performed so that MPS location readings can be properly coordinated with any particular image being used.

As previously mentioned, embodiments of the present disclosure may be used in connection with or for various medical procedures, for example, mapping of the heart and/or cardiac ablation therapy procedures. In some embodiments, ablation therapy may be used to treat various conditions afflicting the human anatomy. One such condition in which ablation therapy may be used is the treatment of cardiac arrhythmias. When tissue is ablated, or at least subjected to ablative energy generated by an ablation generator and delivered by an ablation catheter, lesions form in the tissue. Electrodes mounted on or in ablation catheters are used to create tissue necrosis in cardiac tissue to correct conditions such as atrial arrhythmia (including, but not limited to, ectopic atrial tachycardia, atrial fibrillation, and atrial flutter). Arrhythmias can create a variety of dangerous conditions including loss of synchronous atrioventricular contractions and stasis of blood flow. It is believed that the primary cause of atrial arrhythmia is stray electrical signals within the left or right atrium of the heart. The ablation catheter imparts ablative energy (e.g., radiofrequency energy, cryoablation, lasers, chemicals, high-intensity focused ultrasound, etc.) to cardiac tissue to create a lesion in the cardiac tissue. This lesion disrupts undesirable electrical pathways and thereby limits or prevents stray electrical signals that lead to arrhythmias.

In some embodiments, ablation can include electroporation. Electroporation is a non-thermal ablation technique that involves applying strong electric-fields that induce pore formation in the cellular membrane. The electric field may be induced by applying a relatively short duration pulse which may last, for example, from a nanosecond to several milliseconds. Such a pulse may be repeated to form a pulse train. When such an electric field is applied to tissue in an in vivo setting, the cells in the tissue are subjected to a trans-membrane potential, which opens the pores on the cell wall. Electroporation may be reversible (i.e., the temporally-opened pores will reseal) or irreversible (i.e., the pores will remain open), causing cellular destruction. For example, in the field of gene therapy, reversible electroporation is used to transfect high molecular weight therapeutic vectors into the cells. In other therapeutic applications, a suitably configured pulse train alone may be used to cause cell destruction, for instance by causing irreversible electroporation.

Figure 1B:
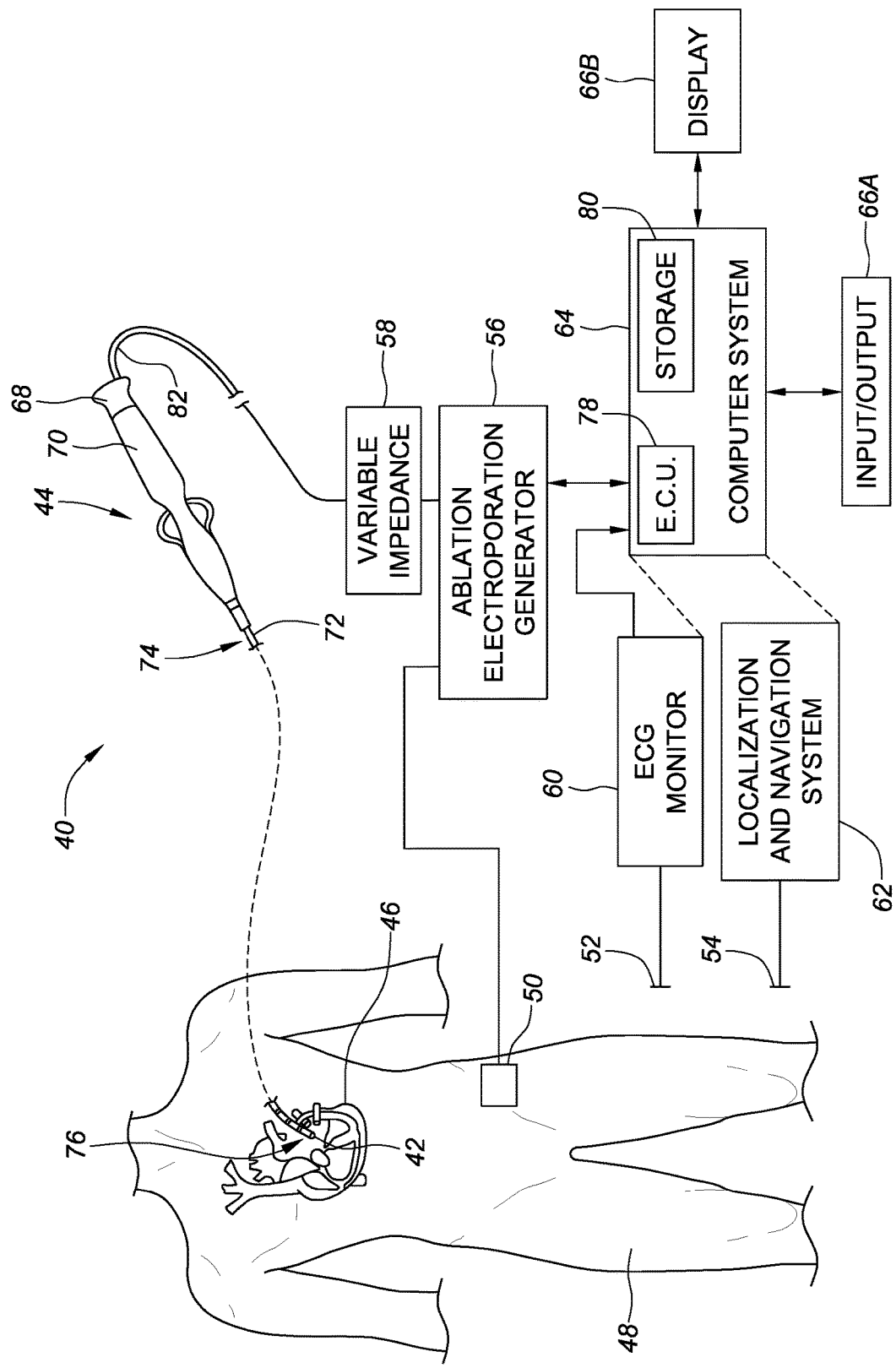
FIG. 1B is a diagrammatic and block diagram view of a system for electroporation therapy, in accordance with embodiments of the present disclosure.

FIG. 1B is a diagrammatic and block diagram view of a system 40 for electroporation therapy, in accordance with embodiments of the present disclosure. In general, the various embodiments include an electrode assembly 42 disposed at the distal end of a catheter 44. The electrode assembly 42 includes one or more individual, electrically-isolated electrode elements. Each electrode element, also referred to herein as a catheter electrode, is individually wired such that it can be selectively paired or combined with any other electrode element to act as a bipolar or a multi-polar electrode.

System 40 may be used for irreversible electroporation to destroy tissue. In particular, system 40 may be used for electroporation-induced primary necrosis therapy, which refers to the effects of delivering electrical current in such manner as to directly cause an irreversible loss of plasma membrane (cell wall) integrity leading to its breakdown and cell necrosis. This mechanism of cell death may be viewed as an "outside-in" process, meaning that the disruption of the outside wall of the cell causes detrimental effects to the inside of the cell. Typically, for classical plasma membrane electroporation, electric current is delivered as a pulsed electric field (i.e., pulsed field ablation (PFA)) in the form of short-duration direct current (DC) pulses (e.g., 0.1 to 20 ms duration) between closely spaced electrodes capable of delivering an electric field strength of about 0.1 to 1.0 kV/cm.

System 40 includes a catheter electrode assembly 42 including at least one catheter electrode configured to be used as briefly outlined above and as described in greater detail below. Electrode assembly 42 is incorporated as part of a medical device such as a catheter 44 for electroporation therapy of tissue 46 in a body 48 of a patient. In the illustrative embodiment, tissue 46 comprises heart or cardiac tissue. It should be understood, however, that embodiments may be used to conduct electroporation therapy with respect to a variety of other body tissues.

FIG. 1A further shows a plurality of return electrodes designated 50, 52, and 54, which are diagrammatic of the body connections that may be used by the various subsystems included in the overall system 40, such as an electroporation generator 56, an electrophysiology (EP) monitor such as an ECG monitor 60, a localization and navigation system 62 for visualization, mapping and navigation of internal body structures. In the illustrated embodiment, return electrodes 50, 52, and 54 are patch electrodes. It should be understood that the illustration of a single patch electrode is diagrammatic only (for clarity) and that such sub-systems to which these patch electrodes are connected may, and typically will, include more than one patch (body surface) electrode.

In some embodiments, return electrodes 50, 52, and 54 may be any other type of electrode suitable for use as a return electrode including, for example, one or more catheter electrodes. Return electrodes that are catheter electrodes may be part of electrode assembly 42 or part of a separate catheter (not shown). System 40 may further include a main computer system 64 (including an electronic control unit 78 and data storage—memory 80), which may be integrated with system 62 in certain embodiments. In some embodiments, the main computer system 64 can be integrated with the computer system 20, depicted in FIG. 1A. System 64 may further include conventional interface components, such as various user input/output mechanisms 66A and a display 66B, among other components. A variable impedance device 58 allows the impedance of the system to be varied to limit arcing from the catheter electrode of catheter 44. In some embodiments, variable impedance device 58 is variable in response to an appropriate control signal from computer system 64.

In the illustrative embodiment, catheter 44 includes a cable connector or interface 68, a handle 70, and a shaft 72 having a proximal end 74 and a distal end 76. Catheter 44 may also include other conventional components not illustrated herein such as a temperature sensor, additional electrodes, and corresponding conductors or leads. The connector 68 provides mechanical and electrical connection(s) for cable 82 extending from generator 56. The connector 68 may comprise conventional components known in the art and as shown is disposed at the proximal end of catheter 44.

Figure 2A:
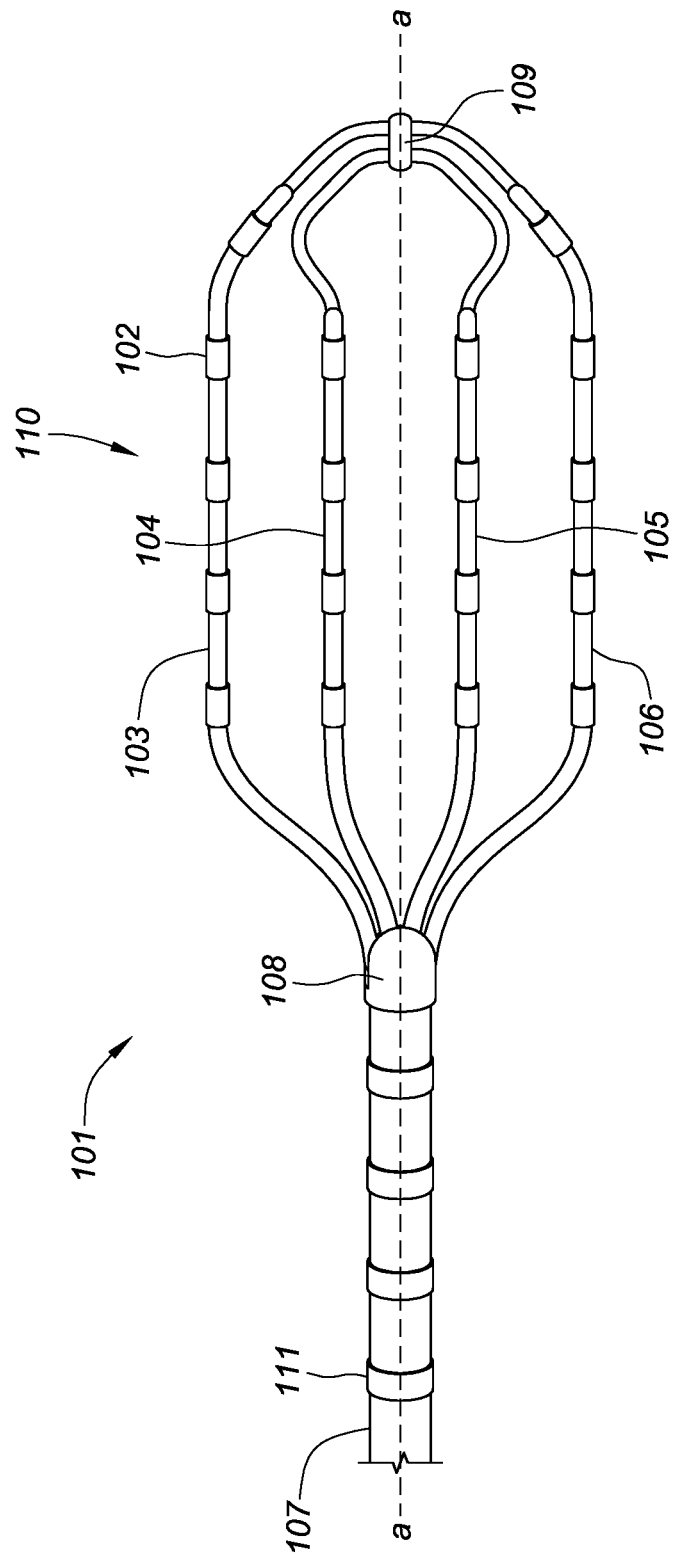
FIG. 2A is a top view of a high-density electrode catheter and FIG. 2B is an isometric side and top view of the high-density electrode catheter, in accordance with various embodiments of the present disclosure.
Figure 2B:
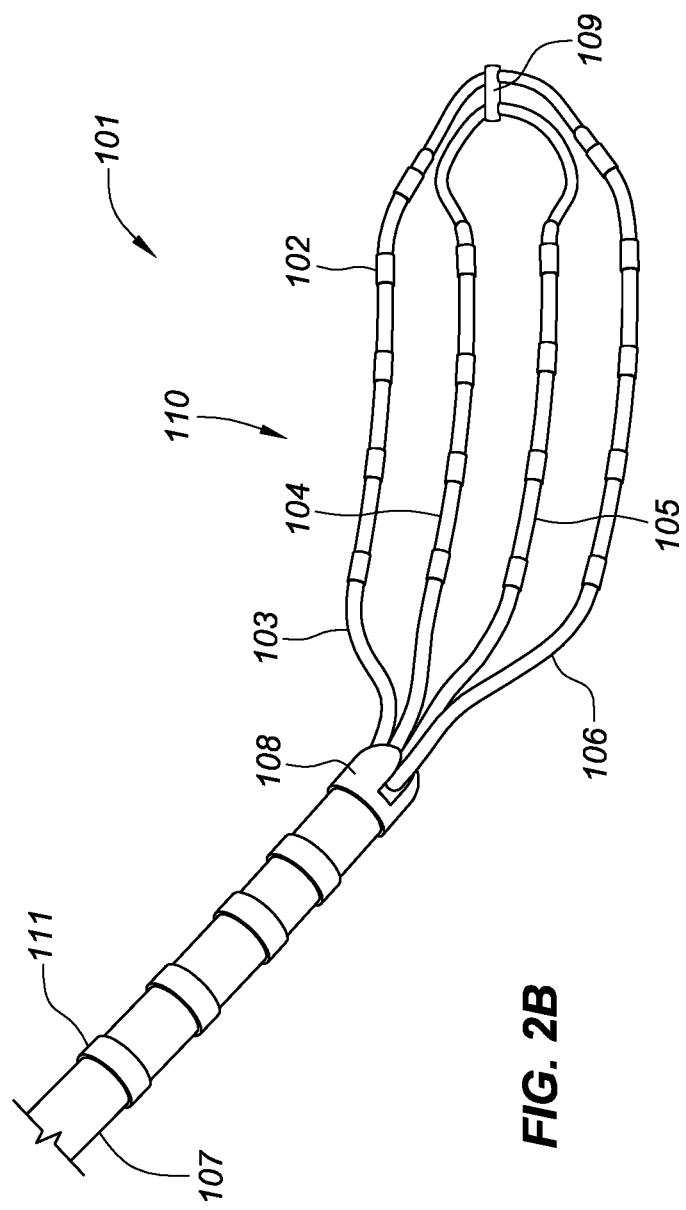

FIG. 2A is a top view of a high-density electrode catheter 101 and FIG. 2B is an isometric side and top view of the high-density electrode catheter 101, according to various embodiments of the present disclosure. In some embodiments, the high-density electrode catheter 101 can include a flexible tip portion 110 that forms a flexible array of electrodes 102. This planar array (or 'paddle' configuration) of electrodes 102 comprises four side-by-side, longitudinally-extending arms 103, 104, 105, 106, which can form a flexible framework on which the electrodes 102 are disposed. The four electrode-carrier arms can comprise a first outboard arm 103, a second outboard arm 106, a first inboard arm 104, and a second inboard arm 105, which can be joined at a distal end by a distal connective portion 109. These arms can be laterally separated from each other.

Each of the four arms can carry a plurality of electrodes 102. For example, each of the four arms can carry electrodes 102 spaced along a length of each of the four arms. Although each of the high-density electrode catheters 101 depicted in FIGS. 2A and 2B depict four arms, the high-density electrode catheters 101 could comprise more or fewer arms. Additionally, while the high-density electrode catheter 101 depicted in FIGS. 2A and 2B depict 18 electrodes (e.g., 5 electrodes on the first outboard arm 103 and second outboard arm 106 and 4 electrodes on the first inboard arm 104 and second inboard arm 105), the catheters can include more or fewer than 18 electrodes. In addition, the first outboard arm 103 and second outboard arm 106 can include more or fewer than 5 electrodes and the first inboard arm 104 and second inboard arm 105 can include more or fewer than 4 electrodes).

In some embodiments, the electrodes 102 can be used in diagnostic, therapeutic, and/or mapping procedures. For example and without limitation, the electrodes 102 can be used for electrophysiological studies, pacing, cardiac mapping, and ablation. In some embodiments, the electrodes 102 can be used to perform unipolar or bipolar ablation. This unipolar or bipolar ablation can create specific lines or patterns of lesions. In some embodiments, the electrodes 102 can receive electrical signals from the heart, which can be used for electrophysiological studies. In some embodiments, the electrodes 102 can perform a location or position sensing function related to cardiac mapping.

In some embodiments, the high-density electrode catheter 101 can include a catheter shaft 107. The catheter shaft 107 can include a proximal end and a distal end. The distal end can include a connector 108, which can couple the distal end of the catheter shaft 107 to a proximal end of the planar array. The catheter shaft 107 can define a catheter shaft longitudinal axis aa, as depicted in FIG. 2A, along which the first outboard arm 103, first inboard arm 104, second inboard arm 105, and second outboard arm 106 can generally extend parallel in relation therewith. The catheter shaft 107 can be made of a flexible material, such that it can be threaded through a tortuous vasculature of a patient. In some embodiments, the catheter shaft 107 can include one or more ring electrodes 111 disposed along a length of the catheter shaft 107. The ring electrodes 111 can be used for diagnostic, therapeutic, and/or mapping procedures, in an example.

As depicted in FIG. 2B, the flexible tip portion 110 can be adapted to conform to tissue (e.g., cardiac tissue). For example, when the flexible tip portion 110 contacts tissue, the flexible tip portion 110 can deflect, allowing the flexible framework to conform to the tissue. In some embodiments, the arms (or the understructure of the arms) comprising the paddle structure (or multi-arm, electrode-carrying, flexible framework) at the distal end of the catheters depicted in FIGS. 2A and 2B are preferably constructed from a flexible or spring-like material such as Nitinol and/or a flexible substrate, as discussed herein. The construction (including, for example, the length and/or diameter of the arms) and material of the arms can be adjusted or tailored to create, for example, desired resiliency, flexibility, foldability, conformability, and stiffness characteristics, including one or more characteristics that may vary from the proximal end of a single arm to the distal end of that arm, or between or among the plurality of arms comprising a single paddle structure.

The foldability of materials such as Nitinol and/or flexible substrate provide the additional advantage of facilitating insertion of the paddle structure into a delivery catheter or introducer, whether during delivery of the catheter into the body or removal of the catheter from the body at the end of a procedure. In some embodiments, a non-conductive shell can be disposed over the material (e.g., Nitinol) that forms the understructure of the arms. In some embodiments, as discussed herein, the non-conductive shell can include a tube that defines a longitudinally extending lumen, through which the understructure is disposed. In some embodiments, the tube can be formed from a material that includes a polymer.

Among other things, the disclosed catheters, with their plurality of electrodes, are useful to (1) define regional propagation maps of particularly sized areas (e.g., one centimeter square areas) within the atrial walls of the heart; (2) identify complex fractionated atrial electrograms for ablation; (3) identify localized, focal potentials between the electrodes for higher electrogram resolution; and/or (4) more precisely target areas for ablation. These mapping catheters and ablation catheters are constructed to conform to, and remain in contact with, cardiac tissue despite potentially erratic cardiac motion. Such enhanced stability of the catheter on a heart wall during cardiac motion provides more accurate mapping and ablation due to sustained tissue-electrode contact.

Additionally, the catheters described herein may be useful for epicardial and/or endocardial use. For example, the planar array embodiments depicted herein may be used in an epicardial procedure where the planar array of electrodes is positioned between the myocardial surface and the pericardium. Alternatively, the planar array embodiments may be used in an endocardial procedure to quickly sweep and/or analyze the inner surfaces of the myocardium and quickly create high-density maps of the heart tissue's electrical properties.

In some embodiments, use of the high-density electrode catheter 101 could be susceptible to coagulation of blood on various portions of the high-density electrode catheter 101. For example, coagulation of blood can occur on the flexible tip portion 110 and/or on the connector 108 of the high-density electrode catheter 101. Although coagulation of blood is discussed herein, in some instances other material can be collected on the flexible tip portion 110 and/or on the connector 108, such as tissue cells, for example. Coagulation of blood can impair the functionality of the electrodes if the blood coagulates on the electrodes. Additionally, coagulation of blood on the flexible tip portion 110 and/or on the connector 108 can cause clots to occur, if the coagulated blood breaks free. As such, it can be beneficial to prevent the coagulation of blood and/or accumulation of other material on the flexible tip portion 110 and/or on the connector 108, which can be accomplished through use of embodiments discussed in the present disclosure.

The contents of International Application No. PCT/US2014/011940 entitled Flexible High-Density Mapping Catheter Tips and Flexible Ablation Catheter Tips with Onboard High-Density Mapping Electrodes; U.S. application Ser. No. 15/331,562 entitled High Density Electrode Mapping Catheter; and U.S. application Ser. No. 15/331,369 entitled High Density Electrode Mapping Catheter are hereby incorporated by reference as though fully set forth herein. Although some embodiments of the present disclosure include a flexible tip portion that includes diagnostic and/or therapeutic electrodes, embodiments of the present disclosure can include a flexible and/or rigid tip portion (e.g., distal assembly) in lieu of or in addition to the flexible tip portion, which can be an electrode assembly or any number of end use therapeutic and/or diagnostic devices. For example, the tip portion can include an ultrasound sensor and/or transducer, such as that associated with an intracardiac echocardiography (ICE) catheter; a laser, balloon or any other number of therapeutic and/or diagnostic devices.

In some embodiments, although not depicted, a magnetic position sensor can be included in the catheter shaft 107 of the high-density electrode catheter 101. In some embodiments, a position of the magnetic position sensor can be determined, as discussed herein. Based on the position of the magnetic position sensor, the position of the flexible tip portion 110 can be determined. However, in some embodiments, depending on a size of the flexible tip portion 110, the flexible tip portion 110 can extend beyond a reach of where the position of the flexible tip portion 110 can be accurately determined with the magnetic position sensor disposed in the catheter shaft 107. For example, a longitudinal length of the flexible tip portion 110 can extend beyond a reach of where the position of the flexible tip portion 110 can be accurately determined with the magnetic position sensor disposed in the catheter shaft 107. Accordingly, embodiments of the present disclosure can include a magnetic position sensor, as further discussed herein, disposed on the flexible tip portion 110 of the high-density electrode catheter 101. In some embodiments, one or more magnetic position sensors may be disposed on the flexible tip portion in lieu of a magnetic position sensor disposed in the catheter shaft 107.

Figure 3A:
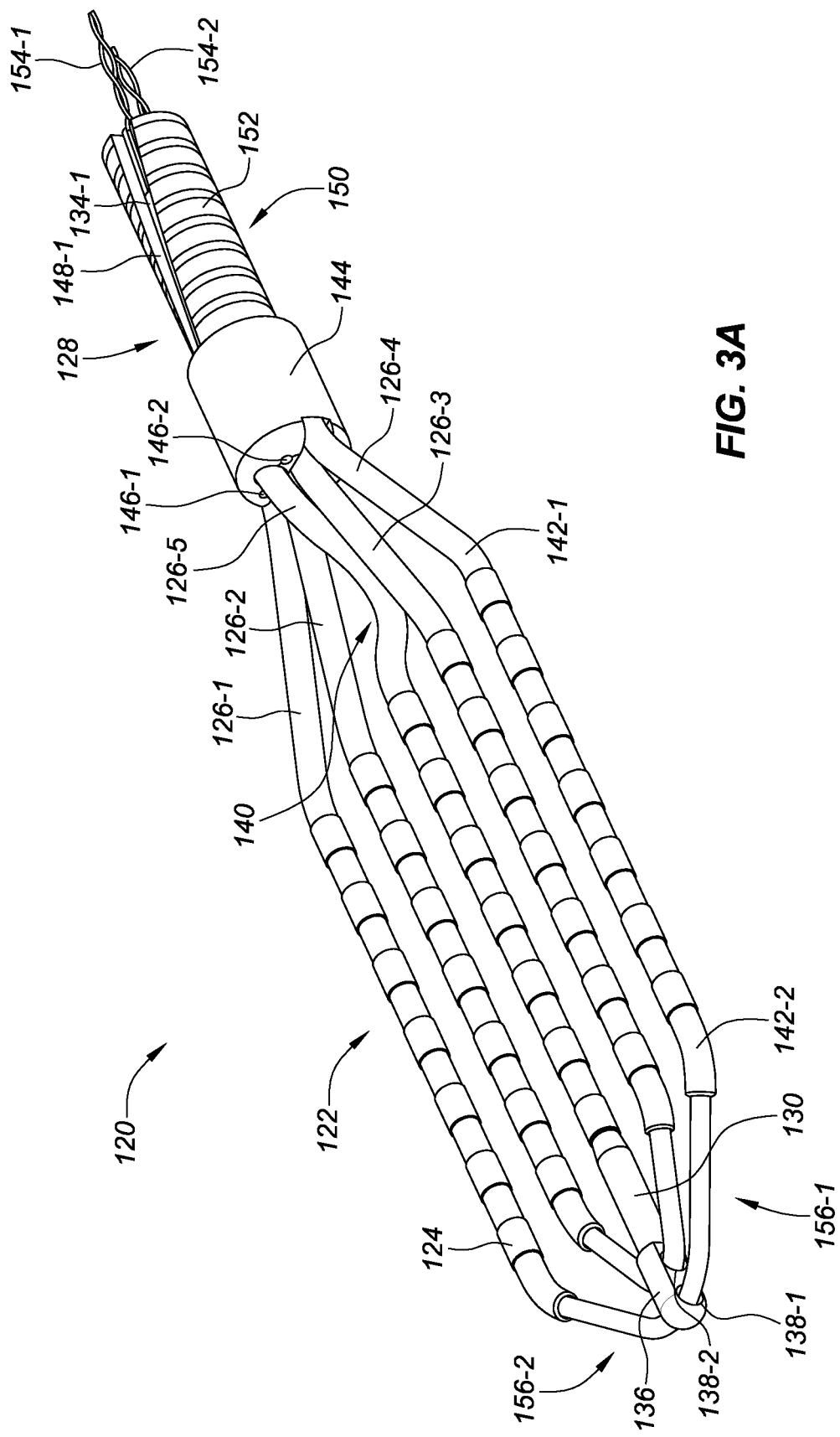
FIG. 3A is an isometric side and top view of a high-density electrode catheter and FIG. 3B is a bottom view of the high-density electrode catheter, in accordance with various embodiments of the present disclosure.
Figure 3B:
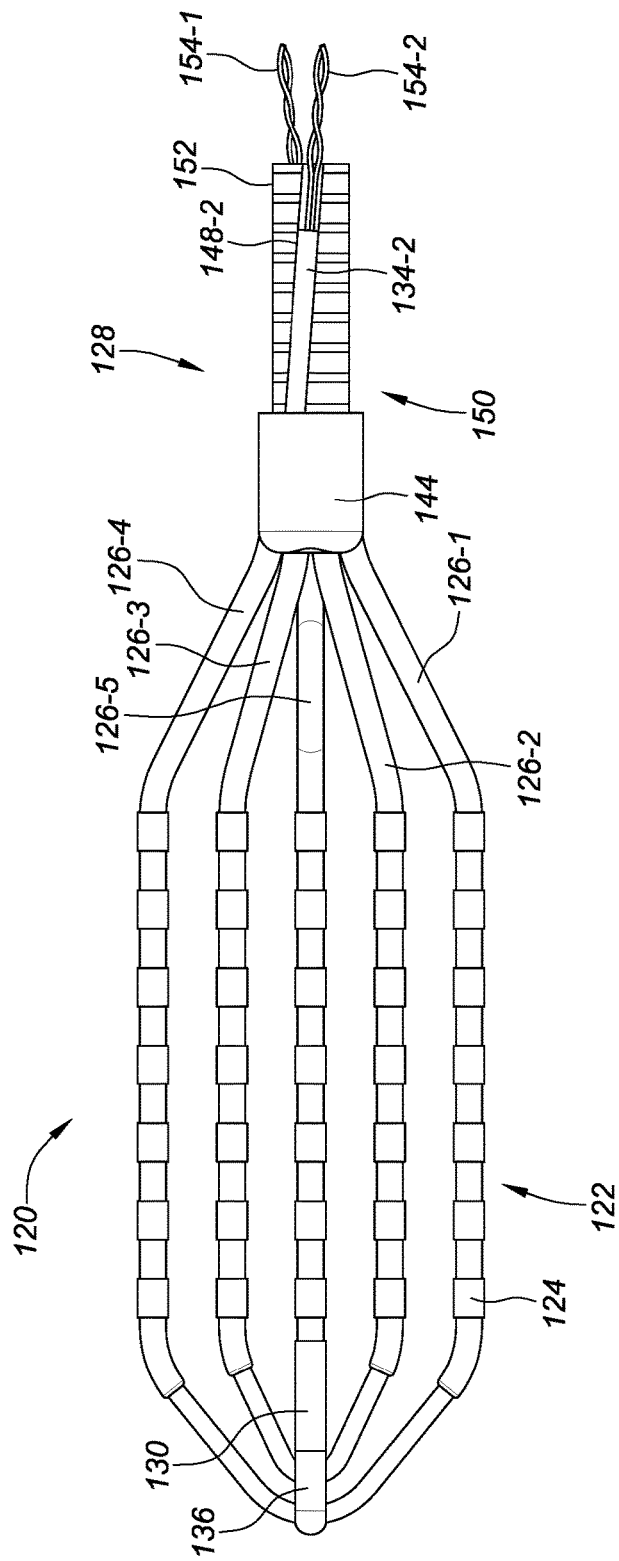

FIG. 3A is an isometric side and top view of a high-density electrode catheter 120 and FIG. 3B is a bottom view of the high-density electrode catheter 120, according to various embodiments of the present disclosure. In some embodiments, the high-density electrode catheter 120 can include a flexible tip portion 122 that forms a flexible array of electrodes 124. The flexible tip portion 122 can be located adjacent to a distal end of a catheter shaft, not shown. In some embodiments, the flexible tip portion 122 can be connected to the catheter shaft via a proximal coupler 128, further discussed herein. This planar array (or 'paddle' configuration) of electrodes 124 comprises five side-by-side, longitudinally-extending arms 126-1, 126-2, 126-3, 126-4, 126-5, which can form a flexible framework on which the electrodes 124 are disposed. As depicted, seven electrodes 124 can be disposed along each of the longitudinally extending arms 126-1, 126-2, 126-3, 126-4, 126-5 for a total of 35 electrodes. In some embodiments, a greater or lesser number of electrodes 124 can be disposed on the flexible tip portion 122. In some embodiments, as further discussed herein, one or more additional electrodes 130 can be disposed along a central arm 126-5, or along another portion of the flexible tip portion 122.

Although five-side-by-side arms 126-1, 126-2, 126-3, 126-4, 126-5 are depicted, embodiments of the present disclosure can include fewer than 5 arms or greater than 5 arms. In some embodiments, the five electrode-carrier arms can comprise a first outboard arm 126-1, a second outboard arm 126-4, a first inboard arm 126-2, a second inboard arm 126-3, and a central arm 126-5, which can be joined at a distal end by a distal coupler 136. In some embodiments, the distal coupler 136 can extend longitudinally and define one or more transverse lumens 138-1, 138-2 extending therethrough. In some embodiments, the distal portions of the first and second outboard arms 126-1, 126-2 and the first and second inboard arms 126-2, 126-3 can extend through the transverse lumens 138-1, 138-2, thereby coupling the arms 126-1, 126-2, 126-3, 126-4 together. However, as further discussed herein, in some embodiments, the arms 126-1, 126-2, 126-3, 126-4, 126-5 may not be coupled together at their distal ends.

In some embodiments, the flexible tip portion 122 can include a magnetic position sensor 209, as further seen in FIG. 3J. In some embodiments, the magnetic position sensor 209 can be disposed along a distal portion of a flexible framework that forms the flexible tip portion 122. Although hidden from view in FIG. 3A, the magnetic position sensor 209 can be disposed within a central electrode 130. For example, as further depicted in FIG. 3J, the central electrode 130 can define a lumen in which the magnetic position sensor 209 is disposed.

In some embodiments, the magnetic position sensor 209 can be disposed on and/or in a portion of the flexible tip portion 122. In some embodiments, a distal portion of the flexible tip portion 122 can define a mounting feature for the magnetic position sensor 209. In some embodiments, the mounting feature can include a cutout in a portion of the flexible tip portion 122, a groove in a portion of the flexible tip portion, a lumen in a portion of the flexible tip portion, etc. In some embodiments, a cutout can be defined in one of the arms 126-1, 126-2, . . . , 126-5, in the distal coupler 136, a framework that forms one of the arms 126-1, 126-2, . . . , 126-5, or in other locations in the flexible tip portion 122.

In some embodiments, a groove can be defined in one of the arms 126-1, 126-2, . . . , 126-5, in the distal coupler 136, a framework that forms one of the arms 126-1, 126-2, . . . , 126-5, or in other locations in the flexible tip portion 122. In some embodiments, as discussed herein, the central electrode 130 can define a lumen in which the magnetic position sensor 209 can be disposed. In some embodiments, a lumen can be formed in other structures included in the flexible tip portion 122. For example, a lumen can be defined in one of the arms 126-1, 126-2, . . . , 126-5, in the distal coupler 136, a framework that forms one of the arms 126-1, 126-2, . . . , 126-5, or in other locations in the flexible tip portion 122. Although some examples are provided of a mounting feature, examples are not so limited and may include other types of mounting features.

In some embodiments, the magnetic position sensor 209 can be disposed at a distal end of the central arm 126-5. The magnetic position sensor 209 can sense a position and/or orientation with five degrees of freedom (5 DOF) or six degrees of freedom (6 DOF), in some embodiments. As further discussed herein, one or more magnetic position sensors 134-1, 134-2 (FIG. 3B) can be disposed within the proximal coupler 128 and/or along a catheter shaft connected thereto (not depicted) and can be electrically coupled to the computer system 20 via wires 154-1, 154-2 (e.g., twisted pairs of wires). The magnetic position sensors 209, 134-1, 134-2 can be disposed in a magnetic field and can produce one or more signals, which can be indicative of the position and/or orientation of the magnetic position sensors 209, 134-1, 134-2.

In some embodiments, a longitudinal length of the flexible tip portion 122 can be such that a position of the distal end of the flexible tip portion 122 may not be determined by a magnetic position sensor positioned at a distal end of the catheter shaft. For example, the distal portion of the flexible tip portion 122 can extend beyond a region of magnetically correct position information and software used in a location determination of the flexible tip portion. Thus, a position and/or orientation of the flexible tip portion 122 may not be able to be accurately determined. Accordingly, a position and/or orientation of the magnetic position sensor 209 disposed in the distal end of the flexible tip portion 122 can be determined, the position of which can be used to determine the position and/or orientation of the distal end of the flexible tip portion 122, which may extend beyond a region of magnetically correct position information.

In some embodiments, the magnetic position sensor 209 may be disposed on a portion of the flexible tip portion 122, which is beyond the region of magnetically correct position information provided by the one or more magnetic position sensors 134-1, 134-2 disposed on the proximal coupler 128 and/or disposed on a distal end of the catheter shaft, from which the flexible tip portion 122 extends. Although the location of the magnetic position sensor 209 is generally discussed as being disposed on the central arm 126-5, the magnetic position sensor 209 can be located at other positions along the flexible tip portion 122 to enable determination of the location of the flexible tip portion 122.

In some embodiments, the central electrode 130 can be cylindrical in shape and can extend distally from the central arm 126-5. The central electrode 130 can house the magnetic position sensor 209 (FIG. 3J), while additionally providing the functionality of an electrode, which can be used for diagnostic and/or therapeutic purposes, as discussed herein. The central electrode 130 can be connected at a distal end to the distal coupler 136. The distal coupler 136 can couple a distal end of the central arm 126-5, a distal end of the first and second outboard arms 126-1, 126-4, and a distal end of the first and second inboard arms 126-2, 126-3. As previously mentioned, while the distal coupler 136 is depicted in relation to FIG. 3A, the distal coupler 136 is not required. For example, a framework that forms the flexible tip portion 122 of the high-density electrode catheter 120 may not be coupled together at a location distal to the distal end of the proximal coupler 128 and/or catheter shaft from which the flexible tip portion 122 extends. In some embodiments, although not depicted, a magnetic position sensor can be disposed on one or more portions of the uncoupled framework to enable determination of the location of the uncoupled framework and/or one or more portions of the uncoupled framework.

In some embodiments, although not depicted, the central electrode 130 can include one or more electrodes that are disposed on an exterior of the magnetic position sensor 209. For example, in some embodiments, the central electrode 130 can be divided into multiple portions (e.g., top half, bottom half) that are disposed about the central electrode 130. In some embodiments, one or more spot electrodes can disposed on the magnetic position sensor 209. In some embodiments, the central electrode 130 can be formed from a flexible circuit, which includes one or more electrodes formed thereon, which can be disposed over the magnetic position sensor 209.

In some embodiments, the central arm 126-5 can include a lengthening feature 140. As depicted in FIG. 3A, the lengthening feature 140 can include a non-linear lengthening feature 140. The non-linear lengthening feature 140 can include a bend in a portion of the central arm 126-5, which can be straightened, allowing for a longitudinal length of the central arm 126-5 to increase, when the bend is in a straightened configuration. For example, the high-density electrode catheter 120 can be introduced into a body via a sheath, in some embodiments. While disposed in the sheath, the high-density electrode catheter 120 can be in a stored state, where a distance between each one of the longitudinally extending arms is decreased. This can cause a stored longitudinal length of the flexible tip portion 122 to increase, versus a deployed length of the device, as depicted in FIG. 3A.

As depicted, the first and second outboard arms 126-1, 126-4 and the first and second inboard arms 126-2, 126-3 have bends (e.g., elbows) along their longitudinal length, causing them to flare laterally. For example, with respect to the second outboard arm 126-4, the arm includes a proximal bend 142-1 and a distal bend 142-2. When these bends 142-1, 142-2 straighten, as a result of the flexible tip portion 122 being collapsed into a stored state, the longitudinal length of the second outboard arm 126-4 can increase. By including the lengthening feature 140 on the central arm 125-5, which in this embodiment includes a non-linear lengthening feature 140, the central arm 125-5 can lengthen with the first and second outboard arms 126-1, 126-4 and the first and second inboard arms 126-2, 126-3, thus preventing the central arm 126-5 from pulling the flexible tip portion 122 out of alignment when in a stored state. Without the lengthening feature 140, in a stored state the length of the first and second outboard arms 126-1, 126-4 and the first and second inboard arms 126-2, 126-3 would lengthen, while the length of the central arm 126-5 would remain the same, causing a portion of the flexible tip portion 122 to fold over onto itself.

As depicted, the proximal coupler 128 can include a distal coupler head 144. In some embodiments, the distal coupler head 144 can be an irrigated distal coupler head 144. In some embodiments, the distal coupler head 144 can include one or more irrigation ports 146-1, 146-2 that are configured to discharge a fluid (e.g., an irrigation fluid). For example, in some embodiments, the irrigation ports 146-1, 146-2 can be disposed such that they distribute fluid in a manner that substantially covers the flexible tip portion 122. In some embodiments, the irrigation ports 146-1, 146-2 can be configured to distribute fluid over the flexible tip portion 122 to help prevent coagulation of blood or accumulation of other material on the flexible tip portion 122. In some embodiments, one or more portions of the flexible tip portion 122 can be susceptible to coagulation of blood. Accordingly, embodiments of the present disclosure can be configured to distribute fluid to one or more of these portions of the flexible tip portion 122, to prevent coagulation of blood. In some embodiments, the irrigation features associated with the proximal coupler 128 and its distal coupler head 144 can include one or more features discussed in relation to U.S. patent application Ser. No. 15/585,859, which is hereby incorporated by reference as though fully set forth herein.

As depicted in relation to FIG. 3A, the proximal coupler 128 can include a connective stem portion 150, which can be inserted into a lumen defined by a catheter shaft. In some embodiments, the connective stem portion 150 can define first and second sensor grooves 148-1, 148-2 (FIG. 3B) defined in an outer surface 152 of the connective stem portion 150. In some embodiments, the first and second sensor grooves 148-1, 148-2 can be angled with respect to one another and/or with respect to a longitudinal axis of the high-density electrode catheter 120. In some embodiments, the first and second sensor grooves 148-1, 148-2, as well as the magnetic position sensors 134-1, 134-2 can include those features discussed in relation to U.S. patent application Ser. No. 15/585,859, which is hereby incorporated by reference as though fully set forth herein. The configuration of the magnetic position sensors 134-1, 134-2 can allow for the position and/or orientation of the proximal coupler 128 and thus the high-density electrode catheter 120 to be determined with six degrees of freedom.

In some embodiments, although not depicted, additional electrodes can be disposed along distal portions of the arms 126-1, 126-2, 126-3, 126-4, as indicated by arrows 156-1, 156-2. For example, although FIG. 3A depicts the electrodes 124 linearly aligned with one another along the linear portions of the arms 126-1, 126-2, 126-3, 126-4, embodiments of the present disclosure can benefit from additional electrodes disposed along the regions of the arms 126-1, 126-2, 126-3, 126-4 indicated by arrows 156-1, 156-2.

In some embodiments, the electrodes disposed on the high-density electrode catheter 120 (e.g., one or more of electrodes 124, 130) may be used for a variety of diagnostic and/or therapeutic purposes including, for example and without limitation, cardiac mapping and/or ablation. In some embodiments, ablation performed by the electrodes can include multiple different types of ablation. For example, ablation performed by the electrodes can include unipolar and/or bipolar radiofrequency ablation and/or electroporation, as previously discussed herein.

In some embodiments, the flexible tip portion 122 can be an electrode assembly that is configured as a bipolar electrode assembly for use in bipolar-based electroporation therapy. Specifically, as described above, one or more of the electrodes 124 disposed on the flexible frame work and/or central electrode 130 can be individually electrically coupled to generator 56 (e.g., via suitable electrical wire or other suitable electrical conductors extending through catheter shaft 44), depicted in FIG. 1B, and are configured to be selectively energized (e.g., by an electroporation generator 56 and/or computer system 64) with opposite polarities to generate a potential and corresponding electric field therebetween, for IRE therapy. That is, one or more of electrodes 124, 130 are configured to function as a cathode, and the other is configured to function as an anode. One or more of electrodes 124, 130 may be any suitable electroporation electrodes. In the exemplary embodiment, one or more of electrodes 124, 130 can be ring electrodes. One or more of electrodes 124, 130 may have any other shape or configuration.

It is realized that the shape, size, and/or configuration of the one or more of electrodes 124, 130 may impact various parameters of the applied electroporation therapy. For example, increasing the surface area of one or more of electrodes 124, 130 may reduce the applied voltage needed to cause the same level of tissue destruction. Although only electrode 124 is reference in discussion, the discussion herein can apply to any one of the electrodes depicted on the flexible tip portion 122 of the high-density electrode catheter 120. While electrodes 124, 130 disposed on the flexible tip portion 122 are described as a bipolar electrode assembly, it should be understood that in some embodiments, the electrodes 124, 130 disposed on the flexible tip portion 122 may be configured as a monopolar electrode assembly and use a patch electrode (e.g., return electrode 50) as a return or indifferent electrode.

Figure 3C:
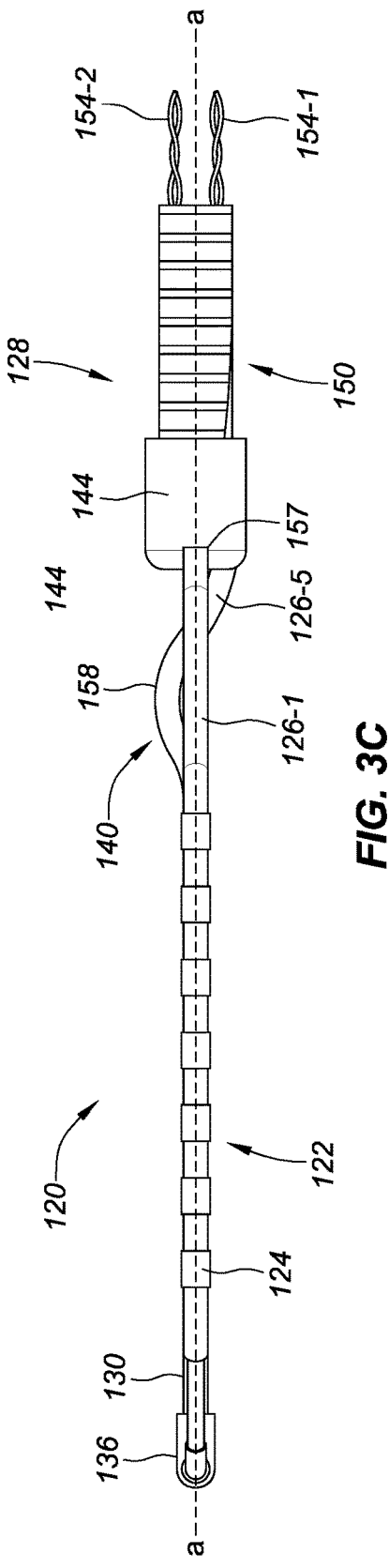
FIG. 3C is a side view of the high-density electrode catheter depicted in FIGS. 3A and 3B, in accordance with embodiments of the present disclosure.

FIG. 3C is a side view of the high-density electrode catheter 120 depicted in FIGS. 3A and 3B, in accordance with embodiments of the present disclosure. As depicted, the flexible tip portion 122 can extend distally from the proximal coupler 128. In some embodiments, the distal end of the distal coupler head 144 can include a cross-longitudinal slot 157 through which the first and second outboard arms 126-1, 126-4 and the first and second inboard arms 126-2, 126-3 can extend. As further depicted, the first and second outboard arms 126-1, 126-4 and the first and second inboard arms 126-2, 126-3 can extend distally from the distal coupler head 144 from a plane that bisects a longitudinal axis a-a of the distal coupler head 144 and the connective stem portion 150.

In some embodiments, the central arm 126-5 can extend from the distal coupler head 144, below the longitudinal axis a-a and below the location where the first and second outboard arms 126-1, 126-4 and the first and second inboard arms 126-2, 126-3 extend from the distal coupler head 144. In some embodiments, the central arm 126-5 can include the lengthening feature 140. For example, the central arm 126-5 can exit the distal end of the distal coupler head 144 and can extend distally and upward, rising through a plane defined by the first and second outboard arms 126-1, 126-4 and the first and second inboard arms 126-2, 126-3. With reference to FIG. 3C, the longitudinal axis a-a can extend through the plane defined by the first and second outboard arms 126-1, 126-4 and the first and second inboard arms 126-2, 126-3. The central arm 126-5 can then extend downward toward the plane defined by the arms 126-1, 126-2, 126-3, 126-4, after reaching a peak 158. As previously discussed, when the flexible framework is in a stored configuration, the longitudinal length of the arms 126-1, 126-2, . . . , 126-5 can extend and the curvature in the lengthening feature 140 can flatten, allowing for the central arm 126-5 to extend.

Figure 3D:
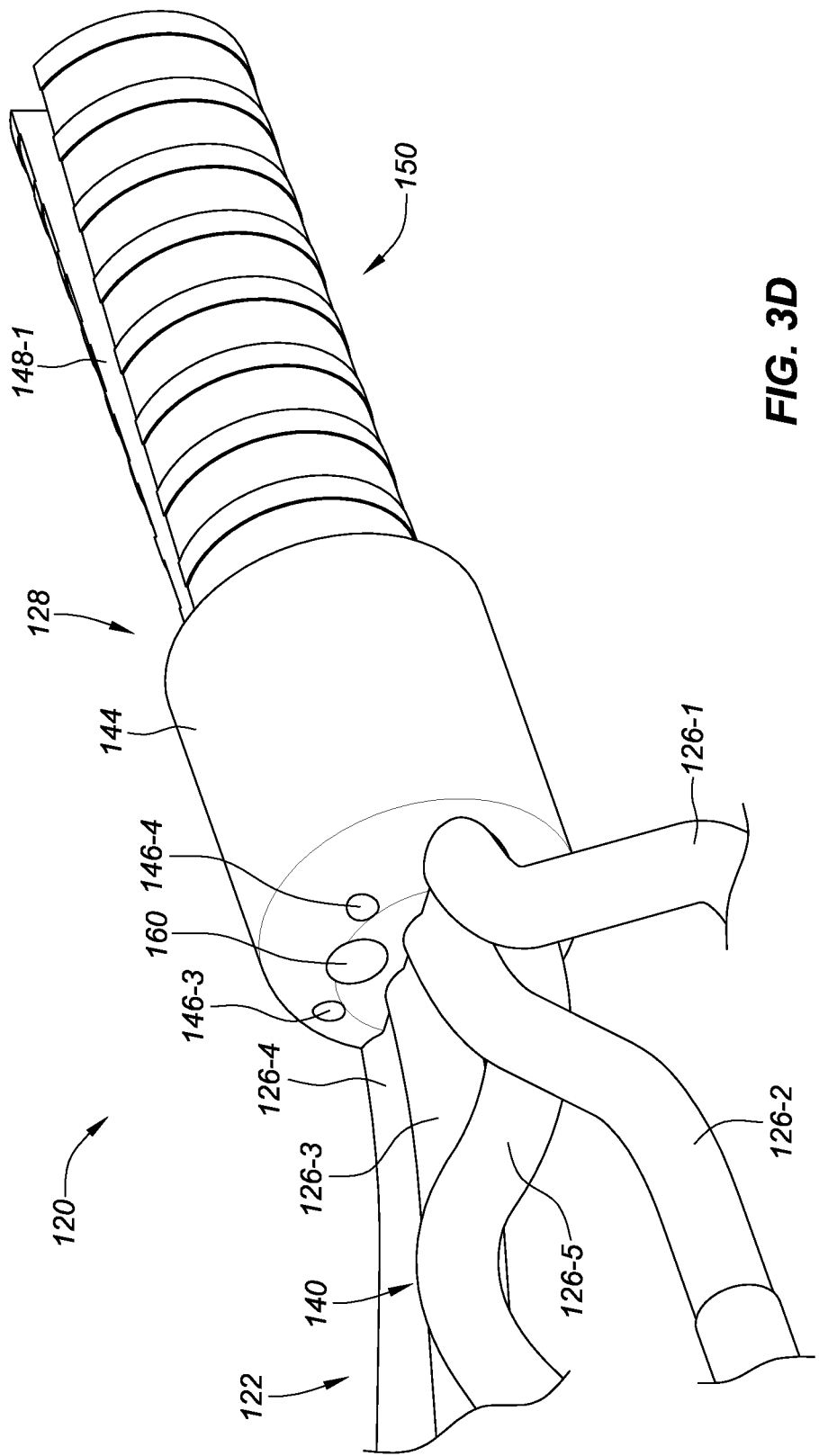
FIG. 3D is an isometric side and bottom view of the high-density electrode catheter depicted in FIGS. 3A to 3C, in accordance with embodiments of the present disclosure.

FIG. 3D is an isometric side and bottom view of the high-density electrode catheter 120 depicted in FIGS. 3A to 3C, in accordance with embodiments of the present disclosure. FIG. 3D depicts third and fourth irrigation ports 146-3, 146-4 that are defined in a distal face of the distal coupler head 144. In some embodiments, the distal coupler head 144 can define a lumen 160 in which an adhesive can be injected to fill an inner cavity which houses proximal connective portions of the understructures of the arms 126-1, 126-2, . . . , 126-5, as further depicted herein. In some embodiments, the lumen 160 can allow for insertion of a sixth arm in an embodiment where the flexible tip portion includes six arms, as depicted and discussed in relation to FIG. 5A.

Figure 3E:
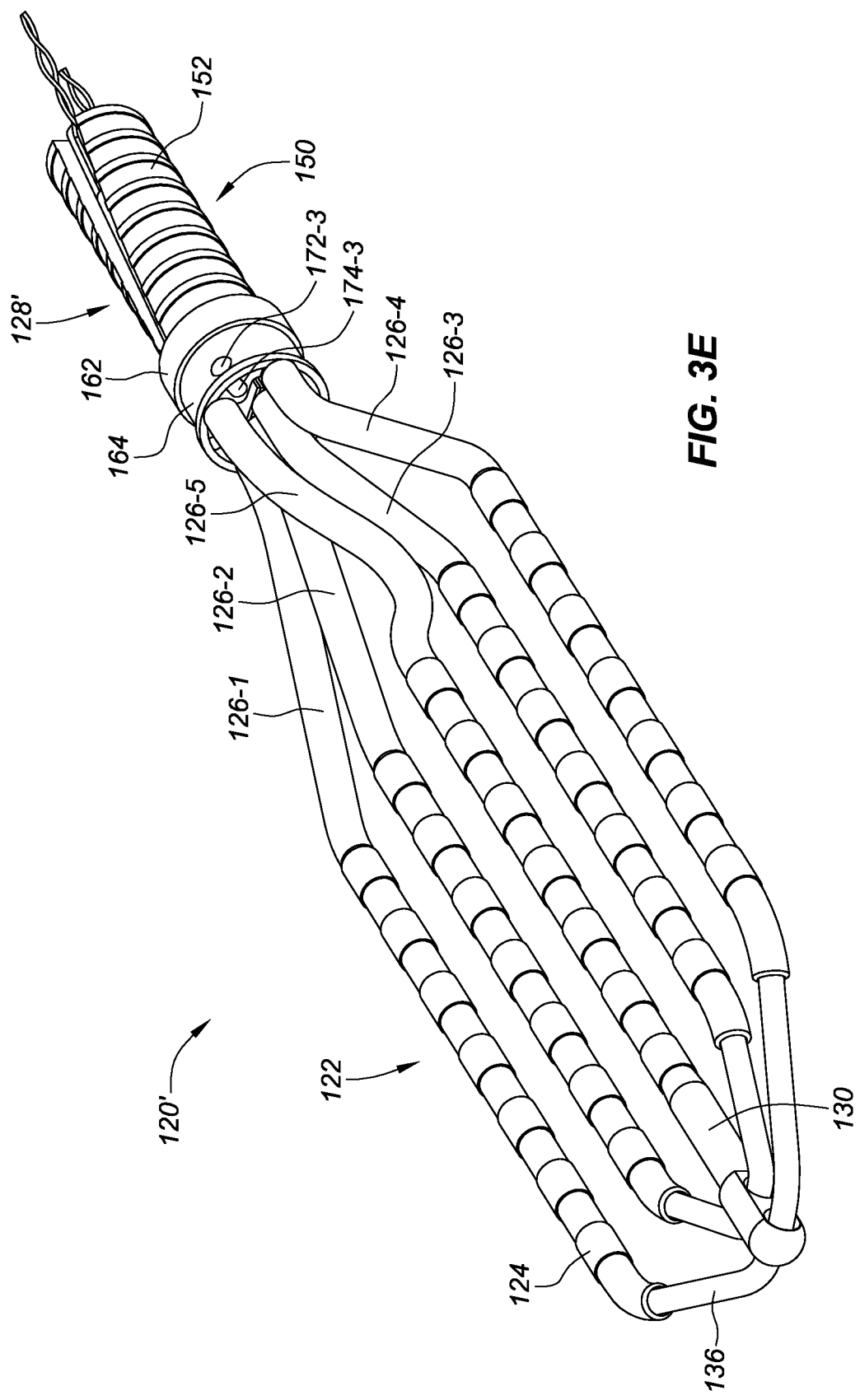
FIG. 3E is an isometric top and side view of the high-density electrode catheter depicted in FIGS. 3A to 3D, further depicting a manifold portion, in accordance with embodiments of the present disclosure.
Figure 3F:
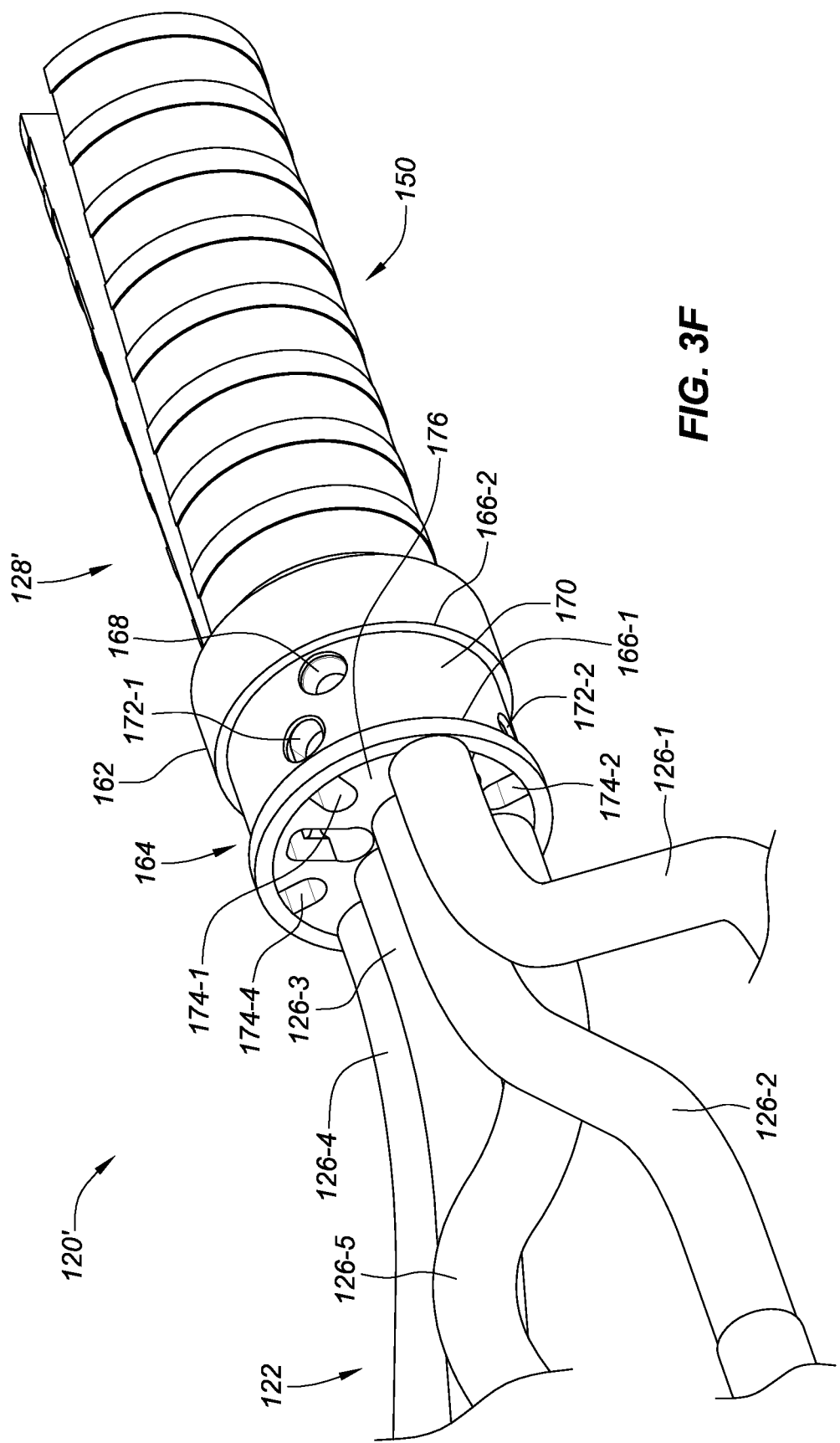
FIG. 3F is an isometric bottom and side view of the high-density electrode catheter depicted in FIGS. 3A to 3E, further depicting the manifold portion in FIG. 3E, in accordance with embodiments of the present disclosure.

FIG. 3E is an isometric top and side view of the high-density electrode catheter 120' depicted in FIGS. 3A to 3D, further depicting a manifold portion 162, in accordance with embodiments of the present disclosure. FIG. 3F is an isometric bottom and side view of the high-density electrode catheter 120' depicted in FIGS. 3A to 3E, further depicting the manifold portion 162, in accordance with embodiments of the present disclosure. In some embodiments, a manifold portion 162 can direct fluid to each one of the irrigation port that are defined in the distal face of the distal coupler head 144. In some embodiments, the manifold portion 162 can be a hollow cylindrical tube that extends over a distal end of the connective stem portion 150 and/or a mounting portion 176 (FIG. 3G).

The manifold portion 162 can define a circumferential manifold 164 that is defined in an exterior surface of the manifold portion 162. As depicted, the circumferential manifold 164 can circumferentially extend about the manifold portion 162 and can be defined by a recessed manifold portion 170, an inner face of the distal coupler head 144, as well as manifold walls 166-1, 166-2. As depicted in FIG. 3F, manifold walls 166-1, 166-2 can define the proximal and distal ends of the circumferential manifold 164 and can be fluidly sealed with an inner surface of the distal coupler head 144.

In some embodiments, a fluid lumen can be defined in the connective stem portion 150, as further depicted and discussed herein. The fluid lumen can be in fluid communication with a fluid input 168, which can be defined in the recessed manifold portion 170 and can extend between an inner surface of the manifold portion 162 and the outer surface of the recessed manifold portion 170. In an example, the fluid can be input into the circumferential manifold 164 by the fluid input 168, filling the circumferential manifold 170 with fluid. The recessed manifold portion 170 can further define fluid outputs 172-1, 172-2, 172-3, 172-4 (fluid output 172-4 is hidden from view). Each one of the fluid outputs 172-1, 172-2, 172-3, 172-4 can be fluidly coupled with a fluid duct 174-1, 174-2, 174-3, 174-4, respectively.

Figure 3H:
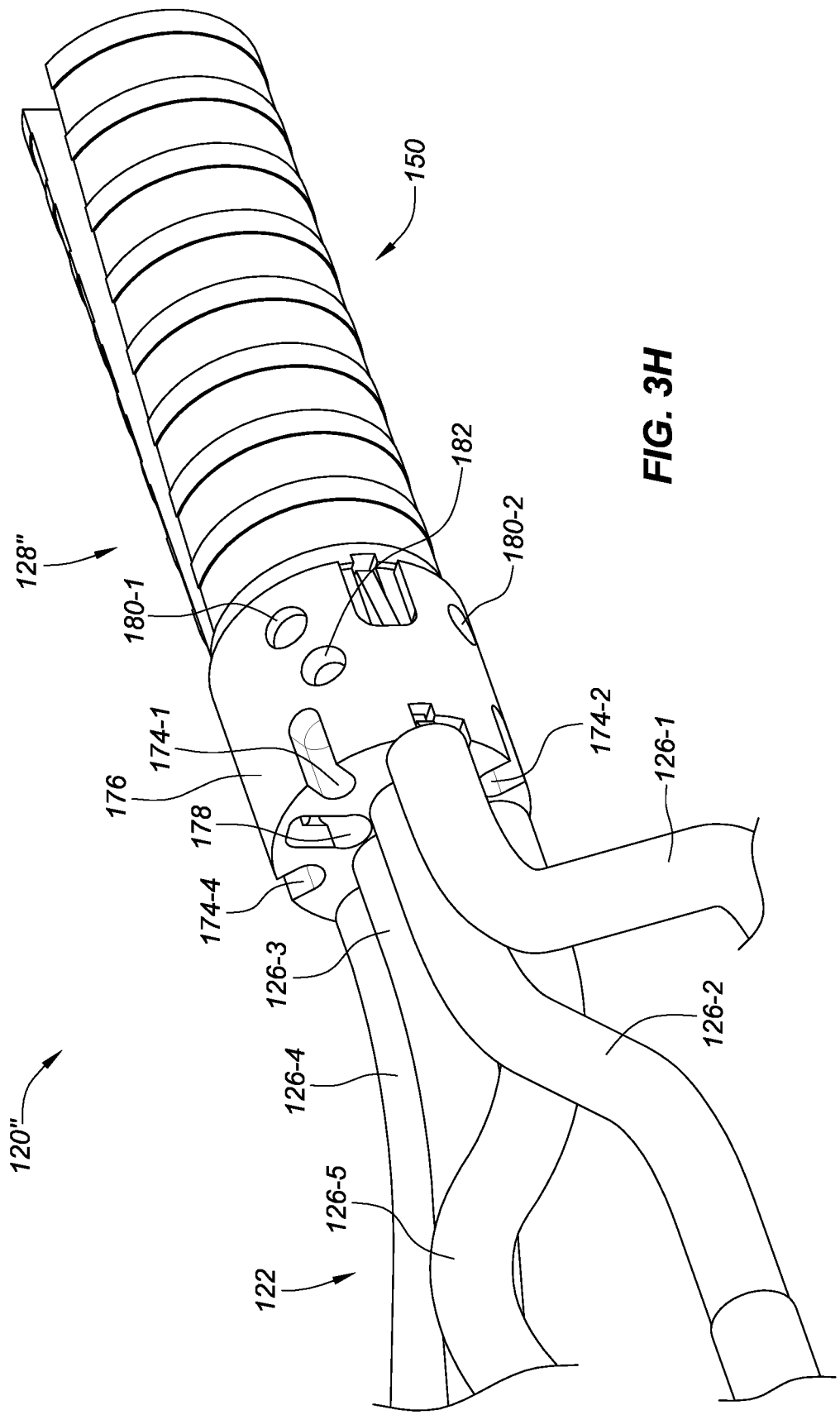
FIG. 3H is an isometric bottom and side view of the high-density electrode catheter depicted in FIGS. 3A to 3G, further depicting the mounting portion in FIG. 3G, in accordance with embodiments of the present disclosure.

The fluid ducts 174-1, 174-2, 174-3, 174-4 can be defined in a mounting portion 176, which is further discussed in relation to FIG. 3G. As depicted in FIG. 3F, each one of the ducts 174-1, 174-2, 174-3, 174-4 can be defined in a distal face of the mounting portion 176. FIG. 3G is an isometric top and side view of the high-density electrode catheter 120" depicted in FIGS. 3A to 3F, further depicting a mounting portion 176, in accordance with embodiments of the present disclosure. FIG. 3H is an isometric bottom and side view of the high-density electrode catheter 120" depicted in FIGS. 3A to 3G, further depicting the mounting portion 176, in accordance with embodiments of the present disclosure. The mounting portion 176 can be disposed on a distal end of the connective stem portion 150, in some embodiments. As depicted, the mounting portion 176 can be cylindrical in shape and can define the ducts 174-1, 174-2, 174-3, 174-4 through which the irrigation fluid can flow and can be directed out of the irrigation ports 146-1, 146-2, 146-3, 146-4 (FIGS. 3A and 3D).

In some embodiments, the mounting portion 176 can define a receiving lumen in which the connective stem portion 150 can be received. In some embodiments, a plurality of adhesive holes 180-1, 180-2, 180-3, 180-4 (180-4 is hidden from view) can be defined in an exterior surface of the mounting portion 176. An adhesive can be injected into the adhesive lumen 178 and the adhesive can flow through an interior portion of the mounting portion 176 and into the adhesive holes 180-1, 180-2, 180-3, 180-4, thus securing the mounting portion 176 to the connective stem portion 150 and the manifold portion 162 (FIG. 3F). As further depicted, proximal ends of the arms 126-1, 126-2, . . . , 126-5 can be disposed within a distal end of the mounting portion 176 such that they are secured in place with respect to the mounting portion 176.

Figure 3I:
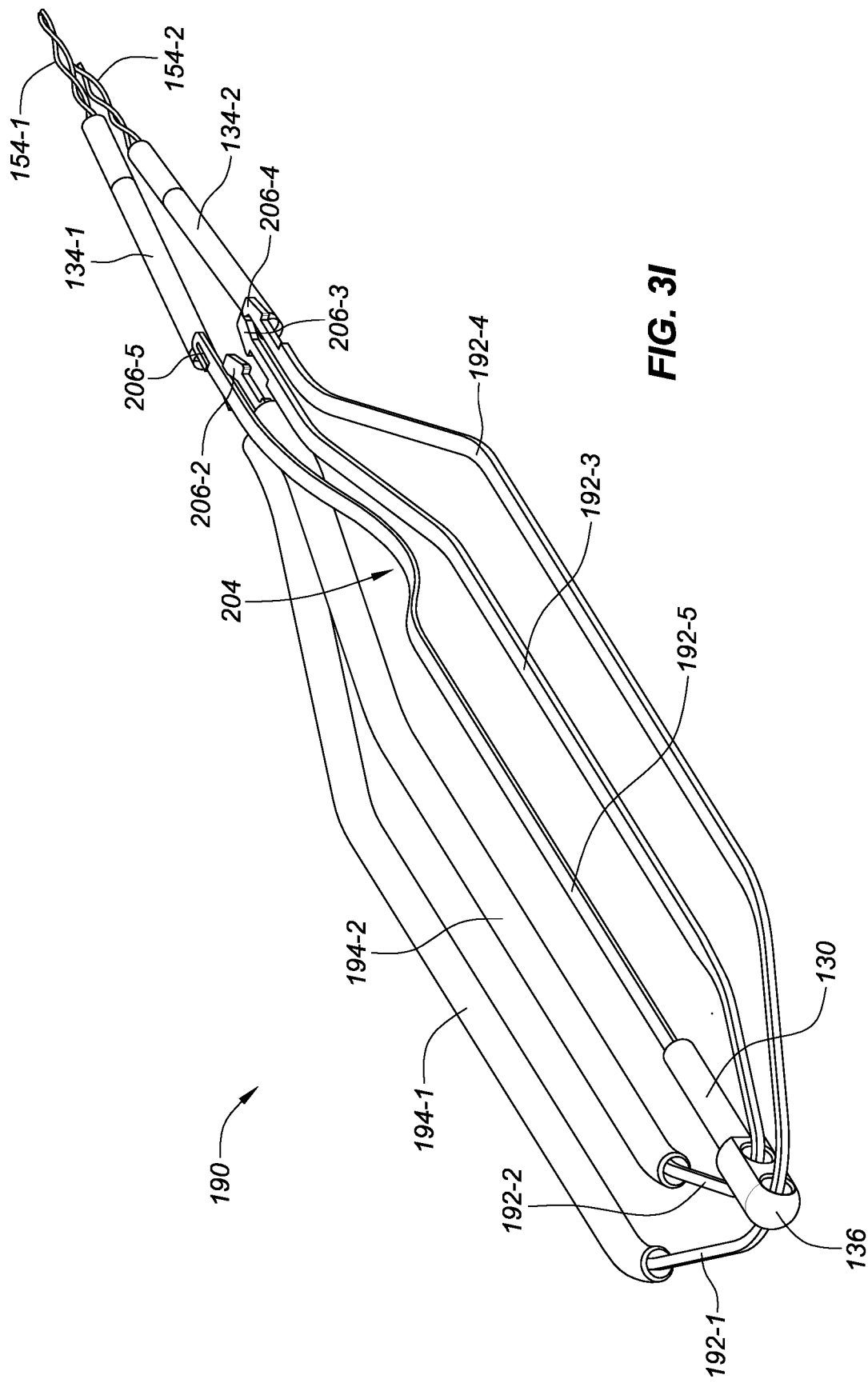
FIG. 3I is an isometric top and side view of a flexible understructure of the high-density electrode catheter depicted herein, in accordance with embodiments of the present disclosure.
Figure 3L:
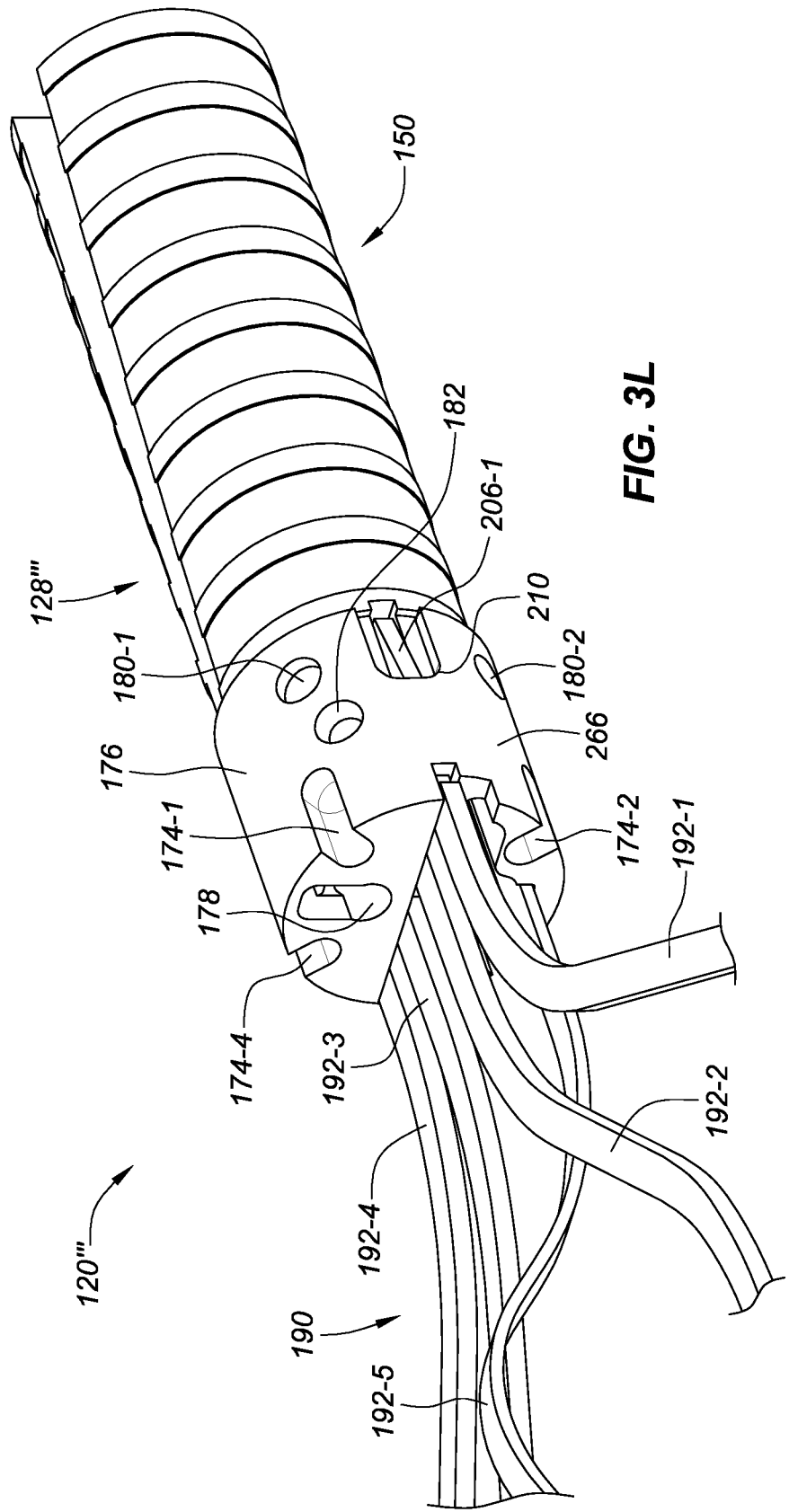
FIG. 3L is an isometric bottom and side view of the high-density electrode catheter depicted in FIG. 3H, without the tubes covering the flexible understructure, in accordance with embodiments of the present disclosure.
Figure 3M:
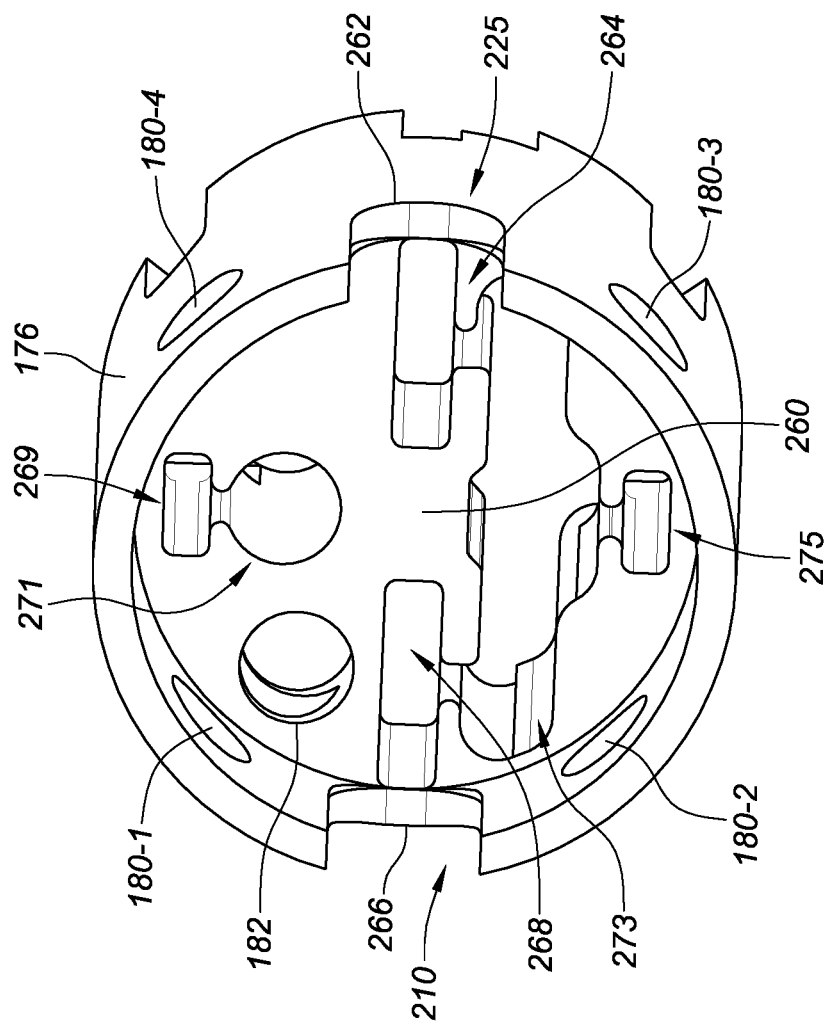
FIG. 3M is an isometric proximal end view of the mounting portion depicted in FIGS. 3G and 3H, in accordance with embodiments of the present disclosure.

In some embodiments, the mounting portion 176 can include an irrigation thru hole 182, which is further depicted in FIG. 3M. The irrigation thru hole 182 can be fluidly coupled with an irrigation lumen 280 (FIG. 3Q) that is defined in the connective stem portion 150. For example, the irrigation lumen 280 can be defined in and can extend longitudinally through the connective stem portion 150. The irrigation lumen 280 can provide irrigation fluid to the thru hole 182 and thus to the fluid input 168.

FIG. 3I is an isometric top and side view of a flexible understructure 190 of the high-density electrode catheter 120 depicted herein, in accordance with embodiments of the present disclosure. FIG. 3J is an isometric bottom and side view of a flexible understructure 190 of the high-density electrode catheter depicted in FIGS. 3A to 3I, in accordance with embodiments of the present disclosure. The flexible understructure 190 can include a first outboard frame 192-1, a first inboard frame 192-2, a central frame 192-5, a second inboard frame 192-3, and a second outboard frame 192-4. The first outboard frame 192-1 and the first inboard frame 192-2 are depicted as being covered by respective tubes 194-1, 194-2, through which the first outboard frame 192-1 and the first inboard frame 192-2 pass. In some embodiments, the tubes 194-1, 194-2 can be bi-lumen tubes, as further depicted in FIG. 3K, allowing for a frame 192-1 to pass through a first lumen 198 of the bi-lumen tube and a plurality of wires 196 to pass through a second lumen 200 of the bi-lumen tube, which is separated from the first lumen 198 via a planar cross member 202.

With further reference to FIG. 3I, the central frame 192-5 can include a non-linear lengthening feature 204, as previously discussed herein, which allows for the central frame 192-5 to lengthen when the outboard frames 192-1, 192-4 and inboard frames 192-2, 192-3 lengthen in a stored configuration. As depicted, one non-linear lengthening feature 204 is depicted, however more than one non-linear lengthening features can be included along the central arm 192-5. For example, in some embodiments, a series of undulations can be included along the central arm 192-5, each of the series of undulations flattening out as the central arm 192-5 is elongated with the outboard frames 192-1, 192-4 and inboard frames 192-2, 192-3.

In some embodiments, the proximal end of each one of the frames 192-1, 192-2, . . . , 192-5 includes a frame mounting portion 206-1, 206-2, . . . , 206-5, which can engage the mounting portion 176, as discussed herein. The frames 192-1, 192-2, . . . , 192-5 can be formed from a flexible material, which can include a metal (e.g., nitinol) in some embodiments. As further depicted, the frames 192-1, 192-2, . . . , 192-5 can include a planar cross-section, as further discussed in relation to U.S. application Ser. No. 15/331,369 entitled High Density Electrode Mapping Catheter, which is hereby incorporated by reference as though fully set forth herein. In some embodiments, the frame mounting portions 206-1, 206-2, . . . , 206-5 can be disposed in corresponding openings and/or lumens defined in the mounting portion 176, as further discussed herein with respect to FIG. 3M.

FIG. 3L is an isometric bottom and side view of the high-density electrode catheter 120''' depicted in FIG. 3H, without the tubes 194 covering the flexible understructure 190, in accordance with embodiments of the present disclosure. As can be seen, the proximal end of each one of the frames 192-1, 192-2, . . . , 192-5 can be disposed within the mounting portion 176. For example, as depicted, a side of frame mounting portion 206-1 visibly protrudes within a mounting cutout 210 defined in the proximal end of the mounting portion 176. As depicted, the mounting cutout 210 can be an opening (e.g., slot) that extends distally from a proximal end of the mounting portion 176 that has a circumferential width that is at least as great as a thickness of the frame mounting portion 206-1. As depicted in FIG. 3M, the opposite side of the mounting portion 176 can include a mounting cutout 225.

FIG. 3M is an isometric proximal end view of the mounting portion 176, in accordance with embodiments of the present disclosure. As depicted, the mounting portion 176 defines the adhesive holes 180-1, 180-2, 180-3, 180-4 through which adhesive can be disposed to secure the mounting portion 176, as discussed herein. As further depicted, the mounting portion 176 can includes the irrigation thru hole 182, through which an irrigation fluid can flow and be distributed by the manifold portion 162 (FIG. 3F). Further aspects of the mounting portion are discussed in relation to FIG. 3P.

Figure 3N:
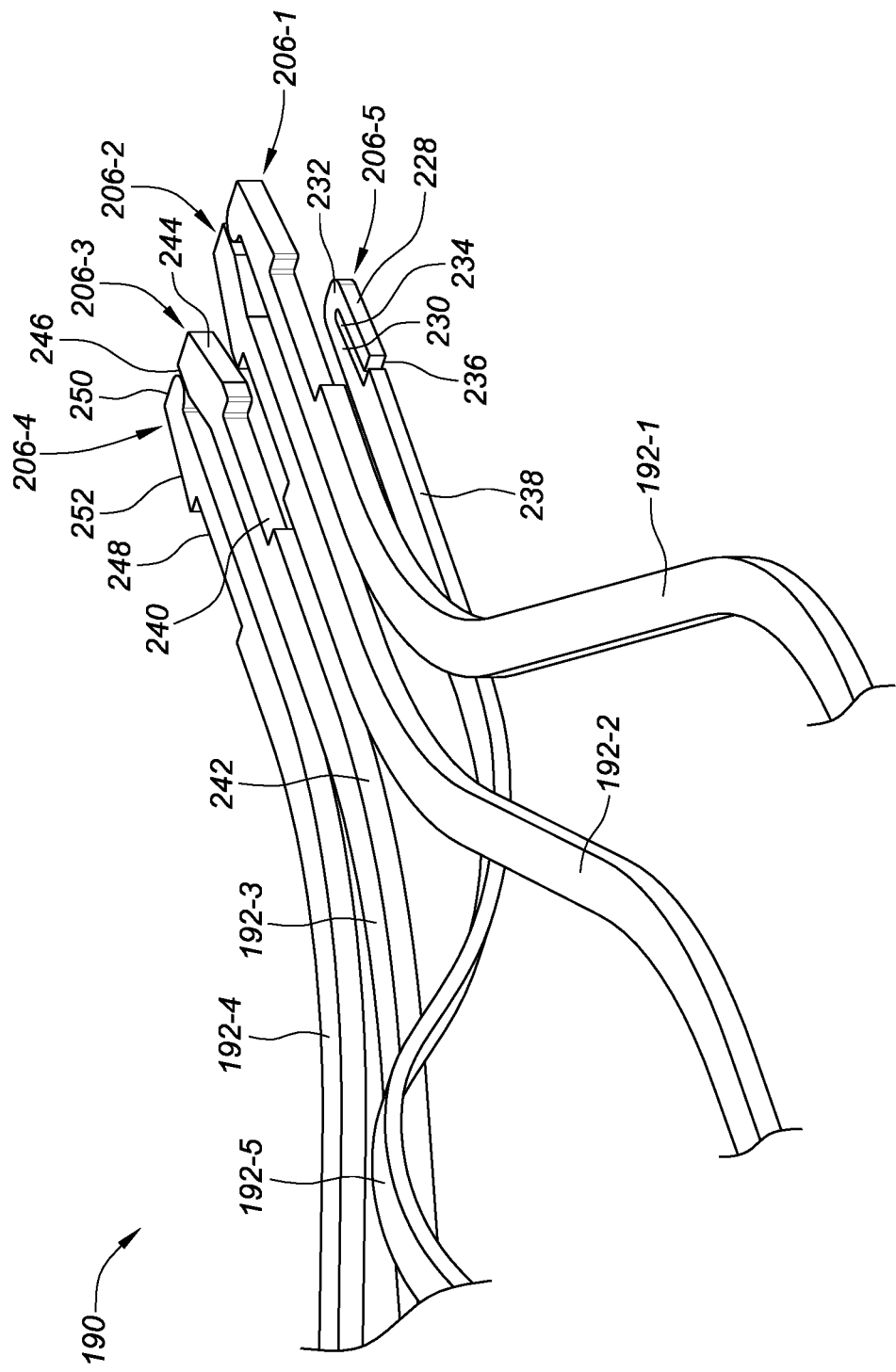
FIG. 3N is an isometric bottom and side view of the proximal end of the flexible understructure, in accordance with embodiments of the present disclosure.
Figure 30:
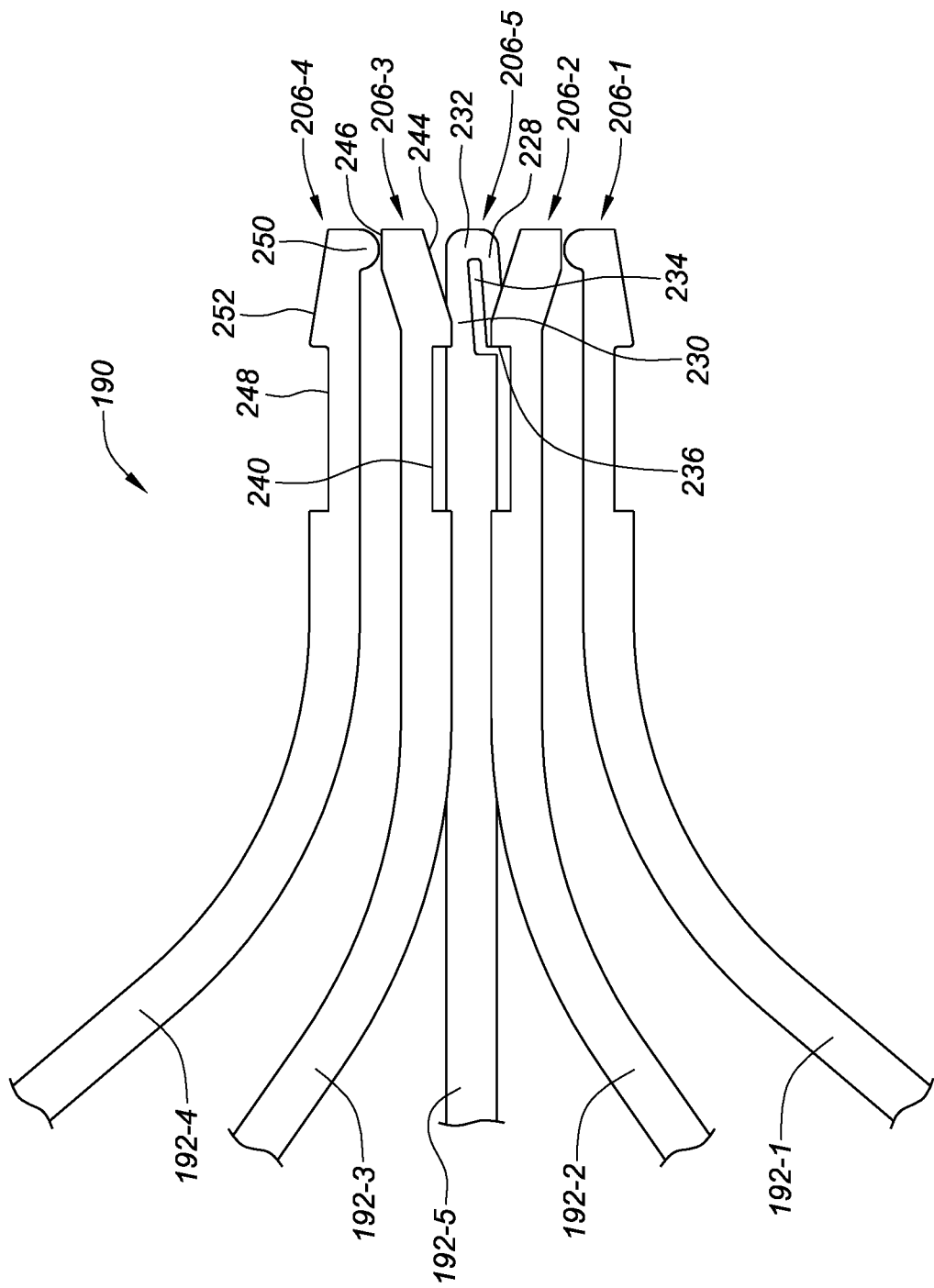

FIG. 3N is an isometric bottom and side view of the proximal end of the flexible understructure 190, in accordance with embodiments of the present disclosure. FIG. 3M is a bottom view of the proximal end of the flexible understructure 190, in accordance with embodiments of the present disclosure. As depicted, the proximal end of each one of the frames 192-1, 192-2, . . . , 192-5 can include frame mounting portion 206-1, 206-2, . . . , 206-5. The frame mounting portions 206-1, 206-2, . . . , 206-5 can be configured to engage with the mounting portion 176, in order to cause the frame mounting portions 206-1, 206-2, . . . , 206-5 and thus the frames 192-1, 192-2, . . . , 192-5 to be locked into place with respect to the mounting portion 176. In some embodiments, the frame mounting portions 206-1, 206-2, . . . , 206-5 can include clip portions that utilize a spring tension provided by the frames 192-1, 192-2, . . . , 192-5 to engage corresponding clip portions defined in the mounting portion 176. In some embodiments, a flexibility associated with the frames 192-1, 192-2, . . . , 192-5 can provide the spring tension.

In some embodiments, with respect to the central frame 192-5, the central frame mounting portion 206-5 can include a spring clip 228. As depicted, a spring post 230 can extend proximally with respect to the central frame 192-5 and can be connected at its proximal end to the spring clip 228 via a spring connector. In some embodiments, a spring gap 234 can be defined between the spring post 230 and the spring clip 228. In operation, the spring gap 234 can provide room for the spring clip 228 to be compressed towards the spring post 230 as the central frame mounting portion 206-5 is pushed through a mounting lumen 269 (FIG. 3M), as further discussed herein. As further discussed, the mounting lumen 269 can have a complementary shape with respect to a cross-section of the central frame 192-5, allowing for the central frame mounting portion 206-5 to be pushed through the mounting lumen 269.

With further reference to FIG. 3O, the spring clip distal end 232 of the spring clip 228 can protrude past a corresponding frame edge 238 when the spring clip 228 is in an engaged configuration. When the spring clip 228 is being pushed through a corresponding mounting lumen 269 (FIG. 3M), the spring clip 228 can be pushed towards the spring post 230, causing the spring clip distal end 232 to become more flush with the corresponding frame edge 238, thus allowing the central frame mounting portion 206-5 to be pushed through mounting lumen 269.

With respect to the first and second inboard frames 192-2, 192-3, their respective frame mounting portions 206-2, 206-3 can include frame clips, as depicted. For simplicity, discussion of the frame clips associated with the frame mounting portions is limited to the second inboard mounting portion 206-3. The first inboard mounting portion 206-2 can include the same or similar features the second inboard mounting portion 206-3. As depicted, the second inboard mounting portion 206-3 can include a clip cutout 240 that is defined in an inner edge 242 of the of the second inboard frame 192-3. In some embodiments, the clip cutout 240 can be complementary with respect to an inboard locking post 260 defined in the mounting portion 176, as further depicted and discussed herein with respect to FIG. 3P. For example, the inboard locking post 260 defined in the mounting portion 176 can be disposed in the clip cutout 240, thus locking the second inboard mounting portion 206-3 in place.

As further depicted, the second inboard mounting portion 206-3 can include a ramp portion 244, which can enable the second inboard mounting portion 206-3 to be deflected over the inboard locking post 260 when the second inboard frame 192-3 is pushed into the mounting portion 176. In some embodiments, the second inboard frame 192-3 and the first inboard frame 192-2 can be connected and thus can be simultaneously pushed into the mounting portion 176. As depicted, the first inboard mounting portion 206-2 and the second inboard mounting portion 206-3 can be deflected away from one another as their respective ramps contact the inboard locking post 260.

As depicted, the second inboard mounting portion 206-3 can further include a retaining shelf 246, which can be contacted by an engagement bump 250 disposed on an opposing proximal inner edge of the second outboard mounting portion 206-4, as discussed herein. With respect to the second outboard mounting portion 206-4, the second outboard mounting portion 206-4 can include similar features with respect to the second inboard mounting portion 206-3. For example, the second outboard mounting portion 206-4 can include a clip cutout 248 and ramp portion 252 for engagement with an outboard locking post 262 disposed in the mounting portion 176.

As further discussed herein, in some embodiments, the first and second inboard mounting portions 206-2, 206-3 can be inserted into the mounting portion 176 first, and then the first and second outboard mounting portions 206-1, 206-4 can be inserted. With respect to the second outboard mounting portion 206-4 and the second inboard mounting portion 206-3, the engagement bump 250 can press against the retaining shelf 246, thus causing a retaining force to be exerted between the engagement bump 250 and the retaining shelf 246, thereby ensuring that the clip cutouts 240, 248 remain engaged with their respective locking post 260, 262.

Figure 3P:
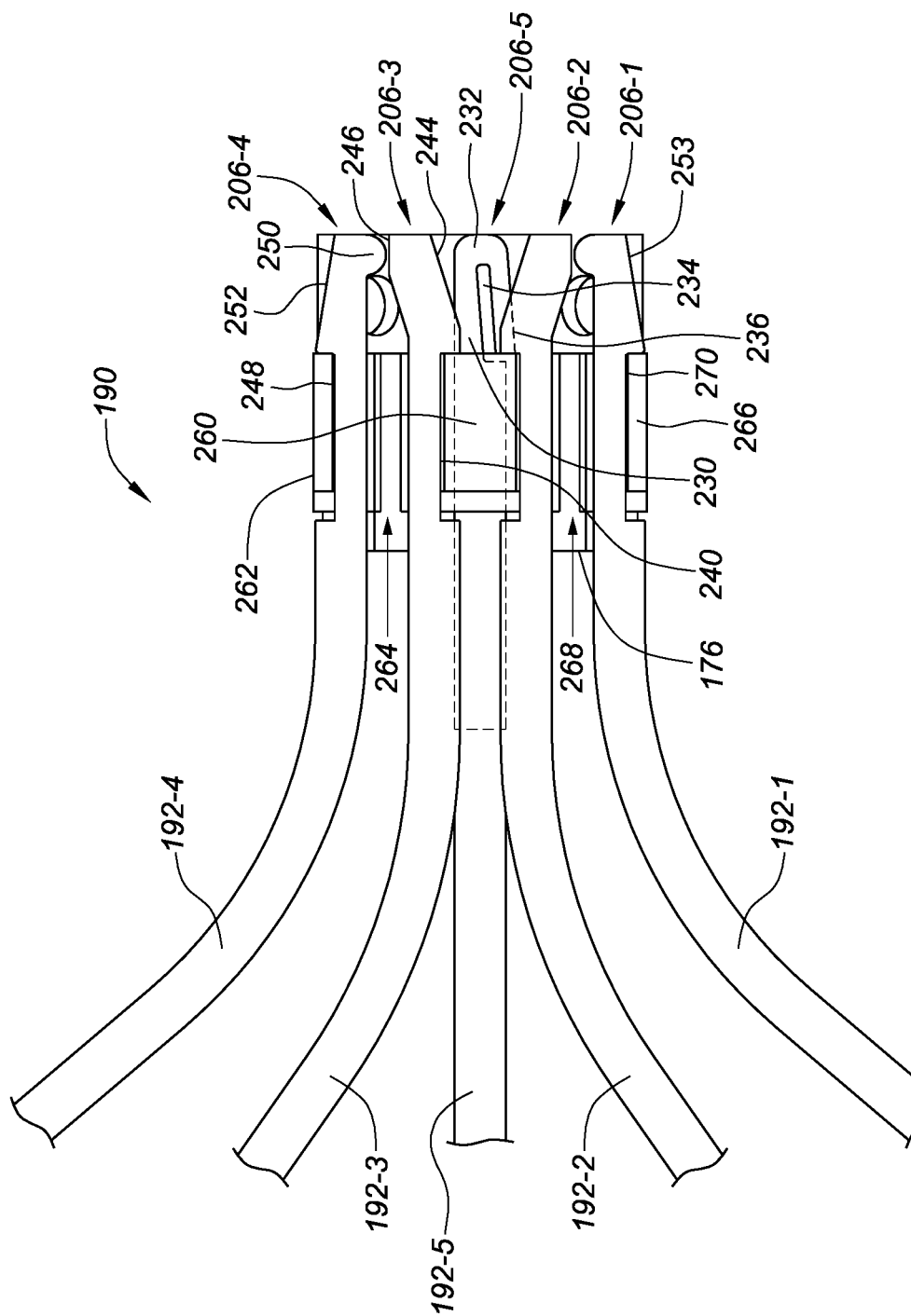
FIG. 3P is a bottom view of the proximal end of the flexible understructure disposed in the mounting portion, which is depicted via a cross-sectional view, in accordance with embodiments of the present disclosure.

FIG. 3P is a bottom view of the proximal end of the flexible understructure 190 disposed in the mounting portion 176, which is depicted via a cross-sectional view, in accordance with embodiments of the present disclosure. As depicted and as previously mentioned, the mounting portion can include an inboard locking post 260 and an outboard locking post 262. As discussed, in some embodiments, the first and second inboard frames 192-2, 192-3 can be inserted into the mounting portion 176. In some embodiments, extensions (e.g., wires) can be attached to proximal ends of each inboard and/or outboard mounting portion 206-1, 206-2, . . . , 206-4 and can be threaded through openings 264, 268, also depicted in FIG. 3M, defined between the inboard locking post 260 and the outboard locking posts 262, 266. In some embodiments, the extensions can be pulled proximally to help urge the inboard/outboard mounting portions 206-1, 206-2, . . . , 206-4 proximally into engagement with each respective inboard/outboard locking post 260, 262.

As discussed, in some embodiments, when the inboard mounting portions 206-2, 206-3 are urged into position, providing for the engagement between the clip cutout 240 and the inboard locking post 260, the ramp portion 244 can come into contact with an outboard distal edge of the locking post 260. Contact between the ramp portion 244 and the distal edge of the locking post 260 can cause the second inboard mounting portion 206-3 to separate from the first inboard mounting portion 206-2. Although not labeled, the ramp portion associated with the first inboard mounting portion 206-2 can contact a respective proximal edge of the locking post 260, also causing the first inboard mounting portion 206-2 to separate from the second inboard mounting portion 206-3. For example, in some embodiments, the first and second inboard frames 192-2, 192-3 can be naturally biased in the configuration depicted in FIG. 3P.

Upon insertion of the inboard mounting portions 206-2, 206-3 into the mounting portion 176, the first and second inboard frames 192-2, 192-3 can be deflected from their naturally biased state. When the first and second inboard frames 192-2, 192-3 are inserted into the mounting portion 176 to a point where their respective clip cutouts (e.g., clip cutout 240) aligns with the inboard locking post 260, the first and second inboard frames 192-2, 192-3 can return to their naturally biased state, locking them into place with respect to the inboard locking post 260.

In some embodiments, the first and second outboard frames 192-1, 192-4 can be inserted into the respective openings 264, 268 defined between the inboard locking post 260 and the outboard locking posts 262, 266. In some embodiments, the first and second outboard mounting portions 206-1, 206-4 can be inserted into the openings 264, 268 after the first and second inboard mounting portions 206-2, 206-3 have been inserted into the openings 264, 268 and are locked into place with the inboard locking post 260. Upon insertion of the first and second outboard mounting portions 206-1, 206-4 into their respective openings 264, 268, a ramp portion 252, 253 of each one of the first and second outboard mounting portions 206-1, 206-4 can contact an inboard distal edge of each one of the respective outboard locking posts 262, 266, deflecting the first and second outboard mounting portions 206-1, 206-4 inward toward one another.

Each of the first and second outboard mounting portions 206-1, 206-4 can be inserted proximally through the respective openings 264, 268, until the clip cutouts 248, 270 of each respective first and second outboard mounting portions 206-1, 206-4 is aligned with each outboard locking post 262, 266. Upon alignment of the outboard locking posts 262, 266 with each of the first and second clip cutouts 248, 270, the first and second outboard mounting portions 206-1, 206-4 can expand laterally, causing the first and second outboard locking posts 262, 266 to become seated in each clip cutout 248, 270.

As previously discussed, each one of the first and second outboard mounting portions 206-1, 206-4 can include an engagement bump 250. For simplicity, discussion of the engagement bump is limited to the second outboard mounting portion 206-4, although the first outboard mounting portion 206-1 includes the same or similar features. As depicted, upon insertion of the second outboard mounting portion 206-4 and engagement of the clip cutout 248 with the outboard locking post 262, the engagement bump 250 can engage the retaining shelf 246. In some embodiments, the engagement bump 250 can abut the retaining shelf 246, thus preventing both the clip cutouts 240, 248 from becoming unseated with their respective locking posts 260, 262.

As depicted in phantom, the central frame 192-5 can include central mounting portion 206-5. In some embodiments, the mounting portion 176 can define a mounting lumen 269 (FIG. 3M) that longitudinally extends through the mounting portion 176 and is similarly sized with respect to the cross-section of the central arm 192-5. In some embodiments, central mounting portion 206-5 can be advanced in a proximal direction through the longitudinally extending mounting lumen 269 in the mounting portion 176. As the central mounting portion 206-5 is advanced through the mounting lumen 269 in the mounting portion 176, the spring clip 236 can be compressed towards the spring post 230, until the spring clip passes through the mounting lumen 269, allowing the spring clip 236 to expand and thus locking the central mounting portion 206-5 into place, preventing the central mounting portion 206-5 from being distally pulled from the mounting lumen 269.

As further depicted in relation to FIG. 3M, in some embodiments, wire lumens 271, 273 can be defined in a distal face of the mounting portion 176. In some embodiments, the wire lumens 271 can provide space for the routing of wires to the flexible tip portion 122 (FIG. 3A), as discussed herein.

FIG. 3Q is an isometric distal end view of the connective stem portion 150, in accordance with embodiments of the present disclosure. FIG. 3R is an isometric proximal end view of the connective stem portion 150 depicted in FIG. 3G, in accordance with embodiments of the present disclosure. As depicted, the connective stem portion 150 can include an irrigation lumen 280 that extends therethrough. As previously discussed, the irrigation lumen 280 can provide irrigation fluid from a proximal end of the connective stem portion 150 to the fluid input 168, as discussed in relation to FIG. 3F. As further depicted, the connective stem portion 150 can define the first and second sensor grooves 148-1, 148-2, as discussed herein. The distal end of the connective stem portion 150 can include a tapered portion 284 through which a cross-longitudinal slot can be defined for insertion of a flexible framework. In some embodiments, the tapered portion can be joined with an inner surface of the manifold portion 162.

As depicted in FIG. 3Q, the irrigation lumen 280 can be defined in the proximal end of the connective stem portion 150, along with the first and second sensor grooves 148-1, 148-2. In some embodiments, the connective stem portion 150 can include a central lumen 286 that extends therethrough. As depicted, a cross-section of the central lumen 286 can be oval in shape, although the cross-section can be other shapes (e.g., circular, square, rectangular, etc.). In some embodiments, one or more wires can be passed through the central lumen 286, which are associated with the electrodes 124 (FIG. 3A) disposed on the flexible tip portion 122, the magnetic position sensor 209 (FIG. 3J) disposed on the flexible tip portion 122, or other devices and/or sensors disposed on the flexible tip portion 122.

With further respect to FIG. 3J, in some embodiments, the high-density electrode catheter, as discussed herein, can include a magnetic position sensor disposed on a flexible tip portion of the catheter. As depicted in FIG. 3J, in some embodiments, a magnetic position sensor 209 can be disposed along a distal portion of the flexible tip portion of the high-density electrode catheter. In some embodiments, a position of the magnetic position sensor 209 can be determined and used to located one or more portions of the flexible tip portion, as discussed herein. In some embodiments, the flexible understructure 190 can include a magnetic position sensor mount 211, disposed on a distal portion 208 of the flexible understructure 190. In some embodiments, the magnetic position sensor mount 211 can house the magnetic position sensor 209. For example, the magnetic position sensor mount 211 can define a longitudinally extending slot 213, into which the magnetic position sensor 209 can be disposed, which is further depicted in relation to FIGS. 3S and 3T.

In some embodiments, the magnetic position sensor mount 211 can serve as an electrode understructure for the central electrode 130, depicted in FIG. 3A. In some embodiments, the magnetic position sensor 209 can be disposed within the slot 213, and a tubular electrically conductive layer (e.g., central electrode 130) can be disposed over an outer surface of the magnetic position sensor mount 211. As depicted in FIG. 3J, a channel 215 can be defined in a proximal outer surface of the magnetic position sensor mount 211. In some embodiments, a wire can be disposed within the channel 215 and coupled to the magnetic position sensor mount 211 (e.g. via solder). Although not depicted, the wire can electrically couple the magnetic position sensor mount 211 and thus the central electrode 130 to the computer system 20. This can allow for a dual-purpose magnetic position sensing and electrode assembly.

In some embodiments, the magnetic position sensor mount 211 can be coupled with the distal coupler 136. In some embodiments, the distal coupler 136 and the magnetic position sensor mount 211 can be formed from a single piece of material. The magnetic position sensor mount 211 can be connected to a distal end of the central frame 192-5 and can thus connect the central frame 192-5 to the distal coupler 136. In some embodiments, the magnetic position sensor mount 211 can include a keyed slot 217, which can be configured to receive a distal end of the central frame 192-5, as better depicted in FIG. 3S.

Figure 3S:
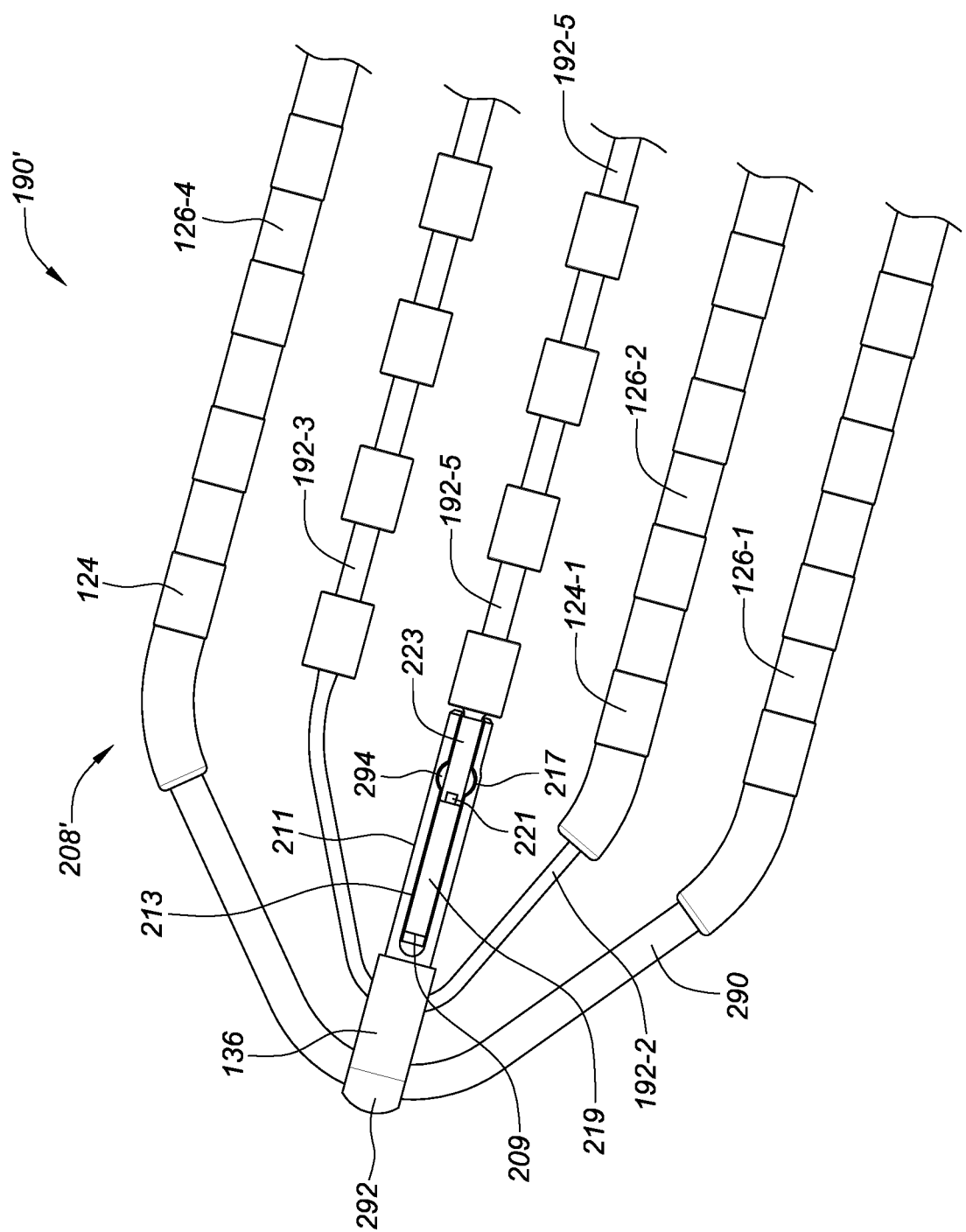
FIG. 3S is a bottom view of the distal portion of the flexible understructure, which is depicted in FIG. 3J, with the addition of electrodes, distal outboard understructure tubing, and an atraumatic tip, in accordance with embodiments of the present disclosure.

FIG. 3S is a bottom view of the distal portion 208' of the flexible understructure 190', which is depicted in FIG. 3J, with the addition of electrodes 124, distal outboard understructure tubing 290, and an atraumatic tip 292, in accordance with embodiments of the present disclosure. As depicted, the first outboard arm 126-1 and second outboard arm 126-4 can include a number of electrodes 124 disposed thereon. In some embodiments, the understructure that forms the first outboard arm 126-1 and second outboard arm 126-4 can be covered with a tube, which can be a bi-lumen tube, as depicted and discussed in relation to FIG. 3J. In some embodiments, as mentioned herein, the tube can be formed from a non-conductive material, such as a polymer. As depicted, the first inboard frame 192-2 is depicted as being covered with a tube to a location located distally with respect to the electrode 124.

In some embodiments, a bi-lumen tube can be used to cover portions of the flexible understructure along which electrodes are disposed. For example, in some embodiments, at least one wire can be associated with each electrode, which can be routed proximally along the flexible tip portion. Use of bi-lumen tubes for portions of the flexible understructure along which electrode are disposed, allows for the wires to be disposed in a first lumen of the bi-lumen tube and the frame (e.g., first inboard frame 192-2) to be routed in a second lumen of the bi-lumen tube. For portions of the flexible understructure that do not include electrodes, in some embodiments, a single lumen tube 290 can be used to cover the flexible understructure, as depicted with respect to the first and second outboard arms 126-1, 126-4.

In some embodiments, as discussed herein, the flexible understructure 190' can include a magnetic position sensor mount 211, disposed on a distal portion 208 of the flexible understructure 190'. In some embodiments, the magnetic position sensor mount 211 can house the magnetic position sensor 209. For example, the magnetic position sensor mount 211 can define the longitudinally extending slot 213, into which the magnetic position sensor 209 can be disposed.

In some embodiments, the magnetic position sensor mount 211 can serve as an electrode understructure for the central electrode 130, depicted in FIG. 3A. In some embodiments, the magnetic position sensor 209 can be disposed within the slot 213, and a tubular electrically conductive layer (e.g., central electrode 130) can be disposed over an outer surface of the magnetic position sensor mount 211.

In some embodiments, the magnetic position sensor mount 211 can be coupled with the distal coupler 136. In some embodiments, the distal coupler 136 and the magnetic position sensor mount 211 can be formed from a single piece of material. The magnetic position sensor mount 211 can be connected to a distal end of the central frame 192-5 and can thus connect the central frame 192-5 to the distal coupler 136. In some embodiments, the magnetic position sensor mount 211 can include a keyed slot 217, which can be configured to receive a distal end of the central frame 192-5, as better depicted in FIG. 3S. For example, as depicted, the keyed slot 217 can be a complementary shape with respect to a shape of the distal end of the central frame 192-5. As depicted, the keyed slot 217 can be a semicircular slot defined in the magnetic position sensor mount 211.

A distal end of the central frame 192-5 can include a complementary shape, which in this instance is a semicircular end 294. The semicircular end 294 can be disposed in the keyed slot 217, thereby preventing the central frame 192-5 from being pulled proximally from the magnetic position sensor mount 211. This can be beneficial when the flexible understructure 190' is in a stored state. For example, when the flexible understructure is disposed within an introducer/sheath in a collapsed state, a distance between the first and second outboard arms 126-1, 126-2 can decrease and the distance between the first and second inboard arms 126-2, 126-3 (FIG. 3A) can decrease; thereby causing the central frame 192-5 to be pulled distally due to an increase in longitudinal length of the flexible understructure 190'. The keyed relationship between the slot 217 and the distal end of the central frame 192-5 can prevent the central frame 192-5 from being pulled apart from the magnetic position sensor mount 211.

As further depicted in FIG. 3S, an atraumatic tip 292 can be disposed at a distal end of the distal coupler 136. In some embodiments, the atraumatic tip 292 can be formed from a flexible material (e.g., rubber). The atraumatic tip 292 can cushion the distal coupler 136 when contacting tissue. For example, the atraumatic tip 292 can cushion the distal coupler 136 when contacting cardiac tissue, when located in a cardiac region. In some embodiments, the atraumatic tip 292 can be mechanically fastened to the distal end of the distal coupler 136. In some embodiments, the atraumatic tip 292 can be attached to the distal end of the distal coupler 136 via an adhesive.

Figure 3T:
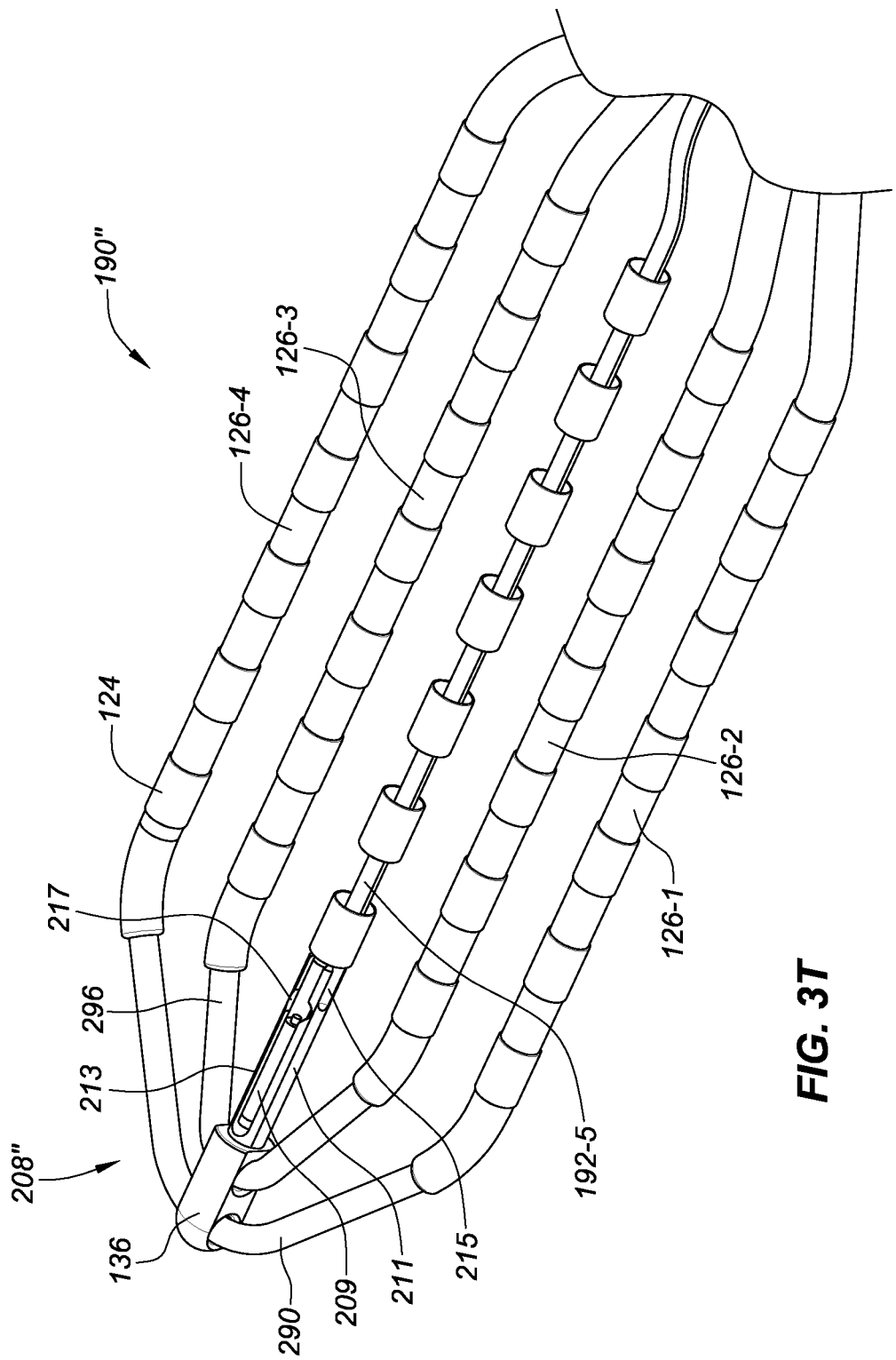
FIG. 3T is a bottom isometric view of the distal portion of the flexible understructure, which is depicted in FIG. 3J, with the addition of electrodes, distal inboard understructure tubing, and an atraumatic tip, in accordance with embodiments of the present disclosure.

FIG. 3T is a bottom isometric view of the distal portion 208" of the flexible understructure 190", which is depicted in FIG. 3J, with the addition of electrodes 124, distal inboard understructure tubing 296, and an atraumatic tip 292, in accordance with embodiments of the present disclosure. As previously discussed, a bi-lumen tube can be disposed over portions of the inboard frames that include electrodes 124 to form the first and second inboard arms 126-2, 126-3. Portions of the outboard and inboard arms 126-1, 126-2, 126-3, 126-4 located distally of the electrodes 124 can include a single lumen tube, such as depicted with respect to the distal outboard understructure tubing 290 and the distal inboard understructure tubing 296.

In some embodiments, the outboard and inboard arms 126-1, 126-2, 126-3, 126-4 can include single lumen tubes that cover the entirety of the arms. For example, the electrodes 124 can be disposed over the single lumen tubes and the inboard and outboard frames, as well as the wires that electrically couple the electrodes 124 can be disposed in a single lumen. In some embodiments, the outboard and inboard arms 126-1, 126-2, 126-3, 126-4 can include bi-lumen tubes that cover the entirety of the arms. As previously discussed herein, with respect to FIG. 3A, additional electrodes can be disposed on distal portions of the outboard and inboard arms 126-1, 126-2, . . . , 126-4 indicated by arrows 156-1, 156-2. Thus, in some embodiments, the additional electrodes can be disposed on bi-lumen tubes.

As further depicted in FIG. 3S, the magnetic position sensor 209 can include a number of coils 219 that in some embodiments can be wound around a core 221. In some embodiments, the magnetic position sensor 209 can be covered with an outer layer 223. For example, in some embodiments, an outer layer 223 (e.g., sleeve and/or coating) can be disposed over the magnetic position sensor 209. In some embodiments, the outer layer 223 can be a heat shrink material. As discussed, the magnetic position sensor 209 can be disposed in the longitudinally extending slot 213 and in some embodiments, the slot can be filled with an adhesive material to prevent the magnetic position sensor 209 and/or the end of the central frame 192-5 from coming loose.

Figure 3U:
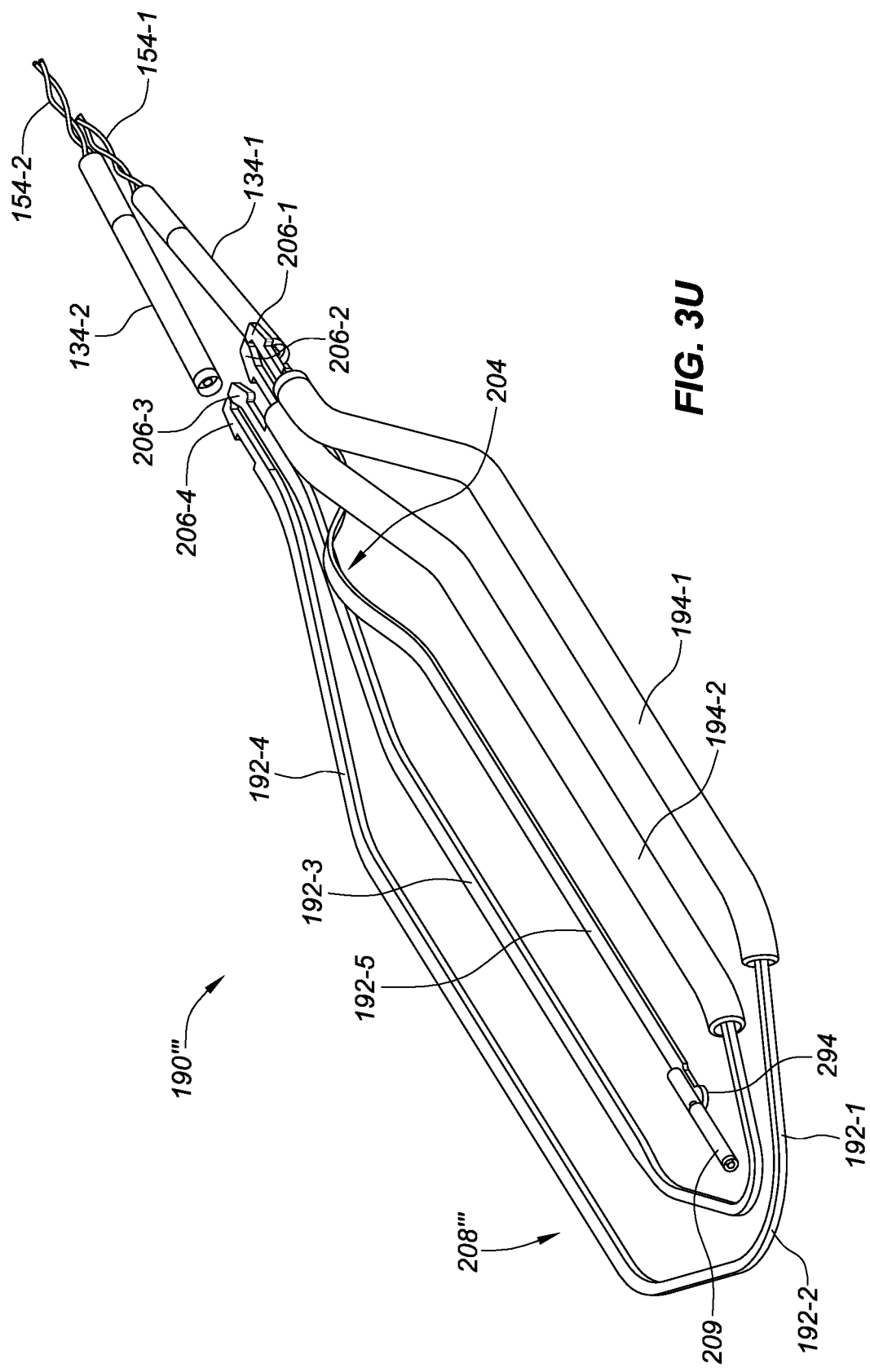
FIG. 3U is a bottom isometric view of the distal portion of the flexible understructure, which is depicted in FIG. 3J, without the distal coupler and magnetic position sensor mount, in accordance with embodiments of the present disclosure.

FIG. 3U is a bottom isometric view of the distal portion 208'" of the flexible understructure 190'", which is depicted in FIG. 3J, without the distal coupler 136 and magnetic position sensor mount 211, in accordance with embodiments of the present disclosure. The magnetic position sensor 209 is depicted in a position where it would be disposed, if it were positioned in the magnetic position sensor mount 211. As depicted, the magnetic position sensor 209 can be located along the distal portion 208'" of the flexible understructure 190'".

As discussed herein, the magnetic position sensor 209 can sense a position and/or orientation, which can be provided to the computer system 20. The computer system 20 can use the position and/or orientation sensed by the magnetic position sensor 209 to determine the position and/or orientation of the flexible tip portion 122 (FIG. 3A). As depicted, the magnetic position sensor 209 can be axially aligned with a longitudinal axis of the central frame 192-5. However, in some embodiments, the magnetic position sensor 209 can be canted with respect to the central frame 192-5. For example, the magnetic position sensor 209 can be canted laterally with respect to the central frame 192-5 and/or a longitudinal axis of the flexible tip portion 122 or a catheter shaft attached to the flexible tip portion 122. In some embodiments, the magnetic position sensor 209 can be canted up or down, with respect to the central frame 192-5 and/or a longitudinal axis of the flexible tip portion 122 or a catheter shaft attached to the flexible tip portion 122.

Although the magnetic position sensor 209 is depicted as being located along the distal portion 208'", and specifically, distal to the central frame 192-5, the magnetic position sensor 209 can be disposed at other locations along the flexible understructure. In some embodiments, the magnetic position sensor 209 can be disposed proximally or distally with respect to its depicted location in FIG. 3U. In some embodiments, the magnetic position sensor 209 can be disposed laterally with respect to its depicted location in FIG. 3U. For example, in some embodiments, the magnetic position sensor 209 can be disposed in a different location along the distal portion 208'", while still being able to sense a position and/or orientation of the distal portion 208'".

Figure 4:
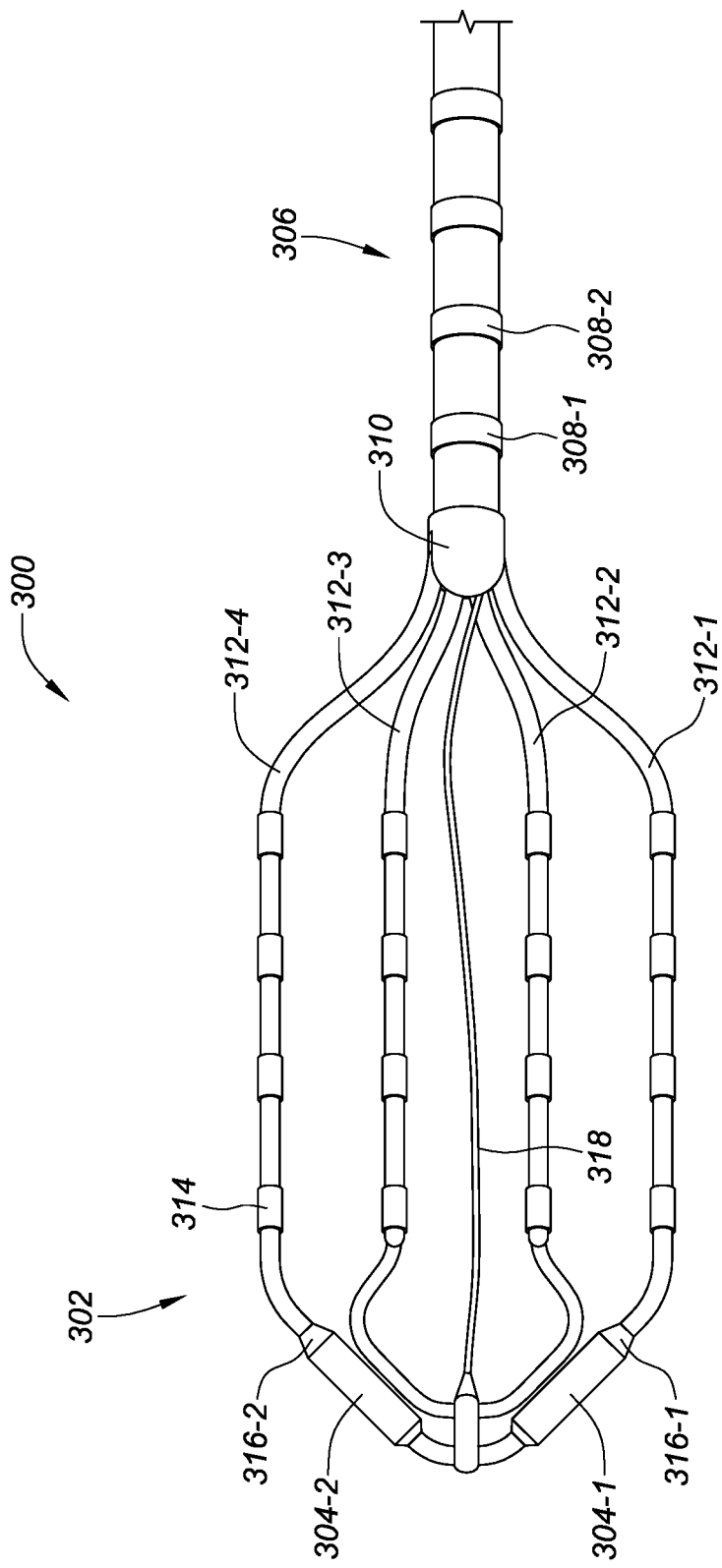
FIG. 4 is a top view of a high-density electrode catheter with a flexible tip portion having a pair of magnetic position sensors disposed on a distal portion of the flexible tip portion, in accordance with embodiments of the present disclosure.

In some embodiments, the magnetic position sensor 209 can be located along at least one of the first and second outboard frames 192-1, 192-4 and/or along at least one of the first and second inboard frames 192-2, 192-3. In some embodiments, magnetic position sensors can be disposed on one or more of the inboard and/or outboard frames to determine a position and/or orientation of one of the frames and/or a portion of one of the frames to other frames and/or portions of one of the frames. FIG. 4 illustrates an embodiment providing for placement of magnetic position sensors in a different location on a distal portion of a flexible tip portion of a catheter.

FIG. 4 is a top view of a catheter 300 with a flexible tip portion 302 having a pair of magnetic positions sensors 304-1, 304-2 disposed on a distal portion of the flexible tip portion 302, in accordance with embodiments of the present disclosure. The catheter 300 can include a longitudinally extending catheter shaft 306, on which one or more ring electrodes 308-1, 308-2 are disposed. In some embodiments, the ring electrodes 308-1, 308-2 can be used for position sensing, diagnostic, and/or therapeutic purposes. Although the one or more ring electrodes 308-1, 308-2 are discussed in relation to FIG. 4, same or similar electrodes can be included in other embodiments discussed herein, for example, in relation to those embodiments discussed in FIGS. 5, 6, and 7. In some embodiments, the flexible tip portion 302 can be coupled to the catheter shaft 306 via a proximal coupler 310, from which a first outboard arm 312-1, second outboard arm, 312-4, first inboard arm 312-1 and second inboard arm 312-3 extend.

As depicted, a plurality of electrodes 314 can be disposed on the arms 312-1, 312-2, 312-3, 312-4. Although sixteen electrodes 314 are depicted in total on the arms 312-1, 312-2, 312-3, 312-4, the number of electrodes disposed on the arms can be greater than or less than sixteen electrodes. In some embodiments, the plurality of electrodes 314 can be used for position sensing, diagnostic, and/or therapeutic purposes. In some embodiments, one or more magnetic position sensors can be disposed on one of the inboard and/or outboard arms 312-1, 312-2, 312-3, 312-4. For example, as depicted, a pair of magnetic position sensors 304-1, 304-2 can be disposed on a distal portion of the first and second outboard arms 312-1, 312-4. Although the pair of magnetic position sensors 304-1, 304-2 are depicted as being disposed on the distal portion of the first and second outboard arms 304-1, 304-2, the magnetic position sensors 304-1, 304-2 can be disposed on other portions of the flexible tip portion 302 (e.g., the first and second inboard arms 312-2, 312-3).

In some embodiments, the magnetic position sensors 304-1, 304-2 can be formed via a number of windings made with a wire formed from a conductive material (e.g., copper) about the first and second outboard arms 312-1, 312-2. In some embodiments, the number of windings can be made over respective sensor cores 316-1, 316-2 that can be formed from a magnetically permeable material. For example, in some embodiments, a sensor core 316-1, 316-2 can be disposed over a portion of one of the arms 312-1, 312-2, 312-2, 312-4 and numerous windings of the conductive wire can be made over the sensor core 316-1, 316-2.

In some embodiments, one or more magnetic position sensors can be formed on an understructure associated with one of the arms 312-1, 312-2, 312-3, 312-4. For example, although the magnetic position sensors 304-1, 304-2 are depicted as being disposed about the arms 312-1, 312-4, the magnetic position sensors can be disposed on the understructure of one or more of the arms 312-1, 312-2, 312-3, 312-4. For example, the understructure that forms the arms 312-1, 312-2, 312-3, 312-4 can include one or more slots in which the magnetic position sensors can be disposed. Alternatively, and/or in addition, the magnetic position sensors can be wound about an understructure that forms the one or more arms 312-1, 312-2, 312-3, 312-4.

In some embodiments, one or more electrodes can be disposed over one or more of the magnetic position sensors 304-1, 304-2, as discussed in relation to FIG. 3A. For example, in some embodiments, one or more electrodes can define a lumen through which one or more of the magnetic position sensors 304-1, 304-2 extend. In some embodiments, an electrode may not be disposed over an entirety of the magnetic position sensors 304-1, 304-2. For example, as previously discussed herein, one or more electrodes may be disposed over only a portion of the magnetic position sensors 304-1, 304-2, such as a top half and/or bottom half. In some embodiments, one or more spot electrodes can be disposed on the one or more magnetic position sensors. In some embodiments, a flexible circuit can be disposed over the one or more magnetic position sensors 304-1, 304-2, which includes one or more electrodes disposed thereon.

As depicted, the magnetic position sensors 304-1, 304-2 can be formed on portions of the outboard arms 312-1, 312-4, which are divergent with a longitudinal axis defined by the catheter 300. In some embodiments, the magnetic position sensors 304-1, 304-2 can be electrically coupled with the computing system 20 via one or more wires 318 (e.g., one or more twisted pairs of wires). As depicted, in some embodiments, the wires 318 may not be enclosed via a lumen (e.g., bi-lumen) associated with one of the arms 312-1, 312-2, 312-3, 312-4. The wires 318 can extend from each one of the magnetic position sensors 304-1, 304-2, proximally between the first and second inboard arms 312-2, 312-3 and along the catheter shaft 306. In some embodiments, as previously discussed herein, the flexible tip portion 302 can include a central arm, along which the wires 318 can extend.

In some embodiments, the wires 318 can extend along one of the first and second outboard arms 312-1, 312-4 and/or the first and second inboard arms 312-2, 312-4. In some embodiments where the wires travel down one or more of the arms 312-1, 312-2, 312-3, 312-4, it can be beneficial to maintain symmetry between the arms 312 along which the wires extend. For example, it can be beneficial to have one set of wires extend down the first outboard arm 312-1 and the other set of wires to extend down the second outboard arm 312-2; and/or to have one set of wires extend down the first inboard arm 312-2 and the other set of wires to extend down the second inboard arm 312-3. By maintaining the symmetry between the arms 312 along which the wires extend, a symmetry in deflection of the arms 312 can be maintained. For example, if wires associated with the magnetic position sensors 304-1, 304-2 were run along a first outboard arm 312-1 and a first inboard arm 312-2, the flexible tip portion 302 may become unbalanced in deflection, due to an increased mechanical stiffness of the side of the flexible tip portion 302 that includes the wires (e.g., the first outboard arm 312-1 and second outboard arm 312-2).

Figure 5A:
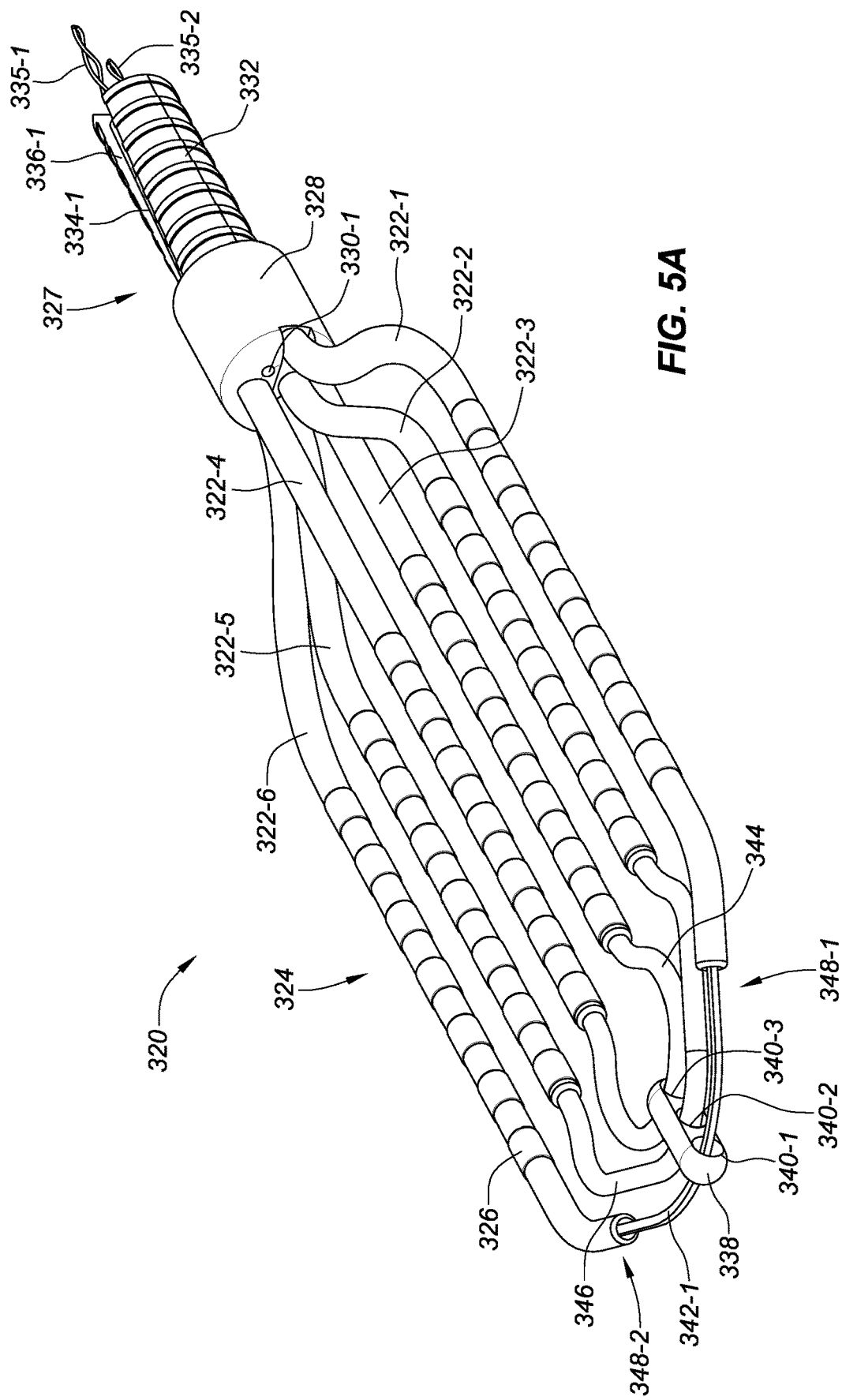
FIG. 5A is an isometric view of a high-density electrode catheter that includes six longitudinally extending arms, in accordance with embodiments of the present disclosure.

FIG. 5A is an isometric view of a high-density electrode catheter 320 that includes six longitudinally extending arms 322-1, 322-2, . . . , 322-6, in accordance with embodiments of the present disclosure. In some embodiments, the high-density electrode catheter 320 can include a flexible tip portion 324 formed from first and second outboard arms 322-1, 322-6, first and second inboard arms 322-3, 322-4, and first and second middle arms 322-2, 322-5. As depicted, each one of the arms 322-1, 322-2, . . . , 322-6 can carry a plurality of electrodes 326. In some embodiments, each one of the arms 322-1, 322-2, . . . , 322-6 can carry seven electrodes 326, allowing for an array of 42 electrodes 326 disposed on the flexible tip portion 324. In some embodiments, a greater or lesser number of electrodes 326 can be disposed on the flexible tip portion 324.

In some embodiments, the flexible tip portion 324 can be coupled to a catheter shaft (not depicted) via a proximal coupler 327. In some embodiments, the proximal ends of the arms 322-1, 322-2, . . . , 322-6 can be disposed in a proximal coupler 328. The proximal coupler 328 can be of the same design as the distal coupler head 144 depicted and discussed in relation to FIG. 3D. For example, one of the inboard arms 322-3, 322-4 can be disposed in the lumen 160 depicted in FIG. 3D. In some embodiments, the proximal coupler 328 can include the same or similar features with respect to the distal coupler head 144, depicted and discussed in relation to FIGS. 3A to 3D. In some embodiments, the lumen 160, depicted in FIG. 3D can provide a location for an understructure associated with one of the inboard arms 322-3, 322-4 to be disposed. As previously discussed, each one of the arms 322-1, 322-2, . . . , 322-6 can include an understructure, over which a tube can be disposed. In some embodiment the tube disposed over the under structure can be a bi-lumen and/or a single lumen tube.

In some embodiments, the proximal coupler 328 can include irrigation ports (e.g., irrigation port 330-1). In some embodiments, the proximal coupler 328 can include four irrigation ports, although only irrigation port 330-1 is visible in FIG. 5A. As depicted, the proximal coupler 328 can be connected to a distal end of a connective stem portion 332, as discussed herein. In some embodiments, the connective stem portion 332 can include a first magnetic position sensor 334-1 and a second magnetic position sensor (hidden from view), each of which can be coupled via a sensor cable 335-1, 335-2. In some embodiments, the connective stem portion 332 can define a first sensor groove 336-1 and a second sensor groove (hidden from view).

As depicted, in some embodiments, the first and second outboard arms 322-1, 322-6 and the first and second middle arms 322-2, 322-5 can extend from the distal end of the proximal coupler 328 along a common plane and can be coupled at their distal ends via a distal coupler 338. In some embodiments, the first inboard arm 322-3 can extend distally from the distal end of the proximal coupler 328, below the common plane, toward the distal coupler 338 and the second inboard arm 322-4 can extend distally from the distal end of the proximal coupler 328, above the common plane, toward the distal coupler 338, where it joins the first inboard arm 322-3. At the distal coupler, the first and second inboard arms 322-3, 322-4 can be coupled with the first and second outboard arms 322-1, 322-6 and the first and second middle arms 322-2, 322-5. Because the first and second inboard arms 322-3, 322-4 extend from the proximal coupler 328 on either side of the common plane, a diameter of the proximal coupler 328 can be made more compact. For example, six frames do not extend distally from the proximal coupler 328 on a common plane, which could necessitate a wider proximal coupler.

As depicted, each set of arms 322-1, 322-2, . . . , 322-6 can extend through a mounting lumen 340-1, 340-2, 340-3 defined in the distal coupler 338. Although the arms 322-1, 322-2, . . . , 322-6 are depicted as being coupled at their distal ends, in some embodiments, the arms 322-1, 322-2, . . . , 322-6 may be uncoupled and may not include a distal coupler 338. As further depicted and discussed herein, the arms 322-1, 322-2, . . . , 322-6 can include bi-lumen tubes (e.g., FIG. 3K) that are disposed over portions of an understructure (e.g., outboard frame 342-1) that include electrodes 326. In some embodiments, a single lumen tube 344, 346 can cover portions of the understructure forming each one of the arms 322-1, 322-2, . . . , 322-6 that do not have electrodes disposed thereon.

In some embodiments, although not depicted, additional electrodes can be disposed along distal portions of the arms 322-1, 322-2, . . . , 322-6, as indicated by arrows 348-1, 348-2. For example, although FIG. 5A depicts the electrodes 326 linearly aligned with one another along the linear portions of the arms 322-1, 322-2, . . . , 322-6, embodiments of the present disclosure can benefit from additional electrodes disposed along the regions of the arms 322-1, 322-2, . . . , 322-6 indicated by arrows 348-1, 348-2.

Figure 5B:
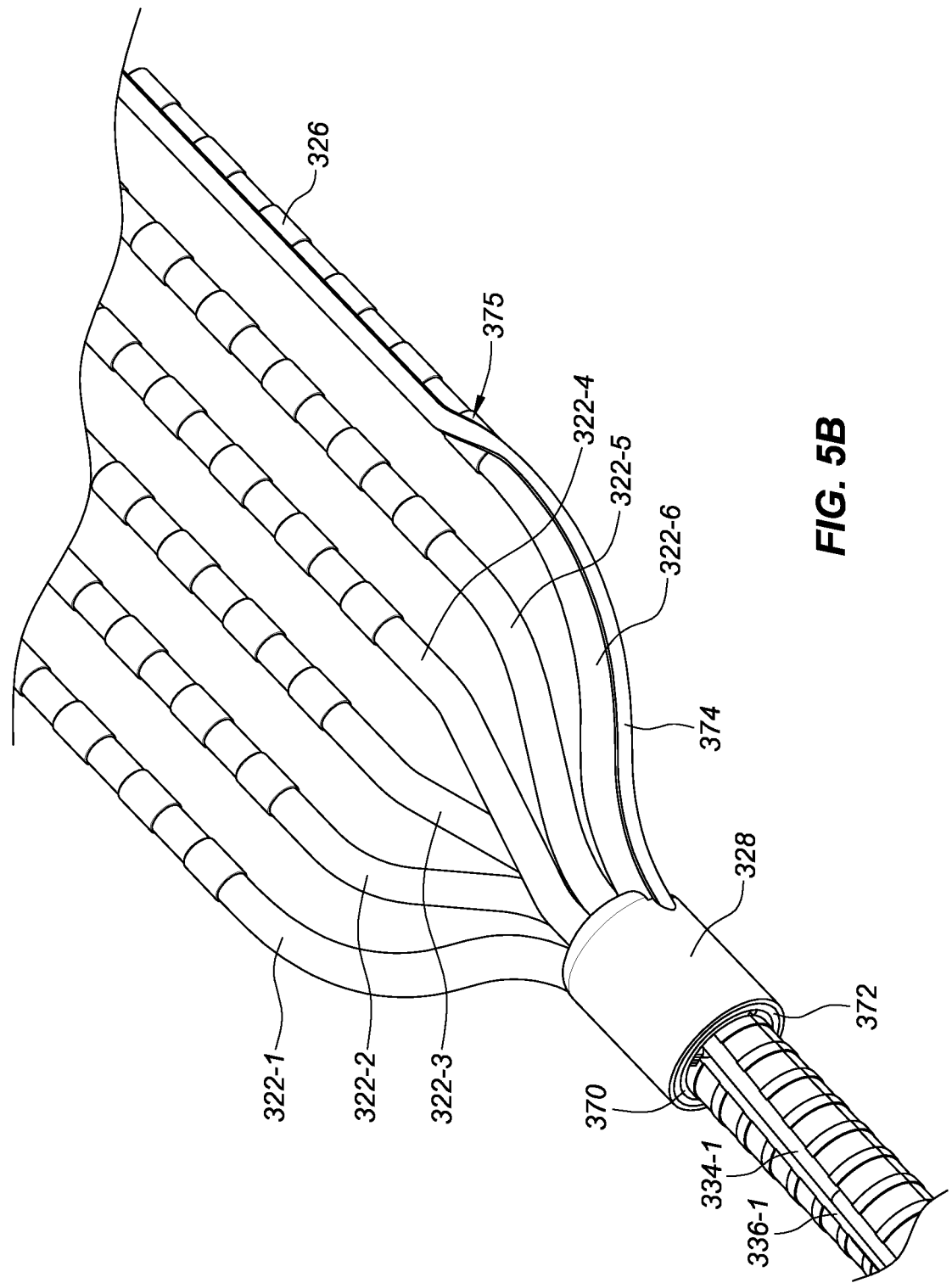
FIG. 5B is an isometric distally facing view of the high-density electrode catheter depicted in FIG. 5A, which includes six longitudinally extending arms, in accordance with embodiments of the present disclosure.

FIG. 5B is an isometric distally facing view of the high-density electrode catheter 320 depicted in FIG. 5A, which includes six longitudinally extending arms 322-1, 322-2, . . . , 322-6, in accordance with embodiments of the present disclosure. As depicted, the proximal coupler 327 can include a mounting portion 370, as further depicted and discussed in relation to FIG. 3M. In some embodiments, the proximal coupler 327 can include a manifold portion 372 that includes the same or similar features as those discussed in relation to the manifold portion 162 depicted in FIG. 3F.

Figure 5C:
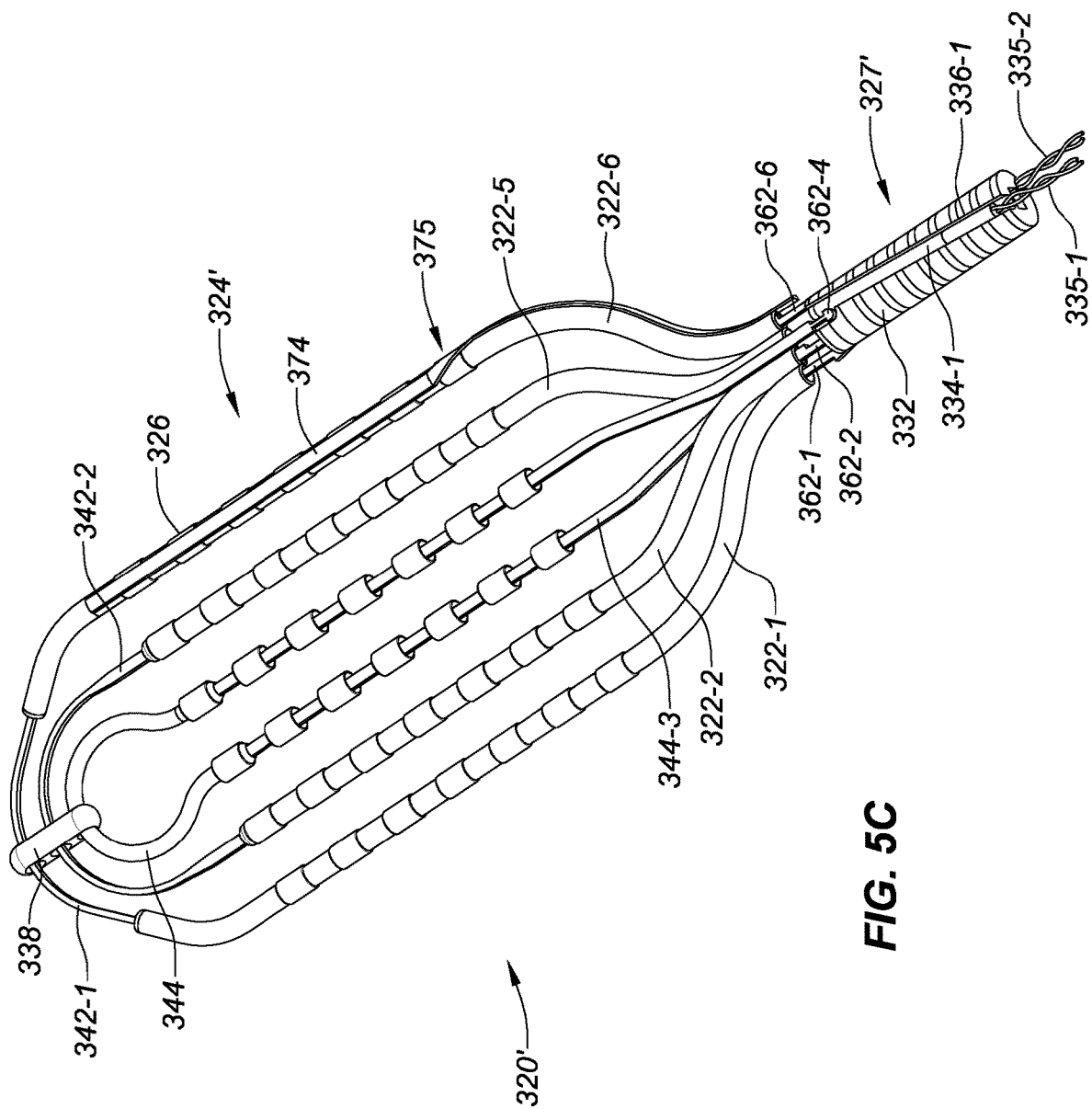
FIG. 5C is the high-density electrode catheter of FIG. 5A, with further illustration of a distal end of the proximal coupler, as well as frame mounting portions, in accordance with embodiments of the present disclosure.

As further depicted in FIGS. 5B and 5C, in some embodiments, a flexible circuit 374 can be disposed on one or more portions of the arms 322-1, 322-2, . . . , 322-6 and/or an understructure of one of the arms 322-1, 322-2, . . . , 322-6. In some embodiments, a number of electrodes can be disposed on flexible circuits 374 disposed on one or more of the arms 322-1, 322-2, . . . , 322-6. As depicted in FIG. 5C, ring electrodes are disposed about each one of the arms 322-1, 322-2, . . . , 322-6. Alternatively, and/or in addition, in some embodiments, a flexible circuit can be disposed along one or more of the arms 322-1, 322-2, . . . , 322-6 and electrodes can be formed on the flexible circuit. In some embodiments, this can reduce and/or eliminate a number of wires extending through each one of the arms 322-1, 322-2, . . . , 322-6, allowing for smaller diameter arms 322-1, 322-2, . . . , 322-6 to be used.

In some embodiments, the flexible circuit 374 can extend from a proximal end of one or more of the arms 322-1, 322-2, . . . , 322-6. For example, in FIGS. 5B and 5C, the flexible circuit 374 is depicted as extending from a proximal end of the second outboard arm 322-6 towards a distal end of the second outboard arm 322-6. For reference, the flexible circuit 374 is depicted as being disposed over electrodes 326, however, in use the flexible circuit 374 can replace the electrodes 326 and electrodes can be disposed on the flexible circuit 374.

Although not depicted, in some embodiments, one or more electrical traces can be formed in the flexible circuit 374 and can electrically couple one or more electrodes disposed on the flexible circuit 374 with the computer system 20 and/or computer system 64. In some embodiments, a location of the electrodes disposed on the flexible circuit 374 can match the location of the electrodes 326.

In some embodiments, the flexible circuit 374 can extend along an outer surface of the second outboard arm 322-6 and can transition to extending along a top surface of the second outboard arm 322-6 and a bottom surface of the second outboard arm 322-6, at a transition point 375. In some embodiments, by transitioning the flexible circuit 374 from the outer surface of the second outboard arm 322-6 to the top surface of the second outboard arm 322-6 and the bottom surface of the second outboard arm 322-6, a linear flexible circuit can be used. For example, in some embodiments, a flexible circuit can be disposed entirely along a top and/or bottom surface of the second outboard arm 322-6. However, due to the curve in the proximal portion of the second outboard arm 322-6, the flexible circuit disposed on the top/bottom surface of the second outboard arm 322-6 may need to be constructed with a curve that matches the proximal curved portion of the second outboard arm 322-6.

Thus, embodiments of the present disclosure can provide for a linearly shaped (e.g., axially extending) flexible circuit 374 that can be disposed on the curved portion of the second outboard arm 322-6, along the top and bottom of the second outboard arm 322-6.

Figure 5D:
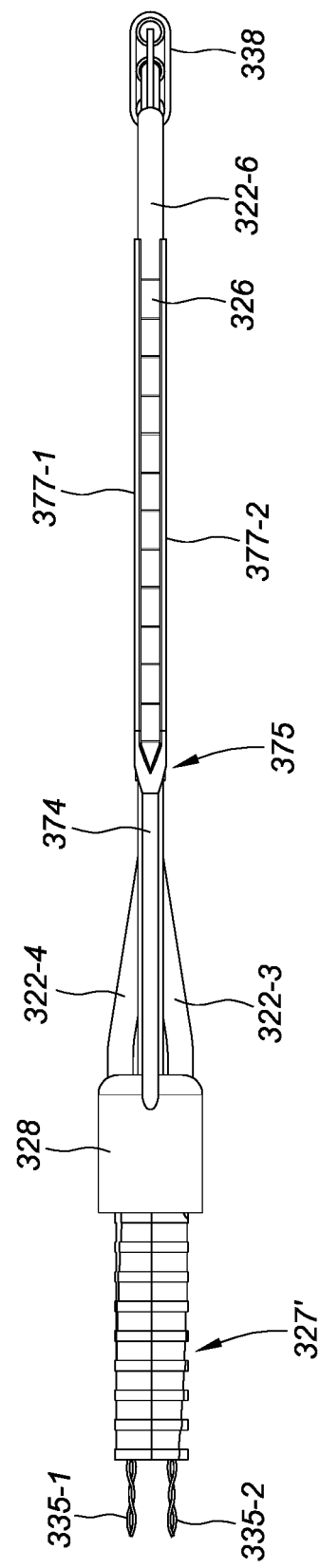
FIG. 5D is a side view of the high-density electrode catheter of FIG. 5A, in accordance with embodiments of the present disclosure.

As depicted in FIG. 5D, the flexible circuit 374 can branch at transition point 375, into a top flexible circuit 377-1 and a bottom flexible circuit 377-2. In some embodiments, the top flexible circuit 377-1 and the bottom flexible circuit 377-2 can branch from a single flexible circuit 374. However, in some embodiments, the top flexible circuit 377-1 and the bottom flexible circuit 377-2 can be formed from discrete flexible circuits. For instance, two separate flexible circuits can extend distally along the second outboard arm 322-6, from a proximal end of the second outboard arm 322-6, towards a distal end of the second outboard arm 322-6. Thus, the top flexible circuit 377-1 can be formed from a separate flexible circuit than the bottom flexible circuit 377-2. In some embodiments, portions of the flexible circuit proximal of the transition point 375 can overlap one another. Although the foregoing discussion is made with respect to the second outboard arm 322-6, the other arms 322-1, 322-2, . . . , 322-5 of the electrode catheter 320' can include flexible circuits and respective transition points, as discussed in relation to the second outboard arm 322-6.

In some embodiments, the flexible circuit 374 can extend along an outer surface of the second outboard arm 322-6 and can transition to extending along either the top surface of the second outboard arm 322-6 or the bottom surface of the second outboard arm 322-6, at a transition point 375. For example, in some embodiments, the flexible circuit 374 can extend along one of the top or bottom of the second outboard arm 322-6. Although the foregoing discussion is made with respect to the second outboard arm 322-6, the other arms 322-1, 322-2, . . . , 322-5 of the electrode catheter 320' can include flexible circuits and respective transition points, as discussed in relation to the second outboard arm 322-6.

Although discussed in relation to FIGS. 5B, 5C, and 5D, flexible circuits can be disposed on other embodiments discussed herein. For example, embodiments of the present disclosure discussed in relation to at least FIGS. 3A to 4, and 6A to 11 can include one or more flexible circuits disposed on a flexible tip portion.

FIG. 5C depicts the high-density electrode catheter 320' of FIG. 5A, with further illustration of a distal end of the proximal coupler 327, as well as frame mounting portions 362-1, 362-2, . . . , 362-6, in accordance with embodiments of the present disclosure. In some embodiments, each arm 322-1, 322-2, . . . , 322-6 can include an understructure frame 342-1, 342-2, 342-3, as discussed herein. For example, with reference to FIG. 5C, various portions of the frames 342-1, 342-2, 342-3 are depicted. As further depicted, proximal portions of the frames 342-1, 342-2, 342-3 can include frame mounting portions 362-1, 362-2, . . . , 362-5 (362-3, 363-6 are hidden from view), as discussed in relation to FIGS. 3N to 3P. The frame mounting portions 362-1, 362-2, . . . , 362-6 can be disposed in a mounting portion 176 as further depicted in relation to FIG. 3M. In some embodiments, the same mounting portion 176 can be used for the catheter 120 depicted in FIG. 3A, which includes five longitudinally extending arms, as can be used with the catheter 320 depicted in FIG. 5A, which includes six longitudinally extending arms.

In some embodiments, the frame mounting portion 362-4 associated with the second inboard arm 322-4 can include the same features as the frame mounting portion 206-5, depicted in FIG. 3O and can be inserted into a mounting lumen (e.g., mounting lumen 269 depicted in FIG. 3M). In some embodiments, the frame mounting portion (hidden from view) associated with the first inboard arm 322-4 can include the same features as the frame mounting portion 206-5, depicted in FIG. 3O and can be inserted into a mounting lumen (e.g., mounting lumen 275 depicted in FIG. 3M).

Although one or more magnetic position sensors are not depicted on the device depicted in FIGS. 5A to 5D, in some embodiments one or more magnetic position sensors can be disposed thereon. For example, in some embodiments, a device with six longitudinally extending arms can include one or more magnetic position sensors disposed thereon. In some embodiments, the magnetic position sensors can be disposed on portions of the first and second outboard arms 322-1, 322-6. For example, in some embodiments, magnetic position sensors can be disposed on a distal portion of the first and second outboard arms 322-1, 322-6 in a similar configuration as that depicted and discussed in relation to FIG. 4. In some embodiments, one or more magnetic position sensors can be disposed on one or more of the distal portions of the first and second middle arms 322-2, 322-5, in a similar configuration as that depicted and discussed in relation to FIG. 4. In some embodiments, one or more magnetic position sensors can be disposed on one or more of the distal portions of the first and second inboard arms 322-3, 322-4, in a similar configuration as that depicted and discussed in relation to FIG. 4.

Figure 6A:
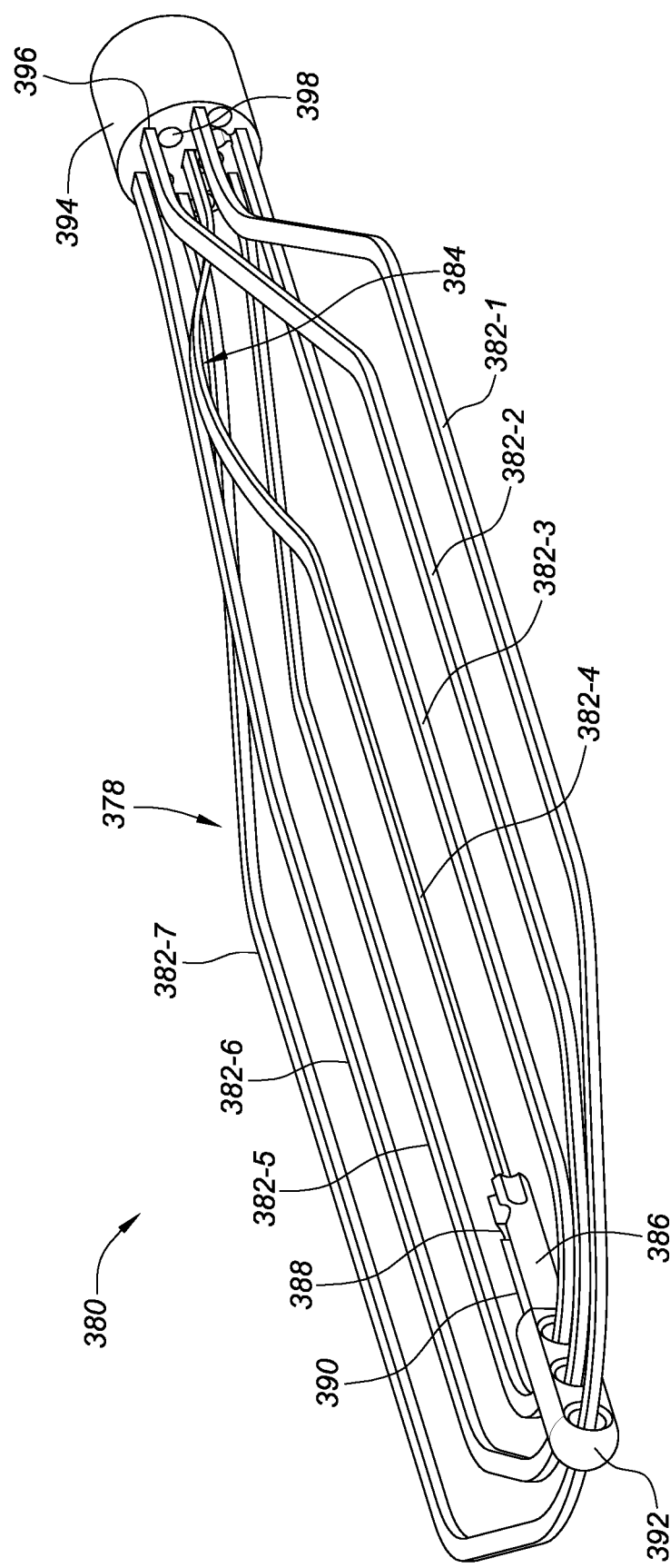
FIG. 6A is an isometric view of an understructure of a flexible tip of a high-density electrode catheter, in accordance with embodiments of the present disclosure.

FIG. 6A is an isometric view of an understructure 378 of a flexible tip 380 of a high-density electrode catheter, in accordance with embodiments of the present disclosure. As depicted, the flexible tip 380 can include a first outboard frame 382-1, a second outboard frame 382-7, a first middle frame 382-2, a second middle frame 382-6, a first inboard frame 382-3, a second inboard frame 382-5, and a central frame 382-4. The flexible tip 380 can include similar or the same features as discussed in relation to high-density electrode catheter 120 of FIG. 3A, with the exception of an additional first and second middle frame 382-2, 382-6. As further depicted and discussed in relation to FIG. 6B, a proximal mounting portion 394 can be used, in which all of the seven frames 382-1, 382-2, . . . , 382-7 can be disposed.

As further depicted, the central frame 382-4 can include a non-linear lengthening feature 384, as previously discussed herein. The non-linear lengthening feature 384 can allow for the central frame 382-4 to lengthen in response to the flexible tip 380 being in a stored (e.g., collapsed) configuration, as discussed herein. In some embodiments, the distal end of the central arm 382-4 can be connected with a magnetic position sensor mount 386 via a keyed slot 388 and a correspondingly keyed distal end (hidden from view) of the central frame 382-4.

In some embodiments, a magnetic position sensor (not depicted) can be disposed in a longitudinally extending slot 390 defined in the magnetic position sensor mount 386, allowing for a position and orientation of a distal end of the flexible tip 380 to be determined. In some embodiments, as previously discussed herein, an electrically conductive jacket can be disposed over the magnetic position sensor mount 386, which can act as an electrode. As further depicted, in some embodiments, the magnetic position sensor mount 386 can be coupled to a distal coupler 392, which can couple the distal ends of each one of the frames 382-1, 382-2, . . . , 382-7. As discussed herein, in some embodiments, a coupler may not be used and the frames 382-1, 382-2, . . . , 382-7 can be freely disposed with respect to one another.

In some embodiments, the proximal mounting portion 394 can define insertion lumens (e.g., insertion lumen 396) for a proximal mounting portion (not depicted) of each one of the frames 382-1, 382-2, ..., 382-7. In some embodiments, a wire lumen (e.g., wire lumen 398) can be defined next to each insertion lumen 396, allowing for wires associated with one or more electrical sensors (e.g., electrodes) or other devices disposed on the understructure 378 to be passed through the wire lumen.

Figure 6B:
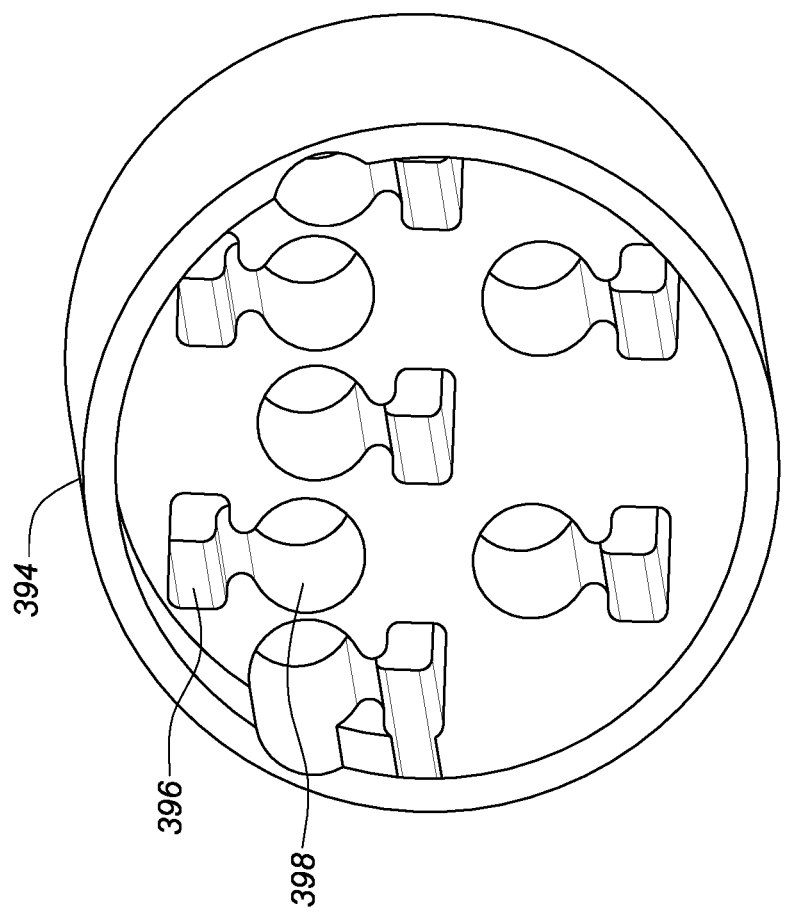
FIG. 6B is a proximal end view of the mounting portion depicted in FIG. 6A, in accordance with embodiments of the present disclosure.

FIG. 6B is a proximal end view of the proximal mounting portion 394 depicted in FIG. 6A, in accordance with embodiments of the present disclosure. In some embodiments, the proximal mounting portion 394 can be disposed on a distal end of a catheter shaft (not depicted). In some embodiments, a number of insertion lumens 396 are defined in a distal face of the proximal mounting portion 394. For simplicity, discussion of the insertion lumens is limited to insertion lumen 396. As discussed with respect to FIGS. 3N and 3P for the five armed flexible tip portion, a proximal mounting portion of each one of the frames can be inserted into a respective one of the insertion lumens 396. For instance, the proximal mounting portion of the first middle frame 382-3 can include spring clip features similar or the same as those discussed with respect to the central mounting portion 206-5 discussed in relation to FIGS. 3N to 3P. The proximal mounting portion 394 of the first middle frame 382-3 can thus be proximally pushed through the insertion lumen 396, allowing for the proximal mounting portion of the first middle frame 382-3 to be locked into place with respect to the proximal mounting portion 394. As depicted with respect to FIG. 6B, the proximal mounting portion 394 can include seven insertion lumens and seven wire lumens 398 to accommodate each one of the frames 382-1, 382-2, ..., 382-7 and associated wiring.

Figure 7:
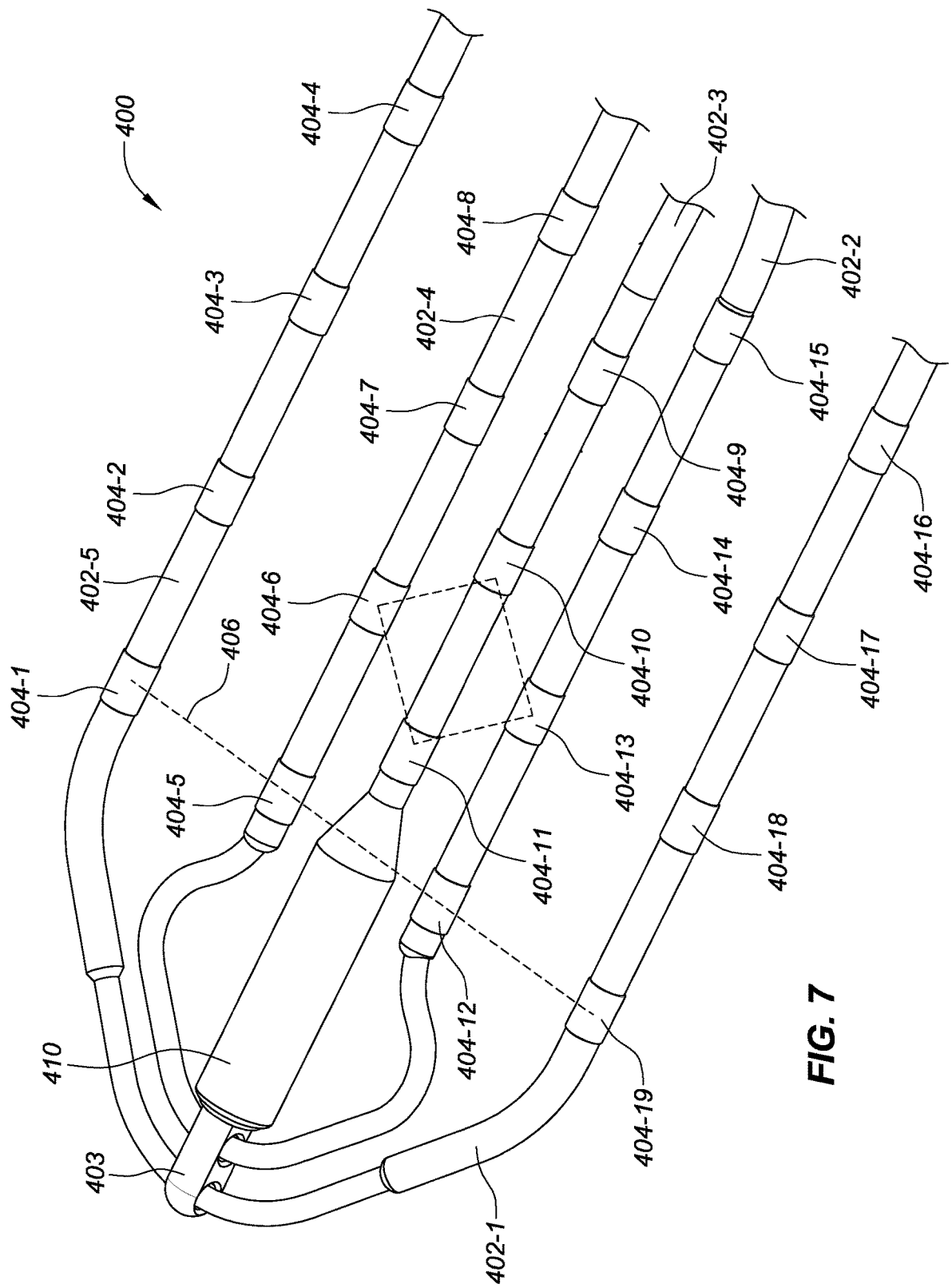
FIG. 7 is a distal flexible tip portion of a high-density electrode catheter with a particular electrode configuration, in accordance with embodiments of the present disclosure.

FIG. 7 depicts a distal flexible tip portion 400 of a high-density electrode catheter with a particular electrode configuration, in accordance with embodiments of the present disclosure. As depicted, the distal flexible tip portion 400 includes a first outboard arm 402-1, a first inboard arm 402-2, a central arm 402-3, a second inboard arm 402-4, and a second outboard arm 402-5, all coupled by a distal coupler 403. As depicted, a number of electrodes 404-1, 404-2, ..., 404-19 can be disposed on each one of the arms 402-1, 402-2, ..., 402-5. As depicted, a spacing between each lateral row of electrodes 404-1, 404-5, 404-12, 404-19, denoted by dotted line 406 can have an equal spacing between each electrode 404-1, 404-5, 404-12, 404-19.

In some embodiments, the spacing between the electrodes 404 in each lateral row of electrodes can be in a range from 3 to 5 millimeters. In some embodiments, the spacing between the electrodes 404 in each lateral row of electrodes 404 can be 4 millimeters. As depicted, the electrodes 404-9, 404-10, 404-11 disposed on the central arm 404-3 can be longitudinally staggered with respect to the electrodes disposed on the first and second outboard arms 404-1, 404-5 and first and second inboard arms 404-2, 404-4. In some embodiments, the electrodes 404-9, 404-10, 404-11 disposed on the central arm 404-3 can be longitudinally staggered with respect to the electrodes disposed on the first and second outboard arms 404-1, 404-5 and first and second inboard arms 404-2, 404-4 by a length in a range from 1 to 3 millimeters. In some embodiments, the staggered length can be 2 millimeters.

In some embodiments, the electrodes disposed on the central arm 404-3 and the electrodes disposed on the first and second inboard arms 404-2, 404-4 can form a pattern with a decreased spacing, represented by the dotted box 408.

In some embodiments, a spacing length between each electrode 404-6, 404-10, 404-11, 404-13 intersected by the dotted box 408 can include a length in a range from 1.5 to 3.5 millimeters. In some embodiments, the spacing length can be 2.8 millimeters. Although particular ranges are provided herein, the ranges can be approximate and spacing between the electrodes can be less than or greater than the provided ranges.

As further depicted in FIG. 7, an additional electrode 410 can be disposed at a distal end of the central arm 404-3. As previously discussed herein, the additional electrode 410 can be used for diagnostics, mapping, and/or therapeutic purposes. In some embodiments, as further discussed herein, a magnetic position sensor can be disposed within the additional electrode 410 to provide for mapping capabilities of the distal flexible tip portion 400.

FIGS. 8A to 8E depict various electrode spacing configurations for electrodes disposed on a distal flexible tip portion of a high-density electrode catheter, in accordance with embodiments of the present disclosure. In relation to FIGS. 8A to 8E, an overall dimension represented by line "a" and line "b" (e.g., a×b) can be the same. However, a density and configuration of the electrode spacing can change. Although particular ranges are provided herein, with respect to FIGS. 8A to 8E, the ranges can be approximate and spacing between the electrodes can be less than or greater than the provided ranges. In some embodiments, although particular numbers of electrodes are depicted in relation to FIGS. 8A to 8E, the embodiments depicted herein can include greater than or fewer electrodes than depicted.

As depicted in FIG. 8A, a plurality of electrodes 424-1, 424-2, 424-3 are disposed on a flexible framework 420 formed from a plurality of arms 422-1, 422-2, 422-3, 422-4, including a first outboard arm 422-1, first inboard arm 422-2, second inboard arm 422-3, and second outboard arm 422-4. For ease of reference, only electrodes 424-1, 424-2, 424-3 are referenced herein, however the principles discussed with respect to the electrodes 424-1, 424-2, 424-3 apply to other electrodes depicted in FIG. 8A, as well. As depicted in FIG. 8A, 16 electrodes can be disposed on the flexible framework.

In some embodiments, a spacing between each of the horizontally spaced electrodes can be equal. As used herein, the terms "horizontally spaced" and "horizontal spacing" can be used interchangeably with the terms "laterally spaced" and "lateral spacing," respectively. For example, a spacing between the electrodes 424-1, 424-3 can be equal to the other horizontally spaced electrodes disposed on the flexible framework 420. In some embodiments, a spacing between each one of the horizontally spaced electrodes (e.g., electrodes 424-1, 424-3) can be in a range from 2 to 5 millimeters. In some embodiments, the spacing between each one of the horizontally spaced electrodes (e.g., electrodes 424-1, 424-3) can be 4 millimeters.

In some embodiments, a spacing between each of the vertically spaced electrodes can be equal. As used herein, the terms "vertically spaced" and "vertical spacing" can be used interchangeably with the terms "longitudinally spaced" and "longitudinal spacing," respectively. For example, a spacing between the electrodes 424-1, 424-2 can be equal to the other vertically spaced electrodes disposed on the flexible framework 420. In some embodiments, a spacing between each one of the vertically spaced electrodes (e.g., electrodes 424-1, 424-2) can be in a range from 2 to 5 millimeters. In some embodiments, the spacing between each one of the vertically spaced electrodes (e.g., electrodes 424-1, 424-2) can be 4 millimeters.

As depicted in FIG. 8B, a plurality of electrodes 430-1, 430-2, . . . , 430-11 are disposed on a flexible framework 426 formed from a plurality of arms 428-1, 428-2, . . . , 428-5, including a first outboard arm 428-1, first inboard arm 428-2, central arm 428-3, second inboard arm 428-4, and second outboard arm 428-5. In some embodiments, a greater density of electrodes can be disposed on the first inboard arm 428-2, central arm 432, and second inboard arm 428-4. For ease of reference, only electrodes 424-1, 424-2, . . . , 424-9 are referenced herein, however the principles discussed with respect to the electrodes 424-1, 424-2, . . . , 424-9 apply to other electrodes depicted in FIG. 8B, as well. As depicted in FIG. 8B, 29 electrodes can be disposed on the flexible framework In some embodiments, a spacing between each of the horizontally spaced electrodes disposed on the first outboard arm 428-1, first inboard arm 428-2, second inboard arm 428-4, and second outboard arm 428-5 can be equal (e.g., electrodes 430-1, 430-2, 430-4, 430-5). In some embodiments, a spacing between each one of the horizontally spaced electrodes (e.g., 424-1, 424-3) can be in a range from 2 to 5 millimeters. In some embodiments, the spacing between each one of the horizontally spaced electrodes (e.g., 424-1, 424-3) can be 4 millimeters.

In some embodiments, a spacing between each of the vertically spaced electrodes on the first and second outboard arms 428-1, 428-5 can be equal (e.g., electrodes 430-1, 430-8). In some embodiments, although a higher density of electrodes is disposed on the first and second inboard arms 428-2, 428-4 and central arm 428-3, the spacing between each of the vertically spaced electrodes on the first and second outboard arms 428-1, 428-5 (e.g., electrodes 430-1, 430-8) can be maintained between particular electrodes disposed on the first inboard arm 428-2, central arm 428-3, and second inboard arm 428-4 (e.g., electrodes 430-2, 430-9). For example, the spacing between the electrodes 430-2, 430-9 disposed on the second inboard arm 428-4 can be equal to the spacing between the electrodes 430-1, 430-8 disposed on the second outboard arm 428-5. In some embodiments, a spacing between each one of the vertically spaced electrodes (e.g., 430-1, 430-8) can be in a range from 2 to 5 millimeters. In some embodiments, the spacing between each one of the vertically spaced electrodes (e.g., 424-1, 424-8) can be 4 millimeters.

In some embodiments, a spacing between the electrodes disposed on the first and second inboard arms 428-2, 428-4 and the central arm 428-3 (e.g., electrodes 430-2, 430-3, 430-6, 430-7) can include a smaller spacing between the electrodes disposed on the first outboard arm 428-1 and second outboard arm 428-5 (e.g., electrodes 430-1, 430-8), resulting in a greater density of electrodes disposed on the first inboard arm 428-2, central arm 428-3, and second inboard arm 428-3. In some embodiments, the greater density of electrodes disposed on the first inboard arm 428-2, central arm 428-3, and second inboard arm 428-3 can result a flexible framework 426 that can provide a greater granularity of sensing. In some embodiments where the electrodes are used for ablation, the greater density of electrodes disposed on the first inboard arm 428-2, central arm 428-3, and second inboard arm 428-3 can provide for a more dense ablation pattern.

In some embodiments, a spacing between each one of the vertically spaced electrodes disposed on the first inboard arm 428-2, central arm 428-3, and second inboard arm 428-3 (e.g., electrodes 430-2, 430-6 and electrodes 430-3, 430-7) can be in a range from 1 to 3 millimeters. In some embodiments, the spacing between each one of the vertically spaced electrodes (e.g., electrodes 430-2, 430-6 and electrodes 430-3, 430-7) can be 2 millimeters. In some embodiments, a spacing between each one of the horizontally spaced electrodes disposed on the first inboard arm 428-2, central arm 428-3, and second inboard arm 428-3 (e.g., electrodes 430-3, 430-2 and electrodes 430-7, 430-6) can be in a range from 1 to 3 millimeters. In some embodiments, the spacing between each one of the horizontally spaced electrodes (e.g., electrodes 430-3, 430-2 and electrodes 430-7, 430-6) can be 2 millimeters.

In some embodiments, a first plurality of electrodes can be disposed on the first and second outboard arms 428-1, 428-5, the first and second inboard arms 428-2, 428-4, and the central arm 432 (e.g., electrodes 430-1, 430-2, 430-4, 430-5, 430-8, 430-9, 430-10, 430-11) and can have an equal spacing therebetween. In an example, a spacing between each one of the electrodes 430-1, 430-2, 430-4, 430-5, 430-8, 430-9, 430-10, 430-11 can be of a first dimension (e.g., 2 millimeters). In some embodiments, a second plurality of electrodes can be disposed on the first and second inboard arms 428-2, 428-4 and the central arm 432 (e.g., electrodes 430-2, 430-3, 430-6, 430-7) and can have an equal spacing therebetween. In an example, a spacing between each one of the electrodes 430-2, 430-3, 430-6, 430-7 can be of a second dimension (e.g., 1 millimeters). In some embodiments, the second dimension can be of a smaller dimension than the first dimension, thus providing a greater density of electrodes disposed on the first and second inboard arms 428-2, 428-4 and the central arm 432.

As further depicted, the flexible framework 426 can include a magnetic position sensor 432 disposed on a distal portion of the central arm 428-3. In some embodiments, a position of the magnetic position sensor 432 can be determined and thus a position of the distal portion of the flexible framework 426 can be determined. The magnetic position sensor 432 can be a five degree of freedom sensor and/or six degree of freedom sensor. Although the magnetic position sensor 432 is depicted as being disposed on the central arm 428-3, the magnetic position sensor 432 can be disposed on other portions of the flexible framework. In some embodiments, the magnetic position sensor 432 is not limited to a single magnetic position sensor and may include more than one magnetic position sensor. In some embodiments, as previously discussed herein, the magnetic position sensor 432 can be disposed in a magnetic position sensor mount, which also acts as an additional electrode. Thus, in some embodiments, the flexible framework 426 can include 30 electrodes.

As depicted in FIG. 8C, a plurality of electrodes 442-1, 442-2, 442-3 are disposed on a flexible framework 438 formed from a plurality of arms 440-1, 440-2, . . . , 440-5, including a first outboard arm 440-1, first inboard arm 440-2, a central arm 440-3, a second inboard arm 440-4, and second outboard arm 440-5. In some embodiments, the plurality of arms 440-1, 440-2, . . . , 440-5 can include an equal density of electrodes 442-1, 442-2, 442-3. For ease of reference, only electrodes 442-1, 442-2, 442-3 are referenced herein, however the principles discussed with respect to the electrodes 440-1, 440-2, 440-3 apply to other electrodes depicted in FIG. 8C, as well. As depicted in FIG. 8C, 25 electrodes can be disposed on the flexible framework.

In some embodiments, a spacing between each of the horizontally spaced electrodes can be equal. For example, a spacing between the electrodes 442-1, 442-3 can be equal to the other horizontally spaced electrodes disposed on the flexible framework 438. In some embodiments, a spacing between each one of the horizontally spaced electrodes (e.g., electrodes 442-1, 442-3) can be in a range from 2 to 4 millimeters. In some embodiments, the spacing between each one of the horizontally spaced electrodes (e.g., electrodes 442-1, 442-3) can be 3 millimeters. In some embodiments, a spacing between each of the vertically spaced electrodes can be equal. For example, a spacing between the electrodes 442-1, 442-2 can be equal to the other vertically spaced electrodes disposed on the flexible framework 438. In some embodiments, a spacing between each one of the vertically spaced electrodes (e.g., electrodes 442-1, 442-2) can be in a range from 2 to 4 millimeters. In some embodiments, the spacing between each one of the vertically spaced electrodes (e.g., electrodes 442-1, 442-2) can be 3 millimeters.

As further depicted, the flexible framework 438 can include a magnetic position sensor 444 disposed on a distal portion of the central arm 440-3. In some embodiments, the magnetic position sensor 444 can be used in determination of a position and orientation of the distal portion of the flexible framework. The magnetic position sensor 444 can be a five degree of freedom sensor and/or six degree of freedom sensor. In some embodiments, as previously discussed herein, the magnetic position sensor 444 can be disposed in a magnetic position sensor mount, which also acts as an additional electrode. Thus, in some embodiments, the flexible framework 438 can include 30 electrodes.

As depicted in FIG. 8D, a plurality of electrodes 454-1, 454-2, 454-3 are disposed on a flexible framework 450 formed from a plurality of arms 452-1, 452-2, . . . , 422-6, including a first outboard arm 452-1, first middle arm 452-2, first inboard arm 452-3, second outboard arm 452-4, second middle arm 452-5, second outboard arm 452-6. For ease of reference, only electrodes 454-1, 454-2, 454-3 are referenced herein, however the principles discussed with respect to the electrodes 454-1, 454-2, 454-3 apply to other electrodes depicted in FIG. 8D, as well. As depicted in FIG. 8D, 36 electrodes can be disposed on the flexible framework 450.

In some embodiments, a spacing between each of the horizontally spaced electrodes can be equal. For example, a spacing between the electrodes 454-1, 454-3 can be equal to the other horizontally spaced electrodes disposed on the flexible framework 450. In some embodiments, a spacing between each one of the horizontally spaced electrodes (e.g., electrodes 454-1, 454-3) can be in a range from 1.4 to 3.4 millimeters. In some embodiments, the spacing between each one of the horizontally spaced electrodes (e.g., electrodes 454-1, 454-3) can be 2.4 millimeters.

In some embodiments, a spacing between each of the vertically spaced electrodes can be equal. For example, a spacing between the electrodes 454-1, 454-2 can be equal to the other vertically spaced electrodes disposed on the flexible framework 450. In some embodiments, a spacing between each one of the vertically spaced electrodes (e.g., electrodes 454-1, 454-2) can be in a range from 1.4 to 3.4 millimeters. In some embodiments, the spacing between each one of the vertically spaced electrodes (e.g., electrodes 454-1, 454-2) can be 2.4 millimeters.

As depicted in FIG. 8E, a plurality of electrodes 462-1, 462-2, 462-3 are disposed on a flexible framework 460 formed from a plurality of arms 462-1, 462-2, . . . , 462-7, including a first outboard arm 462-1, first middle arm 462-3, first inboard arm 463-3, central arm 462-4, second inboard arm 462-5, second middle arm 462-6, and second outboard arm 462-7. For ease of reference, only electrodes 462-1, 462-2, 462-3 are referenced herein, however the principles discussed with respect to the electrodes 462-1, 462-2, 462-3 apply to other electrodes depicted in FIG. 8E, as well. As depicted in FIG. 8E, 49 electrodes can be disposed on the flexible framework 460.

In some embodiments, a spacing between each of the horizontally spaced electrodes can be equal. For example, a spacing between the electrodes 464-1, 464-3 can be equal to the other horizontally spaced electrodes disposed on the flexible framework 460. In some embodiments, a spacing between each one of the horizontally spaced electrodes (e.g., electrodes 464-1, 464-3) can be in a range from 1 to 3 millimeters. In some embodiments, the spacing between each one of the horizontally spaced electrodes (e.g., electrodes 464-1, 464-3) can be 2 millimeters. In some embodiments, a spacing between each of the vertically spaced electrodes can be equal. For example, a spacing between the electrodes 464-1, 464-2 can be equal to the other vertically spaced electrodes disposed on the flexible framework 460. In some embodiments, a spacing between each one of the vertically spaced electrodes (e.g., electrodes 464-1, 464-2) can be in a range from 0.5 to 3 millimeters. In some embodiments, the spacing between each one of the vertically spaced electrodes (e.g., electrodes 464-1, 464-2) can be 2 millimeters.

As further depicted, the flexible framework 460 can include a magnetic position sensor 466 disposed on a distal portion of the central arm 462-4. In some embodiments, the magnetic position sensor 466 can be used in determination of a position and orientation of the distal portion of the flexible framework. The magnetic position sensor 466 can be a five degree of freedom sensor and/or six degree of freedom sensor. In some embodiments, as previously discussed herein, the magnetic position sensor 466 can be disposed in a magnetic position sensor mount, which also acts as an additional electrode. Thus, in some embodiments, the flexible framework 438 can include 50 electrodes.

Figure 9:
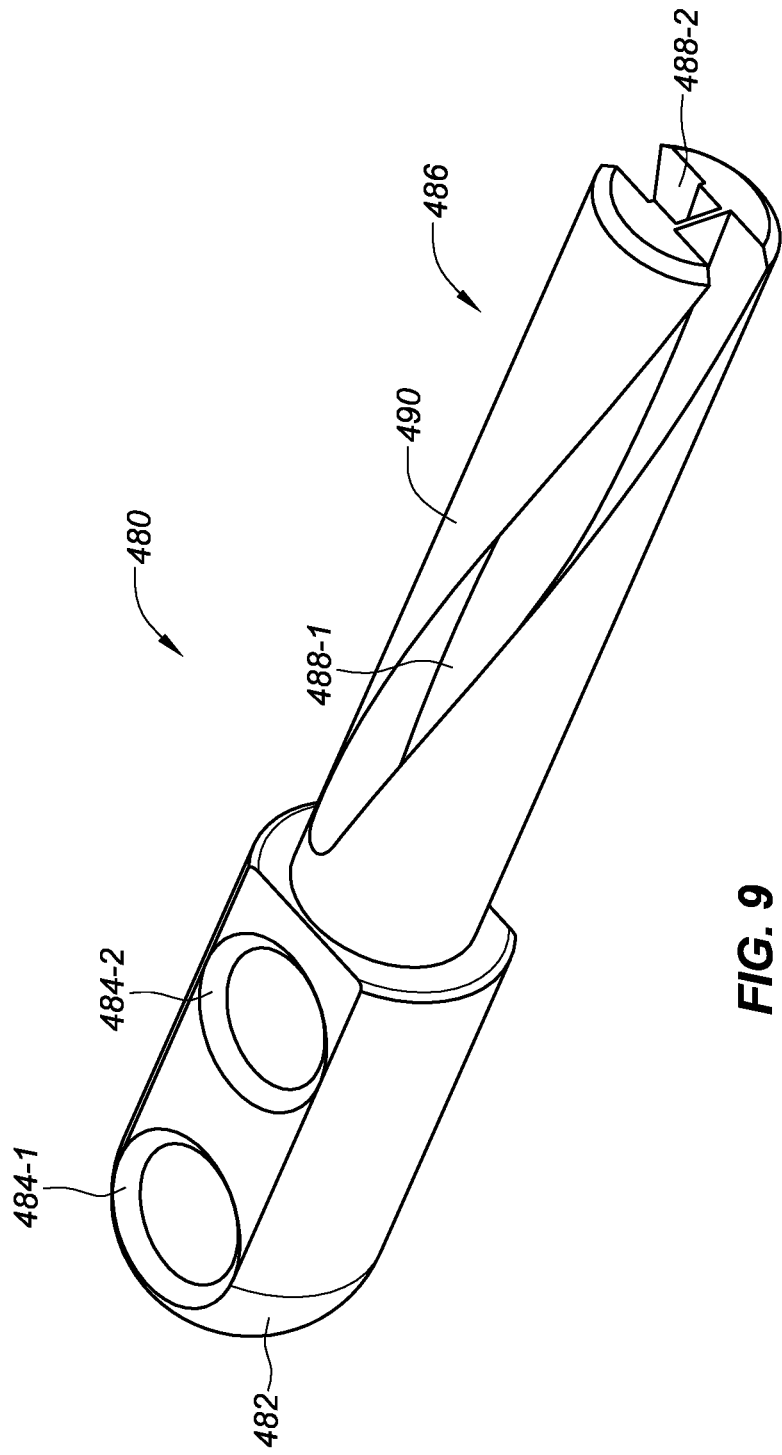
FIG. 9 is an isometric rear view of a distal tip assembly that includes a magnetic position sensor mount and a distal coupler, in accordance with embodiments of the present disclosure.

FIG. 9 is an isometric rear view of a distal tip assembly 480 that includes a magnetic position sensor mount 486 and a distal coupler 482, in accordance with embodiments of the present disclosure. As depicted, the distal coupler 482 can define one or more transverse lumens 484-1, 484-2 extending therethrough, as discussed herein. One or more arms (not depicted), associated with a flexible framework can be disposed through the one or more transverse lumens 484-1, 484-2. In some embodiments, a magnetic position sensor mount 486 can extend proximally from the distal coupler 482. In some embodiments, the magnetic position sensor mount 486 can include first and second sensor grooves 488-1, 488-2 (FIG. 9) defined in an outer surface 490 of the magnetic position sensor mount 486. In some embodiments, the first and second sensor grooves 488-1, 488-2 can be angled with respect to one another and/or with respect to a longitudinal axis of the magnetic position sensor mount 486. In some embodiments, the first and second sensor grooves 488-1, 488-2, as well as magnetic position sensors, further depicted in FIG. 10, disposed in the first and second sensor grooves 488-1, 488-2 can include those features discussed in relation to U.S. patent application Ser. No. 15/585,859, which is hereby incorporated by reference as though fully set forth herein.

For example, in some embodiments, the magnetic position sensors can be canted with respect to one another, when disposed in the first and second sensor grooves 488-1, 488-2. This can allow for a determination of a roll of the magnetic position sensor mount 486 and associated distal coupler 482 and thus determination of a roll of the flexible framework connected to the distal coupler 482 and/or the magnetic position sensor mount 486.

Although the magnetic position sensor mount 486 is depicted as being connected to the distal coupler 482, the magnetic position sensor mount 486 can be disposed along other portions of the flexible framework of a high-density electrode catheter, as discussed herein. For example, the magnetic position sensor mount 486 and associated magnetic position sensors can be disposed along a central arm, inboard arm, middle arm, and/or outboard arm, as discussed herein.

As further discussed herein, in some embodiments, the magnetic position sensor mount 486 can form an electrode. In some embodiments, an electrically conductive material, not depicted, can surround the magnetic position sensor mount 486, which can form the electrode. For example, a central electrode 130, such as that depicted and discussed in relation to at least FIG. 3A can be disposed over the magnetic position sensor mount 486.

Figure 10:
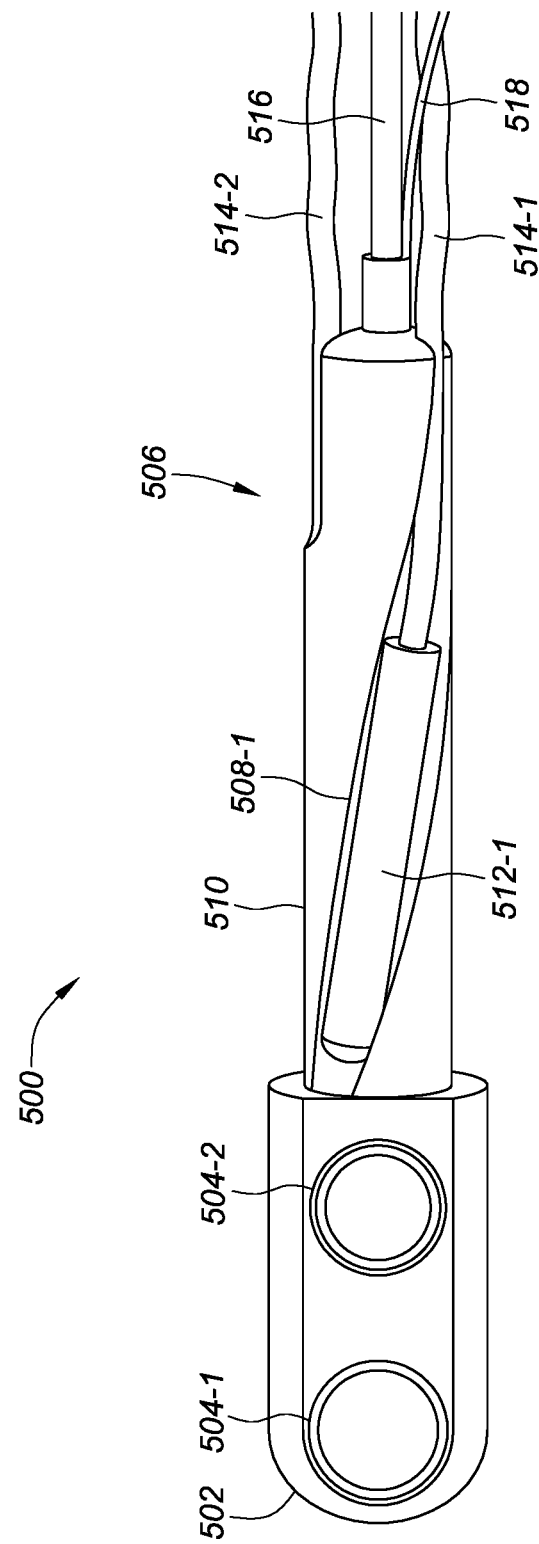
FIG. 10 is a side view of a distal tip assembly that includes a magnetic position sensor mount and a distal coupler, in accordance with embodiments of the present disclosure.

FIG. 10 is a side view of a distal tip assembly 500 that includes a magnetic position sensor mount 506 and a distal coupler 502, in accordance with embodiments of the present disclosure. As depicted, the distal coupler 502 can define one or more transverse lumens 504-1, 504-2 extending therethrough, as discussed herein. One or more arms (not depicted), associated with a flexible framework can be disposed through the one or more transverse lumens 504-1, 504-2. In some embodiments, a magnetic position sensor mount 506 can extend proximally from the distal coupler 502. In some embodiments, the magnetic position sensor mount 506 can include first and second sensor grooves 508-1, 508-2 (FIG. 9) defined in an outer surface 510 of the magnetic position sensor mount 506. In some embodiments, the first and second sensor grooves 508-1, 508-2 can be angled with respect to one another and/or with respect to a longitudinal axis of the magnetic position sensor mount 506. In some embodiments, the first and second sensor grooves 508-1, 508-2, as well as magnetic position sensors 512-1 (magnetic position sensor 512-2 is hidden from view), disposed in the first and second sensor grooves 508-1 (sensor groove 508-2 is hidden from view) can include those features discussed in relation to U.S. patent application Ser. No. 15/585,859, which is hereby incorporated by reference as though fully set forth herein.

For example, in some embodiments, the magnetic position sensors 512-1, 512-2 can be canted with respect to one another, when disposed in the first and second sensor grooves 508-1, 508-2. This can allow for a determination of a roll of the magnetic position sensor mount 506 and associated distal coupler 502 and thus determination a roll of the flexible framework connected to the distal coupler 502 and/or the magnetic position sensor mount 506.

Although the magnetic position sensor mount 506 is depicted as being connected to the distal coupler 502, the magnetic position sensor mount 506 can be disposed along other portions of the flexible framework of a high-density electrode catheter, as discussed herein. For example, the magnetic position sensor mount 506 and associated magnetic position sensors can be disposed along a central arm, inboard arm, middle arm, and/or outboard arm, as discussed herein.

As depicted in FIG. 10, a first and second twisted pair of wires 514-1, 514-2 can electrically couple the magnetic position sensors 512-1, 512-2 to one or more of the computer systems 20, 64, depicted in FIGS. 1A and 1B. As further depicted in FIG. 10, an electrode wire 518 is depicted as extending from the proximal end of the magnetic position sensor mount 506, which can be electrically coupled with an electrode disposed on the magnetic position sensor mount and one or more of the computer systems 20, 64. Also depicted as extending from the proximal end of the magnetic position sensor mount is a central frame 516 of a flexible framework, as discussed herein. In some embodiments, the central frame 516 can be coupled to the proximal end of the magnetic position sensor mount 506, as discussed herein, for example in relation to FIGS. 3J and 3S.

Figure 11:
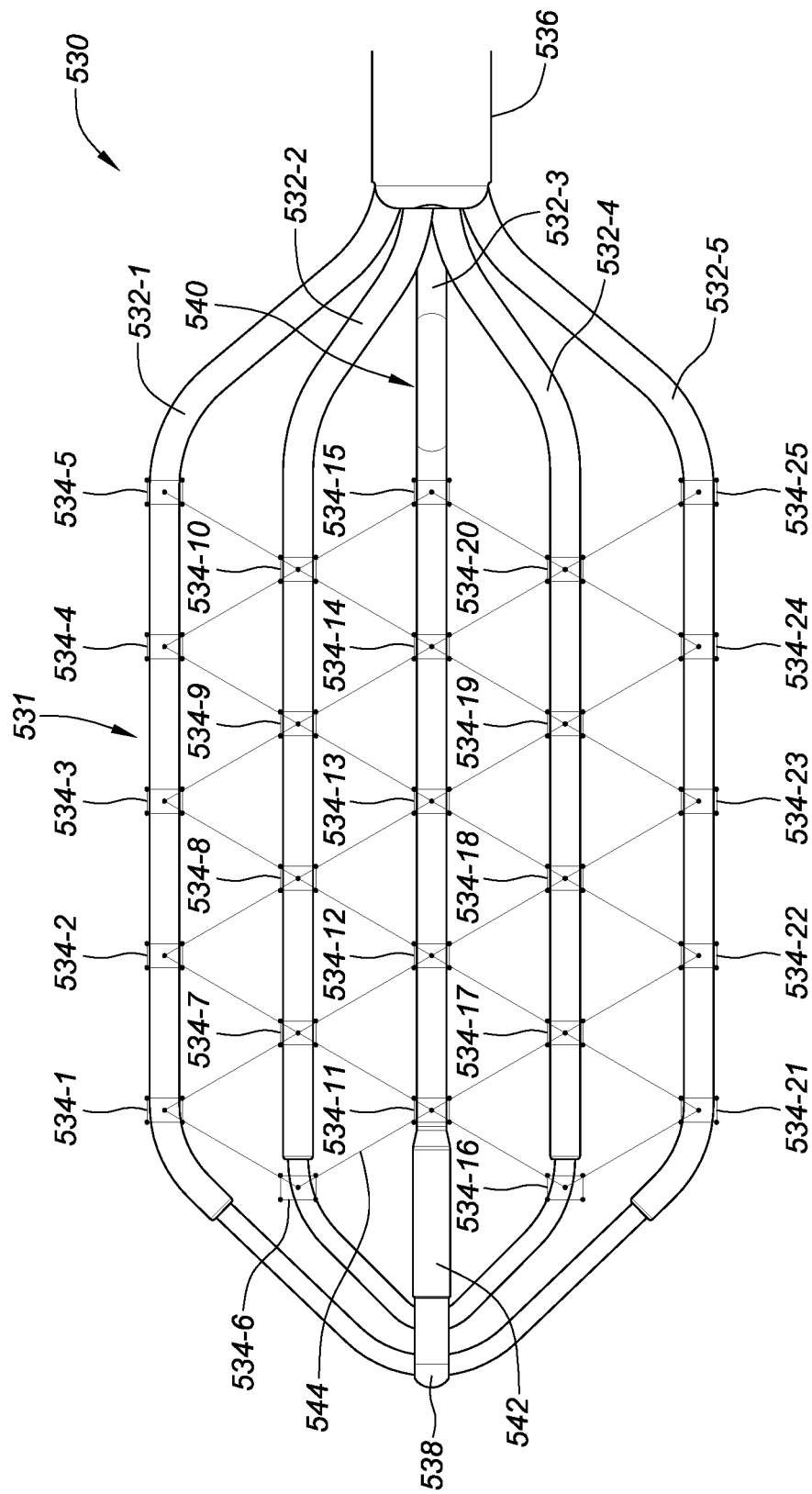
FIG. 11 is a top view of a high-density electrode catheter with staggered electrodes, in accordance with embodiments of the present disclosure.

FIG. 11 is a top view of a high-density electrode catheter 530 with staggered electrodes 534-1, 534-2, . . . , 534-25, in accordance with embodiments of the present disclosure. As depicted, the high-density electrode catheter 530 can include a flexible framework formed from a first outboard arm 532-1, first inboard arm 532-2, central arm 532-3, second inboard arm 532-4, and second outboard arm 532-5. In some embodiments, the proximal ends of the arms 532-1, 532-2, . . . 532-5 can be disposed in a proximal coupler 536, as discussed herein, which can be mounted on a distal end of a catheter shaft, not depicted. The distal ends of the arms 532-1, 532-2, . . . , 532-5 can be mounted with a distal coupler 538. However, in some embodiments, the arms 532-1, 532-2, . . . , 532-5 may not be coupled to one another.

As depicted, the central arm 532-3 can include a lengthening feature 540, as discussed herein. In some embodiments, the central arm 532-3 can include an electrode 542 disposed at a distal end of the central arm 532-3. In some embodiments, a core of the electrode 542 can include a magnetic position sensor (not depicted), which can be used to determine a position and/or orientation of the flexible framework 531.

In some embodiments, as depicted, each of the arms 532-1, 532-2, . . . , 532-5 can include electrodes 534-1, 534-2, . . . , 534-25 disposed thereon. As depicted, the electrodes on each of the arms 532-1, 532-2, . . . , 532-5 can be staggered with respect to one another. For example, with respect to the first outboard arm 532-1, the electrodes 534-1, 534-2, . . . , 534-5 can be staggered with respect to the electrodes 534-6, 534-7, . . . , 534-10 disposed on the first inboard arm 532-2. As depicted, the electrodes 534 disposed on each arm can be staggered with respect to the electrodes 534 disposed on each adjacent arm.

In some embodiments, cliques (e.g., groups) of electrodes 534 can be formed with the electrodes 534 disposed on the first inboard arm 532-2 and the electrodes 534 disposed on the first outboard arm 532-1 and central arm 532-3; cliques of electrodes 534 can be formed with the electrodes 534 disposed on the central arm 532-3 and the electrodes 534 disposed on the first inboard arm 532-2 and second inboard arm 532-4; and/or cliques of electrodes 534 can be formed with the electrodes 534 disposed on the second inboard arm 532-4 and the electrodes 534 disposed on the central 532-3 and second outboard arm 532-5. For example, with respect to the first outboard arm 532-1, first inboard arm 532-2, and central arm 532-3 a clique of electrodes 534-1, 534-6, 534-7, 534-11, represented by parallelogram 544.

In some embodiments, staggering of the electrodes 534-1, 534-2, . . . , 534-25 disposed on each of the arms 532-1, 532-2, . . . , 532-5 can be advantageous, as it provides a compromise between spacing between each of the electrodes 534-1, 534-2, . . . , 534-25 and a total number of electrodes 534-1, 534-2, . . . , 534-25. In an example, a spacing between each electrode in the clique of electrodes 543-1, 534-6, 534-7, 534-11 can be the same. For instance, a spacing between electrodes 534-1 and 534-7 can be the same as a spacing between electrodes 534-1 and 534-6, which can be the same as a spacing between electrodes 534-6 and 534-7. Embodiments depicted and discussed in relation to FIG. 11 can allow for a decreased spacing between electrodes 534, while using a same number of electrodes as an embodiment where the electrodes 534-1, 534-2, . . . , 534-25 are not staggered. In some embodiments where the electrodes are not staggered, but are aligned with one another along a cross-longitudinal axis of a flexible tip portion, a greater number of electrodes and/or a greater number of arms can be needed to obtain a same spacing between a staggered set of electrodes, such as that depicted in relation to FIG. 11.

Figure 12A:
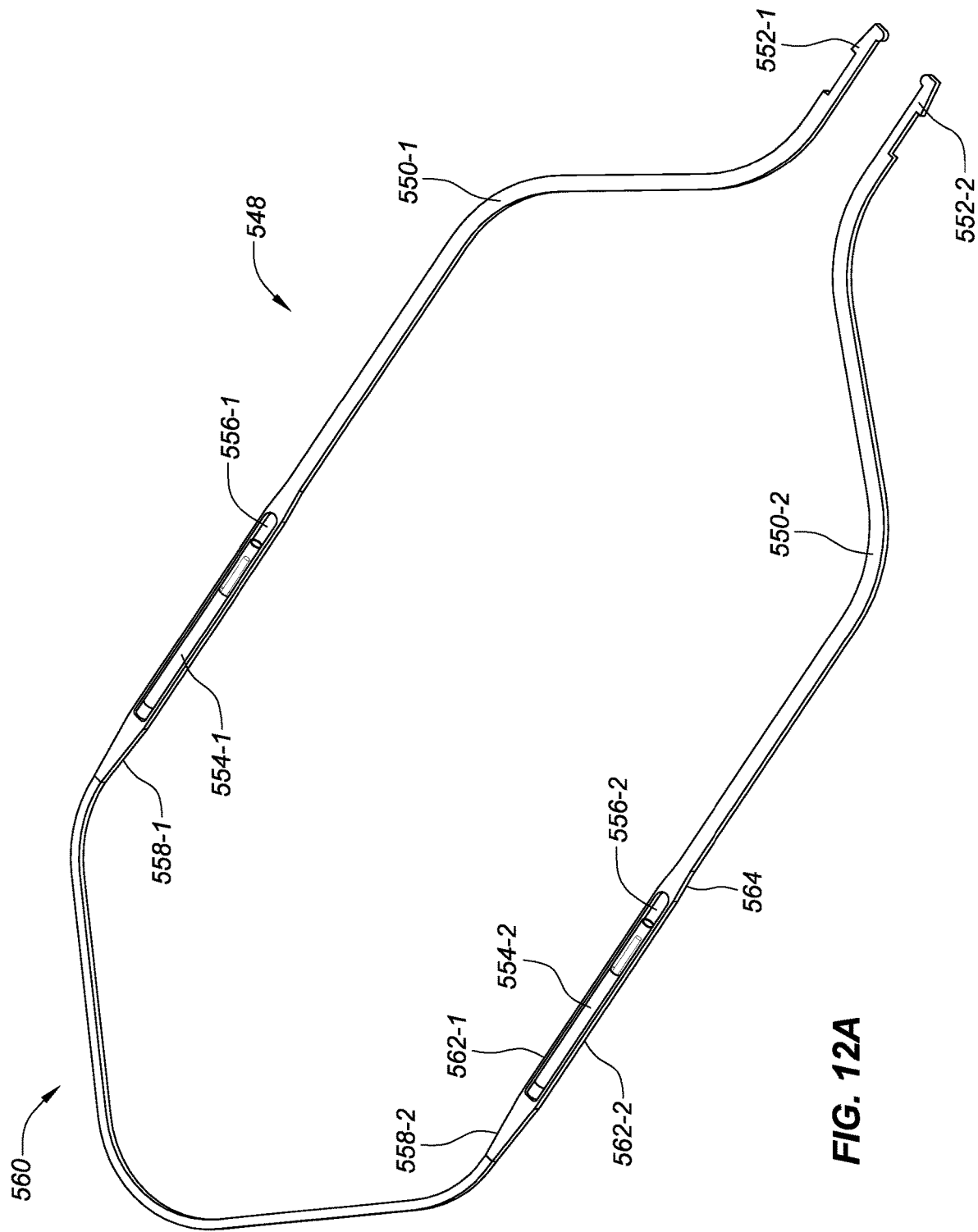
FIG. 12A is a top view of an understructure of a flexible tip of a high-density electrode catheter that includes magnetic position sensors in an outboard frame, in accordance with embodiments of the present disclosure.

FIG. 12A is a top view of an understructure 548 of a flexible tip of a high-density electrode catheter that includes magnetic position sensors 554-1, 554-2 in an outboard frame, in accordance with embodiments of the present disclosure. As depicted, the understructure 548 can include a first outboard frame 550-1 and a second outboard frame 550-2. In some embodiments, FIG. 12A depicts a portion of an entire understructure associated with a flexible tip of a high-density electrode catheter. For example, FIG. 12A depicts the outboard understructure portion of the entire understructure, which can also include a middle frame and/or an inboard frame, as further discussed herein. For example, the understructure to which the first and second outboard frames 550-1, 550-2 belong to can have a total of two arms to eight arms, although embodiments of the present disclosure can include more than eight arms, in some embodiments. As depicted, the first and second frames 550-1, 550-2 can include frame mounting portions 552-1, 552-2.

In some embodiments, magnetic position sensors 554-1, 554-2 can be disposed along the first and second outboard frames 550-1, 550-2, as depicted in FIG. 12A. In some embodiments, the magnetic position sensors 554-1, 554-2 can be disposed along a top, bottom, inside, and/or outside of each one of the first and second outboard frames 550-1, 550-2. In some embodiments, the first and second outboard frames 550-1, 550-2 can include mounting features, which can be configured to allow for the magnetic position sensors 554-1, 554-2 to be mounted along the first and second outboard frames 550-1, 550-2.

In some embodiments, as depicted, the first and second outboard frames 550-1, 550-2 can include slots 556-1, 556-2 defined along a longitudinally extending portion of the first and second outboard frames 550-1, 550-2. As depicted, in some embodiments, the slots 556-1, 556-2 define a central mounting space that longitudinally extends along the first and second outboard frames 550-1, 550-2. As depicted, the slots 556-1, 556-2 and associated magnetic position sensors 554-1, 554-2 are depicted as being located proximal to shoulder portions 558-1, 558-2. In some embodiments, the magnetic position sensors 554-1, 554-2 can be located along other portions of the first and second outboard frames 550-1, 550-2. For example, the magnetic position sensors 554-1, 554-2 can be located proximally from their locations depicted in FIG. 12A, along the outboard frames 550-1, 550-2. In some embodiments, the magnetic position sensors 554-1, 554-2 can be located in a proximal tip portion 560 of the outboard understructure. Although two magnetic position sensors 554-1, 554-2 are depicted as being disposed along the outboard frames 550-1, 550-2, fewer than or greater than two magnetic position sensors 554-1, 554-2 can be disposed along the outboard frames 550-1, 550-2.

In some embodiments, as discussed, the slots 556-1, 556-2 can be defined in portions of the first and second outboard frames 550-1, 550-2. With respect to the second slot 556-2, the slot can be defined along the second outboard frame 550-2, such that a pair of slot frames 562-1, 562-2 define the slot 556-2. For example, in some embodiments, the second outboard frame 550-2 can be cut, such that the slot 556-2 is defined, leaving behind the first and second slot frames 562-1, 562-2. In some embodiments, the portion of the outboard frame 550-2 where the slot 556-2 is defined can be widened, such that when material is removed from the outboard frame 550-2 to define the slot 556-2, a lateral width of each slot frame 562-1, 562-2 combined can match a lateral width of the outboard frame 550-2. As can be seen, the portion of the outboard frame 550-2 includes a flare 564, such that the portion of the outboard frame 550-2 that includes the magnetic position sensor 554-2 is wider than other longitudinally extending portions of the outboard frame 550-2. In some embodiments, a total lateral width of the slot frames 562-1, 562-2 can be less than or greater than a lateral width of the other longitudinally extending portions of the outboard frame 550-2, for example, longitudinally extending portions of the outboard frame 550-2 located proximally to the slot frames 562-1, 562-2. Accordingly, even though a slot 556-2 is defined in the outboard frame 550-2, a flexibility of the portion of the outboard frame 550-2 that includes the magnetic position sensor can match or come close to matching the flexibility of the other longitudinally extending portions of the outboard frame 550-2, such as those located proximally to the magnetic position sensor 554-2. Although the above discussion is directed towards the second outboard frame 550-2, the same can be true for other frames.

As depicted, the magnetic position sensor 554-2 can be located between the slot frames 562-1, 562-2. In some embodiments, a top and bottom surface of the magnetic position sensor can be even with a top and bottom surface of the outboard frame 550-2. In some embodiments, a top and bottom surface of the magnetic position sensor 554-2 can protrude above or be recessed below the top and/or bottom surface of the outboard frame 550-2.

In some embodiments, the slots 556-1, 556-2 can be defined via laser cutting. For example, in some embodiments, the understructure 548 can be defined by laser cutting, including the slots 556-1, 556-2. In some embodiments, the understructure 548 can be created via a mold, including the slots 556-1, 556-2. In some embodiments, the understructure 548 and the slots 556-1, 556-2 can be created by two different processes. For example, the understructure 548 can be molded and the slots 556-1, 556-2 can be defined by a laser. In some embodiments, the slots 556-1, 556-2 and the understructure 548 can each be formed by the same process.

Figure 12B:
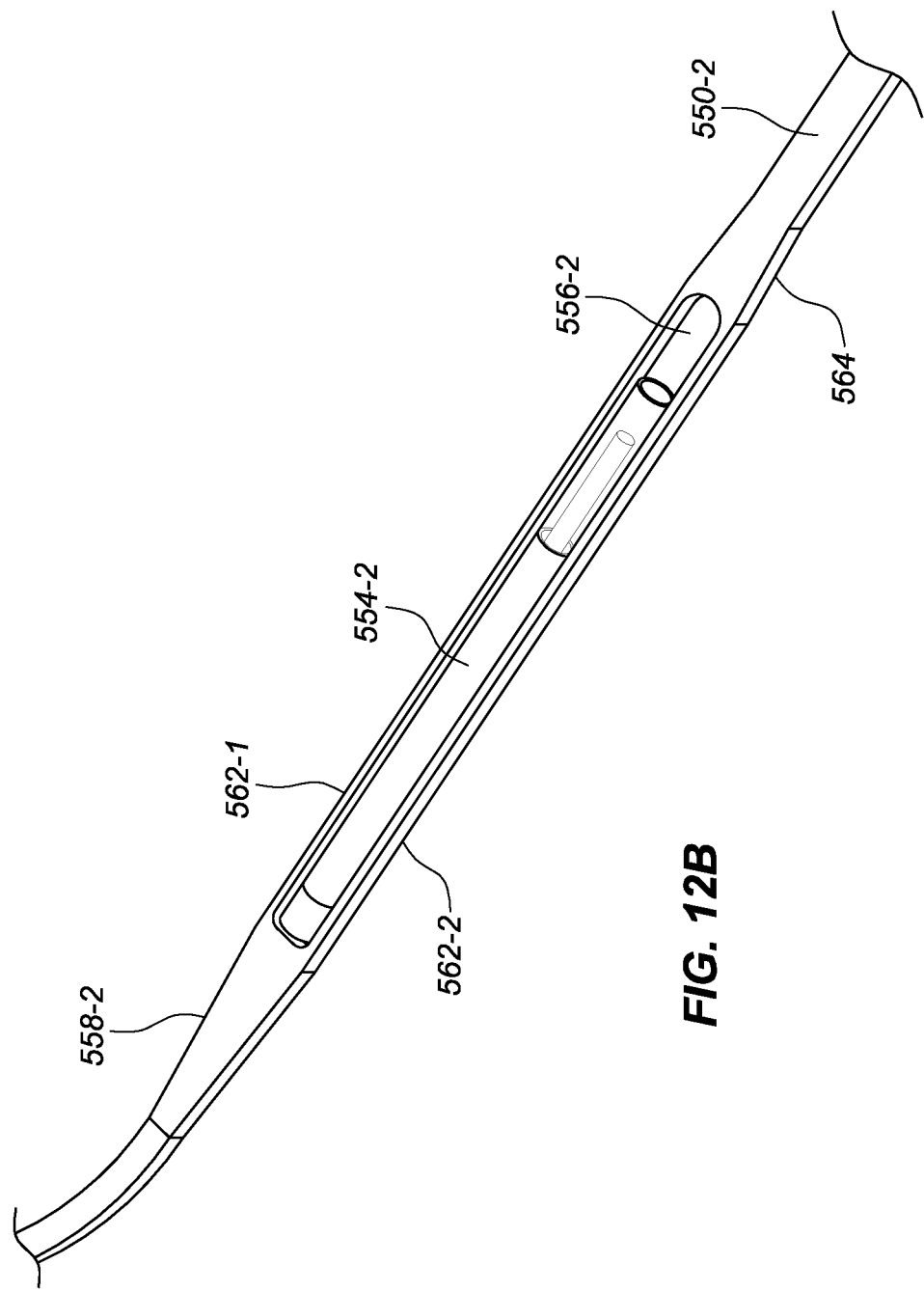
FIG. 12B is a close-up view of the understructure of the flexible tip of the high-density electrode catheter depicted in FIG. 12A, further depicting the magnetic position sensor in the outboard frame, in accordance with embodiments of the present disclosure.

FIG. 12B is a close-up view of the understructure of the flexible tip of the high-density electrode catheter depicted in FIG. 12A, further depicting the magnetic position sensor 554-2 in the outboard frame 550-2, in accordance with embodiments of the present disclosure. In some embodiments, the outboard framework 550-2 can define a slot 556-2, which is defined by slot frames 562-1, 562-2. As depicted, the magnetic position sensor 554-2 can be disposed between the slot frames 562-1, 562-2. In some embodiments, a channel can be defined in the outboard frame 550-2. For example, as depicted in FIG. 12B, a pass through slot is defined in the outboard frame 550-2, however, in some embodiments, a channel can be defined, which can include a recessed area defined in the outboard frame 550-2. For example, the outboard frame 550-2 can be indented, such that a channel is defined in the surface of the outboard frame 550-2, thus creating a pocket for the magnetic position sensor. Accordingly, the magnetic position sensor 554-2 can be set into the channel, such that the magnetic position sensor 554-2 contacts a bottom of the channel, aiding in placement of the magnetic position sensor 554-2.

Figure 13A:
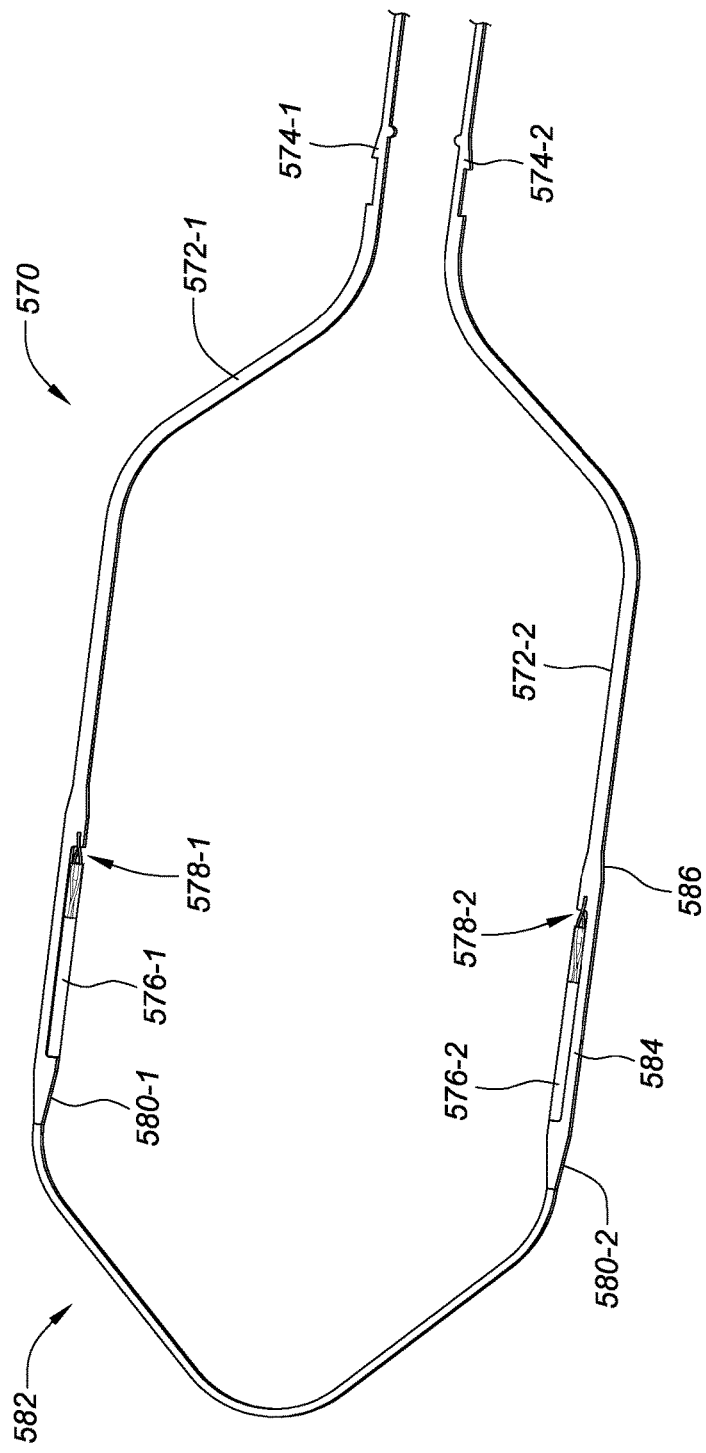
FIG. 13A is a top view of an understructure of a flexible tip of a high-density electrode catheter that includes magnetic position sensors in an outboard frame, in accordance with embodiments of the present disclosure.

FIG. 13A is a top view of an understructure 570 of a flexible tip of a high-density electrode catheter that includes magnetic position sensors 576-1, 576-2 in an outboard frame, in accordance with embodiments of the present disclosure. As depicted, the understructure 570 can include a first outboard frame 572-1 and a second outboard frame 572-2. In some embodiments, FIG. 13A depicts a portion of an entire understructure associated with a flexible tip of a high-density electrode catheter. For example, FIG. 13A depicts the outboard understructure portion of the entire understructure, which can also include a middle frame and/or an inboard frame, as further discussed herein. For example, the understructure to which the first and second outboard frames 572-1, 572-2 belong to can have a total of two arms to eight arms, although embodiments of the present disclosure can include more than eight arms in some embodiments. As depicted, the first and second frames 572-1, 572-2 can include frame mounting portions 574-1, 574-2.

In some embodiments, magnetic position sensors 576-1, 576-2 can be disposed along the first and second outboard frames 572-1, 572-2, as depicted in FIG. 13A. In some embodiments, the magnetic position sensors 576-1, 576-2 can be disposed along a top, bottom, inside, and/or outside of each one of the first and second outboard frames 572-1, 572-2. In some embodiments, the first and second outboard frames 572-1, 572-2 can include mounting features, which can be configured to allow for the magnetic position sensors 576-1, 576-2 to be mounted along the first and second outboard frames 572-1, 572-2.

In some embodiments, as depicted, the first and second outboard frames 572-1, 572-2 can include cutouts 578-1, 578-2 defined along a longitudinally extending portion of the first and second outboard frames 572-1, 572-2. As depicted, in some embodiments, the cutouts 578-1, 578-2 define a mounting space that longitudinally extends along an inside of the first and second outboard frames 572-1, 572-2. As depicted, the cutouts 578-1, 578-2 and associated magnetic position sensors 576-1, 576-2 are depicted as being located proximal to shoulder portions 580-1, 580-2. In some embodiments, the magnetic position sensors 576-1, 576-2 can be located along other portions of the first and second outboard frames 572-1, 572-2. For example, the magnetic position sensors 576-1, 576-2 can be located proximally from their locations depicted in FIG. 13A, along the outboard frames 572-1, 572-2. In some embodiments, the magnetic position sensors 576-1, 576-2 can be located in a distal tip portion 582 of the outboard understructure. Although two magnetic position sensors 576-1, 576-2 are depicted as being disposed along the outboard frames 572-1, 572-2, fewer than or greater than two magnetic position sensors 576-1, 576-2 can be disposed along the outboard frames.

In some embodiments, as discussed, the cutouts 578-1, 578-2 can be defined in portions of the first and second outboard frames 572-1, 572-2. With respect to the second cutout 578-2, the cutout can be defined along an inside edge of the second outboard frame 572-2. In some embodiments, although not depicted, the cutout 578-2 can be defined along an outside edge of the second outboard frame 572-2.

In some embodiments, the second outboard frame 572-2 can be cut, such that the cutout 578-2 is defined. In some embodiments, the portion of the outboard frame 572-2 where the cutout 578-2 is defined can be widened, such that when material is removed from the outboard frame 572-2 to define the cutout 578-2, a lateral width of a cutout frame 584 can match a lateral width of the outboard frame 572-2. As can be seen, the portion of the outboard frame 572-2 includes a flare 586, such that the portion of the outboard frame 572-2 that includes the magnetic position sensor 576-2 is wider than other longitudinally extending portions of the outboard frame 572-2. In some embodiments, a total lateral width of the cutout frame 584 can be less than or greater than a lateral width of the other longitudinally extending portions of the outboard frame 572-2, for example, longitudinally extending portions of the outboard frame 572-2 located proximally to the cutout frame 584. Accordingly, even though a cutout 578-2 is defined in the outboard frame 572-2, a flexibility of the portion of the outboard frame 572-2 that includes the magnetic position sensor can match or come close to matching the flexibility of the other longitudinally extending portions of the outboard frame 572-2, such as those located proximally to the magnetic position sensor 576-2. Although the above discussion is directed towards the second outboard frame 572-2, the same can be true for other frames.

In some embodiments, a top and bottom surface of the magnetic position sensor 576-2 can be even with a top and bottom surface of the outboard frame 572-2. In some embodiments, a top and bottom surface of the magnetic position sensor 576-2 can protrude above or be recessed below the top and bottom surface of the outboard frame 572-2.

In some embodiments, the cutouts 578-1, 578-2 can be defined via laser cutting. For example, in some embodiments, the understructure 570 can be defined by laser cutting, including the cutouts 578-1, 578-2. In some embodiments, the understructure 570 can be created via a mold, including the cutouts 578-1, 578-2. In some embodiments, the understructure 570 and the cutouts 578-1, 578-1 can be created by two different processes. For example, the understructure 570 can be molded and the cutouts 578-1, 578-2 can be defined by a laser. In some embodiments, the cutouts 578-1, 578-2 and the understructure 570 can each be defined by the same process.

Figure 13B:
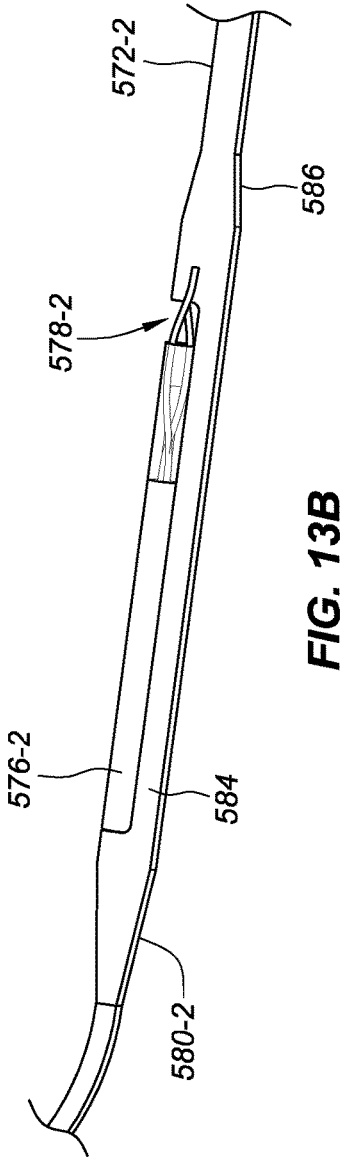
FIG. 13B is a close-up view of the understructure of the flexible tip of the high-density electrode catheter depicted in FIG. 13A, further depicting the magnetic position sensor in the outboard frame, in accordance with embodiments of the present disclosure.

FIG. 13B is a close-up view a portion of the understructure of the flexible tip of the high-density electrode catheter depicted in FIG. 13A, further depicting the magnetic position sensor 576-2 in the outboard frame 572-2, in accordance with embodiments of the present disclosure. In some embodiments, the outboard frame 572-2 can define a cutout 578-2, which is defined by cutout arm 584. As depicted, the magnetic position sensor 576-2 can be disposed on an inside of the cutout arm 584. In some embodiments, the magnetic position sensor 576-2 can be disposed on an outside of the cutout arm 584.

Figure 14:
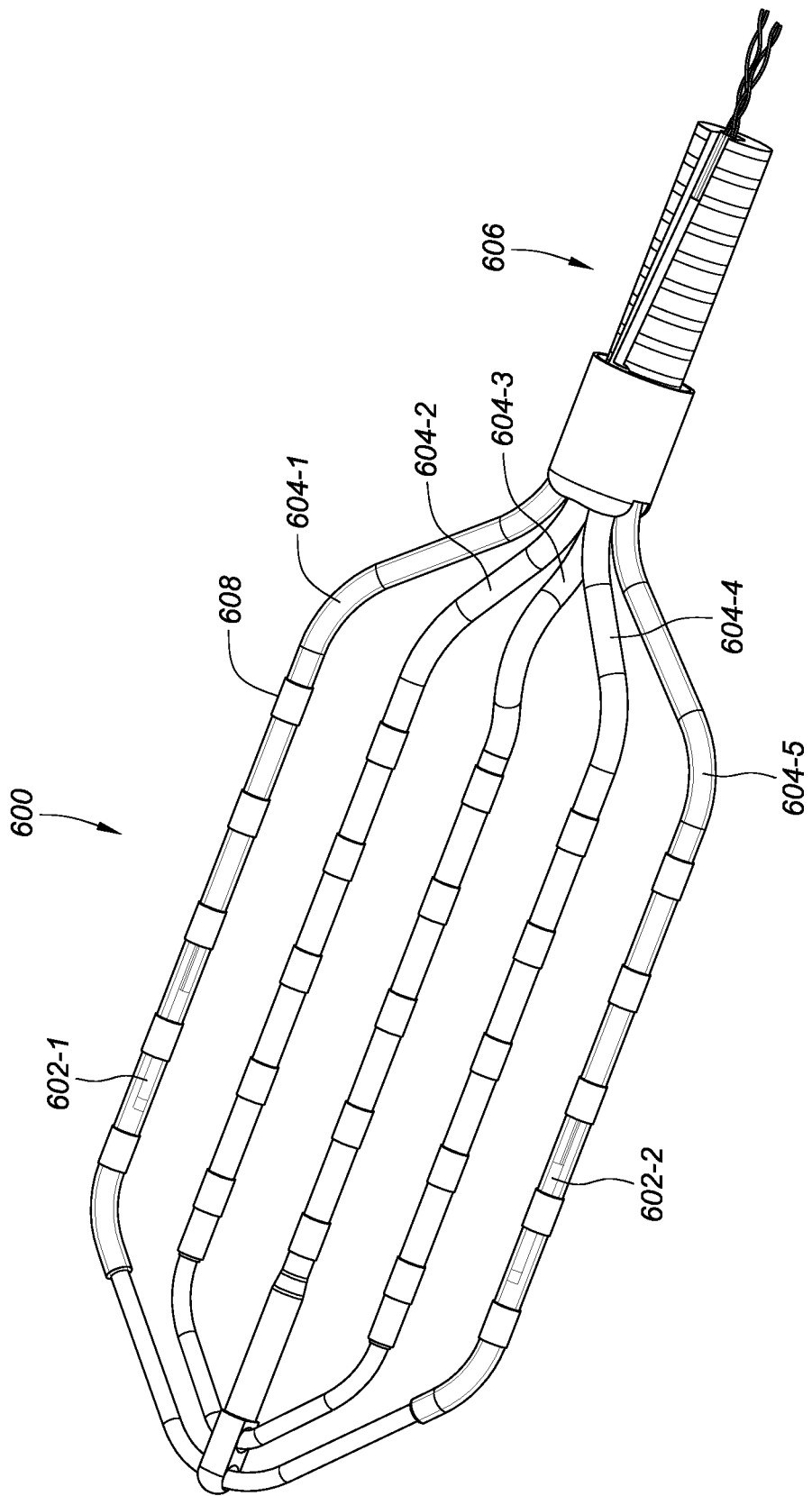
FIG. 14 is a top view of a high-density electrode catheter with magnetic position sensors disposed in the outboard arms of the high-density electrode catheter, in accordance with embodiments of the present disclosure.

FIG. 14 is a top view of a high-density electrode catheter 600 with magnetic position sensors 602-1, 602-2 disposed in the outboard arms 604-1, 604-5 of the high-density electrode catheter 600, in accordance with embodiments of the present disclosure. As depicted, the high-density electrode catheter 600 can include a proximal coupler 606, to which the longitudinally extending arms 604-1, 604-2, . . . , 604-5 are coupled, as discussed herein. In some embodiments, one or more electrodes 608 can be disposed along one or more of the arms. In some embodiments, the high-density electrode catheter 600 can include greater than or fewer than five arms 604-1, 604-2, . . . , 604-5.

In some embodiments, the high-density electrode catheter 600 can include a magnetic position sensor disposed along one or more of the longitudinally extending arms 604-1, 604-2, . . . , 604-5. As depicted, a first and second magnetic position sensor 602-1, 602-2 can be disposed along a portion of the first and second outboard arms 604-1, 604-5. In some embodiments, a frame associated with the first and second outboard arms 604-1, 604-5 can include the same or similar features to those discussed in relation to FIGS. 12A to 13B.

As depicted, the framework associated with the first and second arm 604-1, 604-5 can include a cutout in which the magnetic position sensors 602-1, 602-2 can be disposed, respectively. In some embodiments, the framework associated with the first and second arm 604-1, 604-5 can include a slot, as discussed in FIGS. 12A and 12B. Although the first and second arms 604-1, 604-2 are generally discussed herein, the magnetic position sensors can be disposed on other ones of the arms 604-2, 604-3, 604-4 in some embodiments. While the magnetic position sensors 602-1, 602-2 are depicted as being disposed on a distal portion of the longitudinally extending portion of the first and second arms 604-1, 604-2, the magnetic position sensors 602-1, 602-2 can be disposed distally of their presently depicted locations and/or can be disposed proximally of their presently depicted locations.

In some embodiments, the framework associated with the arms 604-1, 604-2, . . . , 604-5 can include nitinol, stainless steel, titanium, among other materials. In some embodiments, a tubing can be disposed over the magnetic position sensors 602-1, 602-2, to help retain the magnetic position sensors, so they do not become detached. In some embodiments, a tubing can be placed over the magnetic position sensors 602-1, 602-2, which is disposed inside an outer tubing on which the electrodes 608 are disposed. In some embodiments, the outer tubing can serve to retain the magnetic position sensors 602-1, 602-2, without use of an inner tubing.

Embodiments are described herein of various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it may be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment(s) is included in at least one embodiment. Thus, appearances of the phrases "in various embodiments," "in some embodiments," "in one embodiment," or "in an embodiment," or the like, in places throughout the specification, are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Although at least one embodiment for a high-density electrode catheter has been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the devices. Joinder references (e.g., affixed, attached, coupled, connected, and the like) are to be construed broadly and may include intermediate members between a connection of elements and relative movement between elements. As such, joinder references do not necessarily infer that two elements are directly connected and in fixed relationship to each other. It is intended that all matter contained in the above description or shown in the accompanying drawings shall be interpreted as illustrative only and not limiting. Changes in detail or structure may be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed:

1. A high-density electrode catheter comprising:
    a catheter shaft including a proximal end and a distal end, the catheter shaft defining a catheter shaft longitudinal axis;
    a shaft magnetic position sensor disposed along a distal portion of the catheter shaft;
    a flexible tip portion located adjacent to the distal end of the catheter shaft, wherein the flexible tip portion includes a flexible framework comprising:
        first and second longitudinally extending outboard arms;
        first and second longitudinally extending inboard arms; and a central arm that extends between the first and second longitudinally extending inboard arms;

a proximal coupler from which the first and second outboard arms, the first and second inboard arms, and the central arm extend, wherein the first and second outboard arms and the first and second inboard arms exit the proximal coupler on a first plane that runs along a longitudinal axis of each of the first and second outboard and inboard arms and the central arm exits the proximal coupler offset from the first plane and extends distally away from the proximal coupler and toward the first plane;

a plurality of electrodes disposed on the flexible framework;

a first magnetic position sensor disposed on the first outboard arm;

a second magnetic position sensor disposed on the second outboard arm; and a distal coupler that couples distal portions of the first and second outboard arms, first and second inboard arms, and the central arm on the first plane; wherein the central arm includes a single longitudinally extending arm; and the central arm includes a lengthening feature; wherein the lengthening feature includes a bend formed in the single longitudinally extending arm; and the lengthening feature is configured to elongate when the flexible tip portion is in a collapsed state.

2. The high-density electrode catheter of claim 1, wherein each of the first and second outboard arms defines a lumen in which the magnetic position sensor is disposed.

3. The high-density electrode catheter of claim 1, further comprising an electrode disposed along each of the first and second outboard arms, wherein the electrode defines a lumen in which the magnetic position sensor is disposed.

4. The high-density electrode catheter of claim 1, wherein:
the first and second outboard arms, the first and second inboard arms, and the central arm extend distally with respect to the distal end of the catheter shaft; and
a tip magnetic position sensor is disposed at a distal end of the central arm.

5. The high-density electrode catheter of claim 1, wherein:
the central arm includes an electrode disposed at a distal end of the central arm.

6. The high-density electrode catheter of claim 1, wherein the distal coupler includes a tip magnetic position sensor.

7. The high-density electrode catheter of claim 6, wherein the distal coupler defines a lumen in which the tip magnetic position sensor is disposed.

8. The high-density electrode catheter of claim 6, wherein the distal coupler defines a keyed slot into which the distal end of the central arm is disposed.

9. A high-density electrode catheter comprising:
a catheter shaft including a proximal end and a distal end, the catheter shaft defining a catheter shaft longitudinal axis;
a flexible tip portion located adjacent to the distal end of the catheter shaft, wherein the flexible tip portion includes a flexible framework that includes a longitudinally extending first outboard arm, second outboard arm, first inboard arm, second inboard arm, and central arm;
a proximal coupler from which the first and second outboard arms, the first and second inboard arms, and the central arm extend, wherein the first and second outboard arms and the first and second inboard arms exit the proximal coupler on a first plane that runs along a longitudinal axis of each of the first and second outboard and inboard arms and the central arm exits the proximal coupler offset from the first plane and extends distally away from the proximal coupler and toward the first plane;
a plurality of electrodes disposed on each of the first outboard arm, second outboard arm, first inboard arm, second inboard arm, and central arm;
a first tip magnetic position sensor disposed on the first outboard arm;
a second tip magnetic position sensor disposed on the second outboard arm; and
a distal coupler that couples distal portions of the first and second outboard arms, first and second inboard arms, and the central arm on the first plane, wherein the distal coupler defines a keyed slot into which a distal end of the central arm is disposed; wherein the central arm includes a single longitudinally extending arm; and the central arm includes a lengthening feature; wherein the lengthening feature includes a bend formed in the single longitudinally extending arm; and the lengthening feature is configured to elongate when the flexible tip portion is in a collapsed state.

10. The high-density electrode catheter of claim 9, wherein:
proximal ends of the central arm, the first and second outboard arms, and the first and second inboard arms each include a mounting portion.

11. The high-density electrode catheter of claim 10, wherein the mounting portions include clips, which are fastened to the proximal coupler.

12. A high-density electrode catheter comprising:
a catheter shaft including a proximal end and a distal end, the catheter shaft defining a catheter shaft longitudinal axis;
a flexible tip portion located adjacent to the distal end of the catheter shaft, wherein the flexible tip portion includes a flexible framework comprising:
first and second longitudinally extending outboard arms;
first and second longitudinally extending inboard arms; and
a central arm that extends between the first and second longitudinally extending inboard arms;
a proximal coupler from which the first and second outboard arms, the first and second inboard arms, and the central arm extend, wherein the first and second outboard arms and the first and second inboard arms exit the proximal coupler on a first plane that runs along a longitudinal axis of each of the first and second outboard and inboard arms and the central arm exits the proximal coupler offset from the first plane and extends distally away from the proximal coupler and toward the first plane;
a flexible circuit disposed on the flexible framework, wherein the flexible circuit includes a plurality of electrodes disposed thereon;
a tip magnetic position sensor disposed on a distal portion of the flexible framework; and
a distal coupler that couples distal portions of the first and second outboard arms, first and second inboard arms, and the central arm on the first plane; wherein the central arm includes a single longitudinally extending arm; and the central arm includes a lengthening feature; wherein the lengthening feature includes a bend formed in the single longitudinally extending arm; and the lengthening feature is configured to elongate when the flexible tip portion is in a collapsed state.

13. The high-density electrode catheter of claim 12, wherein:
   the flexible circuit is disposed on a top and bottom of the flexible framework; and
   the flexible circuit transitions to a top surface of the flexible framework and a bottom surface of the flexible framework at a transition point.

14. The high-density electrode catheter of claim 13, wherein the flexible circuit extends on the top surface of the flexible framework and the bottom surface of the flexible framework distally of the transition point.

\* \* \* \* \*